United States Patent
Devi

(10) Patent No.: US 10,195,164 B2
(45) Date of Patent: Feb. 5, 2019

(54) USE OF DISULFIRAM FOR INFLAMMATORY BREAST CANCER THERAPY

(71) Applicant: Duke University, Durham, NC (US)

(72) Inventor: Gayathri Devi, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/154,473

(22) Filed: May 13, 2016

(65) Prior Publication Data

US 2017/0020828 A1  Jan. 26, 2017

Related U.S. Application Data

(60) Provisional application No. 62/160,791, filed on May 13, 2015.

(51) Int. Cl.
| | |
|---|---|
| *A61K 31/45* | (2006.01) |
| *A61K 33/34* | (2006.01) |
| *A61K 31/145* | (2006.01) |
| *A61K 45/06* | (2006.01) |
| *A61K 31/166* | (2006.01) |
| *A61K 31/555* | (2006.01) |

(52) U.S. Cl.
CPC .......... *A61K 31/145* (2013.01); *A61K 31/166* (2013.01); *A61K 31/555* (2013.01); *A61K 33/34* (2013.01); *A61K 45/06* (2013.01)

(58) Field of Classification Search
CPC ...... A61K 33/34; A61K 31/145; A61K 45/06; A61K 31/166; A61K 31/555; A61K 2300/00
See application file for complete search history.

(56) References Cited

U.S. PATENT DOCUMENTS

| | | | | |
|---|---|---|---|---|
| 2004/0019102 A1* | 1/2004 | Kennedy | ............. | A61K 31/325 514/476 |
| 2010/0137247 A1* | 6/2010 | Hyde | .................... | A61K 9/0019 514/64 |
| 2014/0037715 A1* | 2/2014 | Wang | .................... | A61K 9/127 424/450 |

OTHER PUBLICATIONS

WebMD. "Understanding Breast Cancer—Prevention". Retrieved on Mar. 6, 2017. Retrieved from the internet <URL: http://www.webmd.com/breast-cancer/guide/understanding-breast-cancer-prevention>.*
Penn Medicine. "Inflammatory Breast Cancer Risks & Prevention". Retrieved on Mar. 6, 2017. Retrieved from the internet <URL: https://www.pennmedicine.org/cancer/types-of-cancer/breast-cancer/types-of-breast-cancer/inflammatory-breast-cancer/inflammatory-breast-cancer-risk-prevention>.*
Cancer.net. "Breast Cancer—Inflammatory: Risk Factors". Retrieved on Mar. 6, 2017. Retrieved from the internet <URL: http://www.cancer.net/cancer-types/breast-cancer-inflammatory/risk-factors>.*
Mayo Clinic. "Recurrent breast cancer". Retrieved on Mar. 6, 2017. Retrieved from the internet <URL: http://www.mayoclinic.org/diseases-conditions/recurrent-breast-cancer/basics/prevention/con-20032432>.*
Cancer.org. "Can Advanced or metastatic cancer be prevented?" Retrieved on Mar. 6, 2016. Retrieved from the internet <URL: https://www.cancer.org/treatment/understanding-your-diagnosis/advanced-cancer/prevention.html>.*
Robertson et al (2010). "Inflammatory Breast Cancer". Ca Cancer J Clin., 60: 351-375.*
Allensworth, Jennifer. (Jul. 24, 2013). Identification and Targeting of Therapeutic Resistance Mechanisms in Inflammatory Breast Cancer (Doctoral dissertation). Retrieved from URL: http://citeseerx.ist.psu.edu/viewdoc/download?doi=10.1.1.892.5434&rep=rep1&type=pdf ; pp. 1-286.*
Exhibit 1. Allensworth, J. L. (2013). Identification and targeting of therapeutic resistance mechanisms in inflammatory breast cancer (Order No. 3590817). Available from ProQuest Dissertations & Theses Global. (1433010029). Retrieved from https://search.proquest.com/docview/1433010029?accountid=14753. pp. 1-5.*
Exhibit 2. Allensworth, J. L. (2013). Available from ProQuest Dissertations & Theses Global. (1433010029). Retrieved from https://search.proquest.com/docview/1433010029?accountid=14753. Screenshot of Document Properties. Retrieved Jan. 31, 2018. pp. 1-2.*
Exhibit 3. Allensworth, J. L. (2013). Available from DukeSpace Libraries. Retrieved from https://dukespace.lib.duke.edu/dspace/handle/10161/808. Screenshot of Document Properties. Retrieved Jan. 31, 2018. pp. 1-2.*
Aapro M, et al. Triple-negative breast cancer in the older population. Annals of oncology : official journal of the European Society for Medical Oncology / ESMO. 2012; 23 Suppl 6: vi52-5.
Abramoff M.D., et al. , 2004. Image Processing with ImageJ. Biophotonics International 11, 36-42.
Abramowitz, MC, et al. Dermal Lymphatic Invasion and Inflammatory Breast Cancer Are independent Predictors of Outcome After Postmastectomy Radiation. American Journal of Clinical Oncology. 2009, 32(1):30-33.
Abrous-Anane S. et al. Management Inflammatory Breast Cancer After Neoadjuvant Chemotherapy. International Journal Radiation Oncology Biology Physics, (2011) 79(4):1055-1063.
Acharya A, Das I, Chandhok D, Saha T. Redox regulation in cancer: a double-edged sword with therapeutic potential. Oxidative medicine and cellular longevity. 2010; 3(1): 23-34.
Ambrosone CB. Oxidants and antioxidants in breast cancer. Antioxidants & redox signaling. 2000; 2(4): 903-17.
Aird K.M., et al., 2012. ErbB1/2 tyrosine kinase inhibitor mediates oxidative stress-induced apoptosis in inflammatory breast cancer cells. Breast cancer research and treatment 132, 109-119.
Aird K.M., et al.., 2008. Trastuzumab in signaling in ErbB2-overexpressing inflammatory breast cancer correlates with X-linked inhibitor of apoptosis protein expression. Molecular cancer therapeutics 7, 38-47.

(Continued)

*Primary Examiner* — Doan T Phan
(74) *Attorney, Agent, or Firm* — Quarles & Brady LLP

(57) ABSTRACT

Methods, compositions of matter, and kits for treatment of breast cancer, and in particular for inflammatory breast cancer, in a patient are disclosed. The methods can include administering a redox modulating agent to the patient. The redox modulating agent can be disulfiram.

13 Claims, 51 Drawing Sheets
(18 of 51 Drawing Sheet(s) Filed in Color)

(56) References Cited

OTHER PUBLICATIONS

Aird K.M., et al., 2010. X-linked inhibitor of apoptosis protein inhibits apoptosis in inflammatory breast cancer cells with acquired resistance to an ErbB1/2 tyrosine kinase inhibitor. Molecular cancer therapeutics 9, 1432-1442.

Al-Abd, AM, et al. Didox potentiates the cytotoxic profile of doxorubicin and protects from its cardiotoxicity, European Journal of Pharmacology, (2013), 718(1-3):361-369.

Allensworth, J.L., et al., 2012. XIAP inhibition and generation of reactive oxygen species enhances TRAIL sensitivity in inflammatory breast cancer cells. Molecular cancer therapeutics 11, 1518-1527.

Allensworth, J.L., et al., 2013. Smac mimetic Birinapant induces apoptosis and enhances TRAIL potency in inflammatory breast cancer cells in an IAP-dependent and TNF-alpha-independent mechanism. Breast cancer research and treatment 137, 359-371.

Badawi AF, et al. Role of human cytochrome P450 1A1, 1A2, 1B1, and 3A4 in the 2-, 4-, and 16alpha-hydroxylation of 17beta-estradiol. Metabolism: clinical and experimental. 2001; 50(9): 1001-3.

Bae I, et al. BRCA1 induces antioxidant gene expression and resistance to oxidative stress. Cancer Res. 2004; 64 (21): 7893-909.

Balkwill F. Tumor necrosis factor or tumor promoting factor? Cytokine & growth factor reviews. 2002; 13(2): 135-41.

Barbano R, et al. Aberrant Keap1 methylation in breast cancer and association with clinicopathological features. Epigenetics : official journal of the DNA Methylation Society. 2012; 8(1): 105-12.

Bartosz, G. Reactive oxygen species: destroyers or messengers? Biochem Pharmacol. 2009; 77(8): 1303-15. doi: 10.016/j.bcp.2008. 11.009. Epub Nov. 24.

Bellezza I., et al., 2010. Nrf2 and NF-kappaB and Their Concerted Modulation in Cancer Pathogenesis and Progression. Cancers 2, 483-497.

Bertucci, F., et al., 2013. Gene expression profiles of inflammatory breast cancer: correlation with response to neoadjuvant chemotherapy and metastasis-free survival. Annals of oncology : official journal of the European Society for Medical Oncology / ESMO.

Bhartl AC, Aggarwal BB. Nuclear factor-kappa B and cancer: Its role in prevention and therapy. Biochem Pharmacol. 2002; 64(5-6): 883-8.

Blancher C, et al. Relationship of hypoxia-inducible factor (HIF)-1alpha and HIF-2alpha expression to vascular endothelial growth factor induction and hypoxia survival in human breast cancer cell lines. Cancer research. 2000; 60(24): 7106-13.

Bolton JL, et al. Potential mechanisms of estrogen quinone carcinogenesis. Chemical research in toxicology. 2008; 21(1): 93-101.

Bourgier C. et al. Exclusive Alternating Chemotherapy and Radiotherapy in Nonmetastatic Inflammatory Breast Cancer: 20 Years of Follow-Up, Internation Journal of Radiation Oncology Biology Physics, (2012), 82(2):690-695.

Brewer, G.J., 2009. The use of copper-lowering therapy with tetrathiomolybdate in medicine. Expert opinion on investigational drugs 18, 89-97.

Brown, N.S., et al., 2001. Hypoxia and oxidative stress in breast cancer. Oxidative stress: Its effect on the growth, metastatic potential and response to therapy of breast cancer. Breast cancer research : BCR 3, 323-327.

Browne EP, et al. Increased promoter methylation in exfoliated breast epithelial cells in women with a previous breast biopsy. Epigenetics : official journal of the DNA Methylation Society. 2011; 6(12): 1425-35.

Cao, B. et al. Metabolomic approach to evaluating adriamycin pharmacodynamics and resistance in breast cancer cells, Metabolomics, (2013), 9(5):960.

Cen, D., et al., 2004. Disulfiram facilitates intracellular Cu uptake and induces apoptosis in human melanoma cells. Journal of medicinal chemistry 47, 6914-6920.

Charafe-Jauffret, E., et al., 2010. Aldehyde dehydrogenase 1-positive cancer stem cells mediate metastasis and poor clinical outcome in inflammatory breast cancer. Clinical cancer research : an official journal of the American Association for Cancer Research 16, 45-55.

Chen, D., et al., 2006. Disulfiram, a clinically used anti-alcoholism drug and copper-binding agent, induces apoptotic cell death in breast cancer cultures and xenografts via inhibition of the proteasome activity. Cancer research 66, 10425-10433.

Chen CL, et al. Hypoxia and metabolic phenotypes during breast carcinogenesis: expression of HIF-1alpha, GLUT1, and CAIX. Virchows Archiv : an international journal of pathology. 2010; 457(1): 53-61.

CHEN EI, et al. Adaptation of energy metabolism in breast cancer brain metastases. Cancer Res. 2007; 67(4): 1472-86.

Clemons M, et al. Estrogen and the risk of breast cancer. The New England journal of medicine. 2001; 344(4):276-85.

Croker, A.K., et al., 2009. High aldehyde dehydrogenase and expression of cancer stem cell markers selects for breast cancer cells with enhanced malignant and metastatic ability. Journal of cellular and molecular medicine 13, 2236-2252.

Cui H, et al. Oxidative stress, mitochondrial dysfunction, and aging. Journal of signal transduction. 2012; 2012:646354.

Dawood, S., et al.; 2011. Inflammatory breast cancer: what progress have we made? Oncology (Williston Park, N.Y.) 25, 264-270, 273.

Dawood, S. Differences in survival among women with stage III inflammatory and noninflammatory locally advanced breast cancer appear early. Cancer. 2011, 117(9):1819-1826.

Debeb, B.G., et al., 2012. Pre-clinical studies of Notch signaling inhibitor RO4929097 in inflammatory breast cancer cells. Breast cancer research and treatment 134, 495-510.

Degraffenried LA, et al. NF-kappa B inhibition markedly enhances sensitivity of resistant breast cancer tumor cells to tamoxifen. Ann Oncol. 2004; 15(6): 885-90.

Diehn, M., et al., 2009. Association of reactive oxygen species levels and radioresistance in cancer stem cells. Nature 458, 780-783.

Donate LE, et al. Telomeres in cancer and ageing. Philosophical transactions of the Royal Society of London Series B, Biological sciences. 2011; 366(1561): 76-84.

Droge, W. Free radicals in the physiological control of cell function. Physiological reviews. 2002; 82(1): 47-95.

Eades G, Yet al. miR-200a regulates Nrf2 activation by targeting Keap1 mRNA in breast cancer cells. The Journal of biological chemistry. 2011; 286(47): 40725-33.

Er TK, et al. Differential expression of manganese containing superoxide dismutase in patients with breast cancer in Taiwan. Annals of clinical and laboratory science. 2004; 34(2): 159-64.

Eralp Y, et al. MAPK overexpression is associated with anthracycline resistance and increased risk for recurrence in patients with triple-negative breast cancer. Annals of oncology : official journal of the European Society for Medical Oncology / ESMO. 2008; 19(4): 669-74.

Esworthy RS, et al. Expression of selenium-dependent glutathione peroxidase in human breast tumor cell lines. Cancer research. 1995; 55(4): 957-62.

Evans, M.K., et al., 2014. Mn porphyrin in combination with ascorbate acts as a pro-oxidant and mediates caspase-independent cancer cell death. Free radical biology & medicine 68c, 302-314.

Faiman, M.D., et al., 1984. Elimination kinetics of disulfiram in alcoholics after single and repeated doses. Clinical pharmacology and therapeutics 36, 520-526.

Figul, A. et al. Combined effects of temozolomide and the ribonucleotide reductase inhibitors didox and trimidox in malignant brain tumor cells, Cancer Chemotherapy and Pharmacology, (2003) 52(1):41-46.

Forman HJ, et al. Signaling functions of reactive oxygen species. Biochemistry. 2010; 49(5): 835-42. doi: 10.1021/bi9020378.

Nadal-Serrano M, et al. The ERalpha/ERbeta ratio determines oxidative stress in breast cancer cell lines in response to 17beta-estradiol. Journal of cellular biochemistry. 2012; 113(10): 3178-85.

Nagata Y, et al. PTEN activation contributes to tumor inhibition by trastuzumab, and loss of PTEN predicts trastuzumab resistance in patients. Cancer Cell. 2004; 6(2): 117-27.

(56) References Cited

OTHER PUBLICATIONS

Nguyen, D.M., et al., 2006. Molecular heterogeneity of inflammatory breast cancer: a hyperproliferative phenotype. Clinical cancer research : an official journal of the American Association for Cancer Research 12, 5047-5054.
Nitta, M, et al. Targeting EGFR induced oxidative stress by PARP1 inhibition in glioblastoma therapy. PloS one. 2010; 5(5): e10767.
Noh Dy, et al. Overexpression of peroxiredoxin in human breast cancer. Anticancer research. 2001; 21(3B): 2085-90.
Nose, Y., et al., 2006. Ctr1 drives intestinal copper absorption and is essential for growth, iron metabolism, and neonatal cardiac function. Cell metabolism 4, 235-244.
Pena, M.M., et al., 1998. Dynamic regulation of copper uptake and detoxification genes in *Saccharomyces cerevisiae*. Molecular and cellular biology 18, 2514-2523.
Portakal O, et al. Coenzyme Q10 concentrations and antioxidant status in tissues of breast cancer patients. Clin Biochem. 2000; 33(4): 279-84.
Punnonen K, et al. Antioxidant enzyme activities and oxidative stress in human breast cancer. J Cancer Res Clin Oncol. 1994; 120(6): 374-7.
Raje, N, et al. Didox, a ribonucleotide reductase inhibitor, induces apoptosis and inhibits DNA repair in multiple myeloma cells, British Journal of Haematology, (2006), 135(1):52-61.
Ramanathan B, et al. Resistance to paciitaxel is proportional to cellular total antioxidant capacity. Cancer research. 2005; 65(18): 8455-60.
Ray G, et al. Lipid peroxidation, free radical production and antioxidant status in breast cancer. Breast Cancer Res Treat. 2000; 59(2): 163-70.
Reeder, N.L., et al., 2011. Zinc pyrithione inhibits yeast growth through copper influx and inactivation of iron-sulfur proteins. Antimicrobial agents and chemotherapy 55, 5753-5760.
Ristimaki A, et al. Prognostic significance of elevated cyclooxygenase-2 expression in breast cancer. Cancer research. 2002; 62(3): 632-5.
Rizk, S.L., et al., 1984. Comparison between concentrations of trace elements in normal and neoplastic human breast tissue. Cancer research 44, 5390-5394.
Robertson, F.M.,et al., 2010. Inflammatory breast cancer: the disease, the biology, the treatment. CA: a cancer journal for clinicians 60, 351-375.
Robinson, J.S., et al., 1988. Protein sorting in *Saccharomyces cerevisiae*: isolation of mutants defective in the delivery and processing of multiple vacuolar hydrolases. Molecular and cellular biology 8, 4936-4948.
Robinson MF, et al. Blood selenium and glutathione peroxidase activity in normal subjects and in surgical patients with and without cancer in New Zealand. The American journal of clinical nutrition. 1979; 32(7): 1477-85.
Rohan TE, et al. Do alterations in mitochondrial DNA play a role in breast carcinogenesis? Journal of oncology. 2010; 2010: 604304.
Rubens, RD, et al. Phase II trial of didox in advanced breast cancer. Cancer Research Campaign Phase I/II Clinical Trials Committee., British Journal of Cancer, (1991), 64(6):1187-1188.
Rueth, N.M., et al., 2014. Underuse of trimodality treatment affects survival for patients with inflammatory breast cancer: an analysis of treatment and survival trends from the national cancer database. Journal of clinical oncology : official journal of the American Society of Clinical Oncology 32, 2018-2024.
Sastre-Serra J, Valle A, Company MM, Garau I, Oliver J, Roca P. Estrogen down-regulates uncoupling proteins and increases oxidative stress in breast cancer. Free radical biology & medicine. 2010; 48(4): 506-12.
Saigal, K., et al., Wright, J.L., 2013. Risk factors for locoregional failure in patients with inflammatory breast cancer treated with trimodality therapy. Clinical breast cancer 13, 335-343.
Schafer FQ, et al. Redox environment of the cell as viewed through the redox state of the glutathione disulfide/glutathione couple. Free radical biology & medicine. 2001; 30(11): 1191-212.

Schor NF, et al. Exploiting oxidative stress and signaling in chemotherapy of resistant neoplasms. Biochemistry (Mosc). 2004; 69(1): 38-44.
Shah, KN, et al. Abstract 4227: The ribonucleotide reductase inhibitor Didox reverses tamoxifen resistance in breast cancer cells, Cancer Research, (2014), 74(19).
Silvera, D., et al., 2009. Essential role for eIF4GI overexpression in the pathogenesis of inflammatory breast cancer. Nature cell biology 11, 903-908.
Simpson, ER, et al. Minireview: Obesity and breast cancer: a tale of inflammation and dysregulated metabolism. Mol Endocrinol. 2013; 27(5): 715-25.
Simpson ER, et al. Aromatase—a brief overview. Annual review of physiology. 2002; 64: 93-127.
Singh, S., et al., 2013. Aldehyde dehydrogenases in cellular responses to oxidative/electrophilic stress. Free radical biology & medicine 56, 89-101.
Singh B, et al. Selection of metastatic breast cancer cells based on adaptability of their metabolic state. PLoS One. 2012; 7(5): e36510. doi: 10.1371/journal.pone.0036510. Epub May 3, 2012.
Singhapol C, et al. Mitochondrial telomerase protects cancer cells from nuclear DNA damage and apoptosis. PloS one. 2013; 8(1): e52989.
Samoylenko, A, et al. Nutritional Countermeasures Targeting Reactive Oxygen Species in Cancer: From Mechanisms to Biomarkers and Clinical Evidence. Antioxidants & redox signaling. 2013.
Soderlund K, et al. Activation of the phosphatidylinositol 3-kinase/Akt pathway prevents radiation-induced apoptosis in breast cancer cells. Int J Oncol. 2005; 26(1): 25-32.
Sprowl JA, et al. Alterations in tumor necrosis factor signaling pathways are associated with cytotoxicity and resistance to taxanes: a study in isogenic resistant tumor cells. Breast Cancer Res. 2012; 14(1): R2.
Stefansson OA, et al. BRCA1 epigenetic inactivation predicts sensitivity to platinum-based chemotherapy in breast and ovarian cancer. Epigenetics : official journal of the DNA Methylation Society. 2012; 7(11): 1225-9.
Svensson S, et al. ERK phosphorylation is linked to VEGFR2 expression and Ets-2 phosphorylation in breast cancer and is associated with tamoxifen treatment resistance and small tumours with good prognosis. Oncogene. 2005; 24(27): 4370-9.
Syed Alwi SS, et al. Differential induction of apoptosis in human breast cancer cell lines by phenethyl isothiocyanate, a glutathione depleting agent. Cell Stress Chaperones. 2012; 17(5): 529-38. doi: 10.1007/s12192-012-0329-3. Epub Feb. 17, 2012.
Taminau, J., et al., 2012. Unlocking the potential of publicly available microarray data using inSilicoDb and inSilicoMerging R/Bioconductor packages. BMC bioinformatics 13, 335.
Tanaka T, et al. High incidence of allelic loss on chromosome 5 and inactivation of p15INK4B p16INK4A tumor suppressor genes in oxystress-induced renal cell carcinoma of rats. Oncogene. 1999: 18(25): 3793-7.
Tas F, et al. Oxidative stress in breast cancer. Med Oncol. 2005; 22(1): 11-5.
Tapia MA, et al. Inhibition of the canonical IKK/NF kappa B pathway sensitizes human cancer cells to doxorubicin. Cell Cycle. 2007; 6(18): 2284-92. Epub 007 Jul. 10.
Tian H, et al. Keap1: one stone kills three birds Nrf2, IKKbeta and Bci-2/Bci-xL. Cancer Lett. 2012: 325(1): 26-34. doi: 10.1016/j.canlet.2012.06.007. Epub Jun. 26.
Tokunaga E, et al. Akt is frequently activated in HER2/neu-positive breast cancers and associated with poor prognosis among hormone-treated patients. Int J Cancer. 2006; 118(2): 284-9.
Toyokuni, S. et al. Persistent oxidative stress in cancer, FEBS Letter, (1995) 358(1):1-3.
Trachootham, D., et al., 2009. Targeting cancer cells by ROS-mediated mechanisms: a radical therapeutic approach? Nature reviews. Drug discovery 8, 579-591.
Truong TH, et al. Redox regulation of epidermal growth factor receptor signaling through cysteine oxidation. Biochemistry. 2012; 51(50): 9954-65.
Van Laere, S.J., et al., 2013. Uncovering the molecular secrets of inflammatory breast cancer biology: an integrated analysis of three

(56) References Cited

OTHER PUBLICATIONS distinct affymetrix gene expression datasets. Clinical cancer research : an official journal of the American Association for Cancer Research 19, 4685-4696.
Van Laere, S.J., et al., 2006. Nuclear factor-kappaB signature of inflammatory breast cancer by cDNA microarray validated by quantitative real-time reverse transcription-PCR, immunohistochemistry, and nuclear factor-kappaB DNA-binding. Clinical cancer research : an official journal of the American Association for Cancer Research 12, 3249-3256.
Vermeulen, PB, et al. Angiogenesis, lymphangiogenesis, growth pattern, and tumor emboli in inflammatory breast cancer, Cancer, (2010) 116(S11):2748-2754.
Fraga, C.G., 2005. Relevance, essentiality and toxicity of trace elements in human health. Molecular aspects of medicine 26, 235-244.
Giampieri, S. et al. Locaiized and reversible TGFβ signaling switches breast cancer cells from cohesive to single cell motility, Nature Cell Biology, (2009), 11:1287-1296.
Generali D, et al. Hypoxia-inducible factor-1alpha expression predicts a poor response to primary chemoendocrine therapy and disease-free survival in primary human breast cancer. Clinical cancer research : an official journal of the American Association for Cancer Research. 2006; 12(15): 4562-8.
Gorrini, C., et al., 2013. Modulation of oxidative stress as an anticancer strategy. Nature reviews. Drug discovery 12, 931-947.
Gridley, DS: et al. Radiation and a Metalloporphyrin Radioprotectant in a Mouse Prostate Tumor Model, Anticancer Research, (2007), 27(5a):3101-3109.
Gupte, A., et al., 2009. Elevated copper and oxidative stress in cancer cells as a target for cancer treatment. Cancer treatment reviews 35, 32-46.
Guo G, et al. Manganese superoxide dismutase-mediated gene expression in radiation-induced adaptive responses. Molecular and cellular biology, 2003; 23(7): 2362-78.
Han, D. et al. Mitochondrial respiratory chain-dependent generation of superoxide anion and its release into the intermembrane space. The Biochemical journal. 2001; 353(Pt 2): 411-6.
Hanahan, D. et al. Hallmarks of Cancer: The Next Generation, Cell, (2011). 144(5):646-674.
Hance, KW, et al. Trends in inflammatory breast carcinoma incidence and survival: the surveillance, epidemiology, and end results program at the National Cancer Institute. J Natl Cancer Inst (2005) 97 (13): 966-975.
Hogarth, G., 2012. Metal-dithiocarbamate complexes: chemistry and biological activity. Mini reviews in medicinal chemistry 12, 1202-1215.
Hou Z, et al. Macrophages induce COX-2 expression in breast cancer cells: role of IL-1beta autoamplification. Carcinogenesis. 2011; 32(5): 695-702.
Howlander N, et al. SEER Cancer Statistics Review, 1975-2010. National Cancer Institute Bethesda, MD, http://seercancergov/csr/1975_2010/, based on Nov. 2012 SEER data submission. (based on Nov. 2012 SEER data submission, posted to the SEER web site, Apr. 2013).
Hirst ,DG, et al. Nitrosative stress in cancer therapy. Frontiers in bioscience : a journal and virtual library. 2007; 12:3406-18,
Hitchler MJ, et al. Epigenetic regulation of manganese superoxide dismutase expression in human breast cancer cells. Epigenetics : official journal of the DNA Methylation Society. 2006; 1(4): 163-71.
Indran IR, et al. hTERT overexpression alleviates intracellular ROS production, improves mitochondrial function, and inhibits ROS-mediated apoptosis in cancer cells. Cancer research. 2011; 71(1): 266-76.
Inayat, MS, et al. Didox (A Novel Ribonucleotide Reductase Inhibitor) Overcomes bcl-2 Mediated Radiation Resistance in Prostate Cancer Cell Line PC-3, Cancer Biology & Therapy, (2002) 1:5, 539-545.

Iwamoto, T., et al., 2011. Different gene expressions are associated with the different molecular subtypes of inflammatory breast cancer. Breast cancer research and treatment 125, 785-795.
Iwao-Koizumi K, et al. Prediction of docetaxel response in human breast cancer by gene expression profiling. J Clin Oncol. 2005, 23(3). 422-31.
Januchowski, R., et al., 2013. The role of aldehyde dehydrogenase (ALDH) in cancer drug resistance. Biomedicine & pharmacotherapy 67, 669-680.
Jardim BV, et al. Glutathione and glutathione peroxidase expression in breast cancer: An immunohistochemical and molecular study. Oncology reports. 2013.
Johansson, B., 1992. A review of the pharmacokinetics and pharmacodynamics of disulfiram and its metabolites. Acta psychiatrica Scandinavica. Supplementum 369, 15-26.
Kalinina EV, et al. Changes in expression of genes encoding antioxidant enzymes, heme oxygenase-1, Bcl-2, and Bcl-xl and in level of reactive oxygen species in tumor cells resistant to doxorubicin. Biochemistry (Mosc). 2006; 71(11): 1200-6.
Kattan Z, et al. Role of manganese superoxide dismutase on growth and invasive properties of human estrogen-independent breast cancer cells. Breast cancer research and treatment. 2008; 108(2): 203-15.
Kashkar, H., 2010. X-linked inhibitor of apoptosis: a chemoresistance factor or a hollow promise. Clinical cancer research : an official journal of the American Association for Cancer Research 16, 4496-4602.
Khuder SA, et al. Breast cancer and NSAID use: a meta-analysis. British journal of cancer. 2001; 84(9): 1188-92.
Kim SJ, et al. High thioredoxin expression is associated with resistance to docetaxel in primary breast cancer. Clinical cancer research : an official journal of the American Association for Cancer Research. 2005; 11(23): 8425-30.
Kim SK, et al. Increased expression of Nrf2/ARE-dependent antioxidant proteins in tamoxifen-resistant breast cancer cells. Free Radio Biol Med. 2008; 45(4): 537-46. doi: 10.1016/j.freeradbiomed.2008.05.011. Epub May 24.
Klopp, A.H., et al., 2010. Mesenchymal stem cells promote mammosphere formation and decrease E-cadherin in normal and malignant breast cells. PloS one 5, e12180.
Kumaraguruparan R, et al. Tissue lipid peroxidation and antioxidant status in patients with adenocarcinoma of the breast. Clin Chim Acta. 2002; 325(1-2): 165-70.
Kumaraguruparan R, et al. Correlation of tissue lipid peroxidation and antioxidants with clinical stage and menopausal status in patients with adenocarcinoma of the breast. Clin Biochem. 2005; 38(2): 154-8.
Kurokawa, M. et al. A Network of Substrates of the E3 Ubiquitin Ligases MDM2 and HUWE1 Control Apoptosis Independently of p53, Sci Signal, (2013), 6(274):ra32.
Lal A, et al. Transcriptional response to hypoxia in human tumors. Journal of the National Cancer Institute. 2001: 93(17); 1337-43.
Lehman, HL, et al. Modeling and characterization of inflammatory breast cancer emboli grown in vitro, International Journal of Cancer, Cancer Cell Biology, (2013). 132(10):2283-2294.
Li Z, et al. Role of PKC-ERK signaling in tamoxifen-induced apoptosis and tamoxifen resistance in human breast cancer cell. Oncology reports. 2012; 27(6): 1879-86.
Liang K, et al. Targeting the phosphatidylinositol 3-kinase/Akt pathway for enhancing breast cancer cells to radiotherapy. Mol Cancer Ther. 2003; 2(4): 353-60.
Lithgow D, et al. Chronic inflammation and breast pathology: a theoretical model. Biological research for nursing. 2005; 7(2): 118-29.
Loignon M, et al. Cul3 overexpression depletes Nrf2 in breast cancer and is associated with sensitivity to carcinogens, to oxidative stress, and to chemotherapy. Mol Cancer Ther. 2009; 8(8): 2432-40. doi: 10.1158/535-7163. MCT-08-1186. Epub Jul. 28, 2009.
Lu Z, et al. ERK1/2 MAP kinases in cell survival and apoptosis. IUBMB Life. 2006; 58(11): 621-31.
Maitra A, et al. High-resolution chromosome 3p allelotyping of breast carcinomas and precursor lesions demonstrates frequent loss

(56) References Cited

OTHER PUBLICATIONS of heterozygosity and a discontinuous pattern of allele loss. The American journal of pathology. 2001; 159(1): 119-30.

Manda, G., et al., 2009. Reactive Oxygen Species, Cancer and Anti-Cancer Therapies. Current Chemical Biology 3, 22-46.

Masuda, H., et al., 2014. Long-term treatment efficacy in primary inflammatory breast cancer by hormonal receptor- and HER2-defined subtypes. Annals of oncology : official journal of the European Society for Medical Oncology / ESMO 25, 384-391.

Mates JM, et al. Intracellular redox status and oxidative stress: Implications for cell proliferation, apoptosis, and carcinogenesis. Archives of toxicology. 2008; 82(5): 273-99.

Matoba, S, et al. p53 regulates mitochondrial respiration. Science (New York, NY). 2006; 312(5780): 1650-3.

McCord, JM, et al. Superoxide dismutase. An enzymic function for erythrocuprein (hemocuprein). The Journal of biological chemistry. 1969; 244(22): 6049-55.

Miriyala, S. et al. Manganese superoxide dismutase, MnSOD and its mimics, Biochimica et Biophysica Acta (BBA)—Molecular Basis of Disease. (2012), 1822(5):794-814.

Moeller, B., A manganese porphyrin superoxide dismutase mimetic enhances tumor radioresponsiveness, International Journal of Radiation Oncology, Biology. Physics, (2005), 63(2):545-552.

Morgan MJ, et al. Crosstalk of reactive oxygen species and NF-kappaB signaling. Cell Res. 2011; 21(1): 103-15.

Mufti A.R., et al., 2007. XIAP: cell death regulation meets copper homeostasis. Archives of biochemistry and biophysics 463. 168-174.

Mulay, I.L., et al., 1971. Trace-metal analysis of cancerous and noncancerous human tissues. Journal of the National Cancer Institute 47, 1-13.

Wang, W., et al., 2003. Disulfiram-mediated inhibition of NF-kappaB activity enhances cytotoxicity of 5-fluorouracil in human colorectal cancer cell lines. International journal of cancer. Journal international du cancer 104, 504-511.

Wang XJ, et al. Nrf2 enhances resistance of cancer cells to chemotherapeutic drugs, the dark side of Nrf2. Carcinogenesis. 2008; 29(6): 1235-43.

Wells PG, et al. Oxidative stress in developmental origins of disease: teratogenesis, neurodevelopmental deficits, and cancer. Toxicological sciences : an official journal of the Society of Toxicology. 2009; 108(1): 4-18.

Weydert CJ, et al. Overexpression of manganese or copper-zinc superoxide dismutase inhibits breast cancer growth. Free radical biology & medicine. 2006; 41(2): 226-37.

Whelan KA, et al. The Oncogene HER2/neu (ERBB2) Requires the Hypoxia-inducible Factor HIF-1 for Mammary Tumor Growth and Anoikis Resistance. The Journal of biological chemistry. 2013; 288(22): 15865-77.

Williams, K.P., et al., 2013. Quantitative high-throughput efficacy profiling of approved oncology drugs in inflammatory breast cancer models of acquired drug resistance and re-sensitization. Cancer letters 337, 77-89.

Williams KJ, et al. Hypoxia and oxidative stress. Tumour hypoxia—therapeutic considerations. Breast cancer research : BCR. 2001; 3(5): 328-31.

Wincewicz, A, et al. STAT3 and hypoxia induced proteins—HIF-1alpha, EPO and EPOR in relation with Bax and Bcl-xL in nodal metastases of ductal breast cancers. Folia histochemica et cytobiologica / Polish Academy of Sciences, Polish Histochemical and Cytochemical Society. 2009; 47(3): 425-30.

Winterbourn CC. Reconciling the chemistry and biology of reactive oxygen species. Nature chemical biology. 2008; 4(5): 278-86.

Xia W, et al. Resistance to ErbB2 tyrosine kinase inhibitors in breast cancer is mediated by calcium-dependent activation of RelA. Molecular cancer therapeutics. 2010; 9(2): 292-9.

Yagoda, N, et al. RAS-RAF-MEK-dependent oxidative cell death involving voltage-dependent anion channels. Nature. 2007; 447(7146): 864-8.

Yip, N.C., et al., 2011. Disulfiram modulated ROS-MAPK and NFkappaB pathways and targeted breast cancer cells with cancer stem cell-like properties. British journal of cancer 104, 1564-1574.

Yook Ji, et al. A Wnt-Axin2-GSK3beta cascade regulates Snail1 activity in breast cancer cells. Nature cell biology. 2006; 8(12): 1398-406.

Zhao Y, and Robbins D. Manganese superoxide dismutase in cancer prevention. Antioxidants & redox signaling. 2013.

Zhong H, et al. Overexpression of hypoxia-inducible factor 1alpha in common human cancers and their metastases. Cancer research. 1999; 59(22): 5830-5.

Zhong Y, et al. Drug resistance associates with activation of Nrf2 in MCF-7/DOX cells, and wogonin reverses it by down-regulating Nrf2-mediated cellular defense response. Molecular carcinogenesis. 2012; 16(10): 21921.

Zhou Y, et al. Enhanced NF kappa B and AP-1 transcriptional activity associated with antiestrogen resistant breast cancer. BMC Cancer. 2007; 7: 59.

Ziech D, et al. The role of reactive oxygen species and oxidative stress in environmental carcinogenesis and biomarker development. Chemico-biological interactions. 2010; 188(2): 334-9.

Ziech D, et al. Reactive oxygen species (ROS)—Induced genetic and epigenetic alterations in human carcinogenesis. Mutation research. 2011; 711(1-2): 167-73.

* cited by examiner

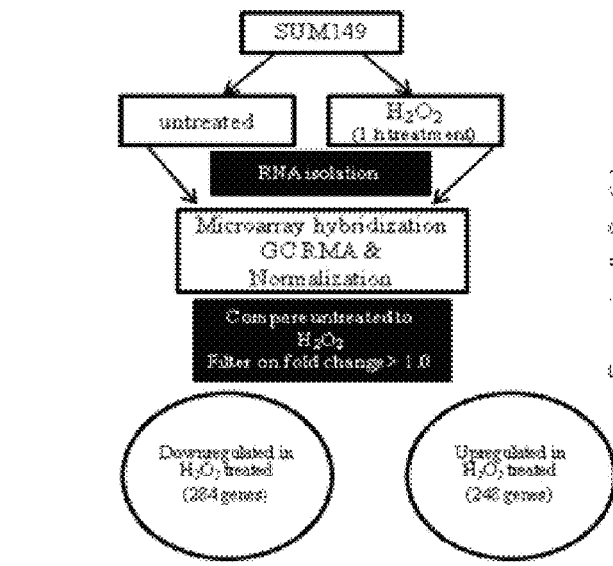
FIG. 1A
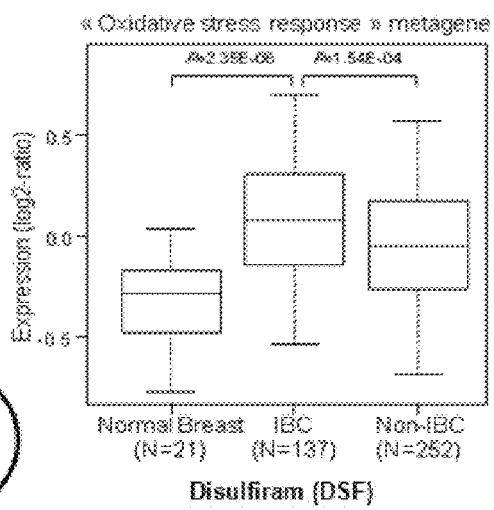
FIG. 1B
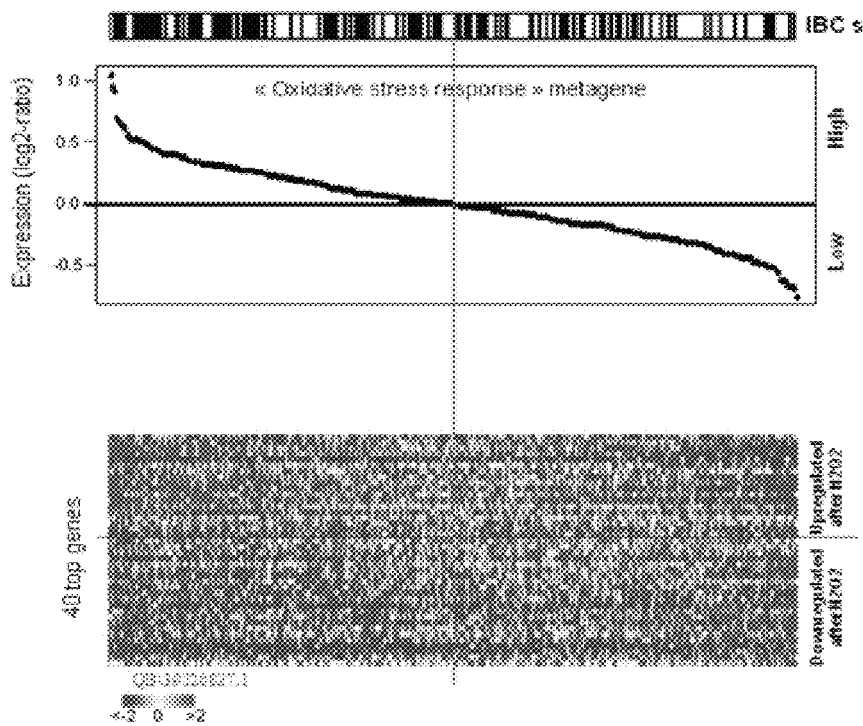
FIG. 1C
FIG. 1D

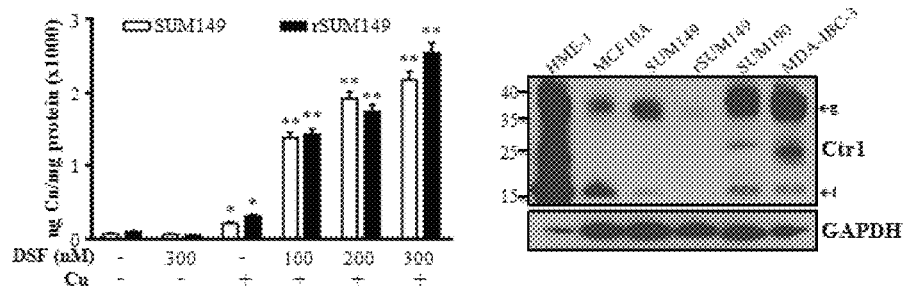
FIG. 4A
FIG. 4B
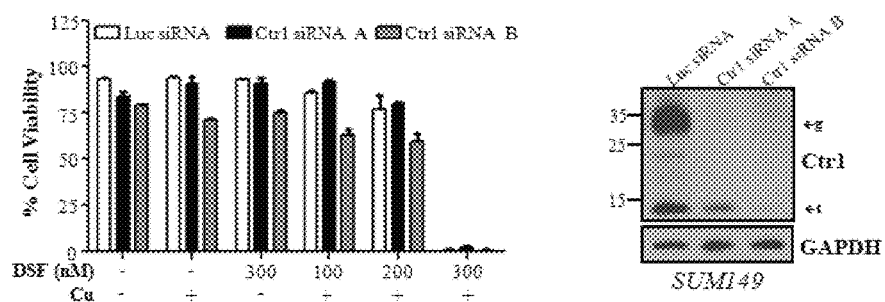
FIG. 4C
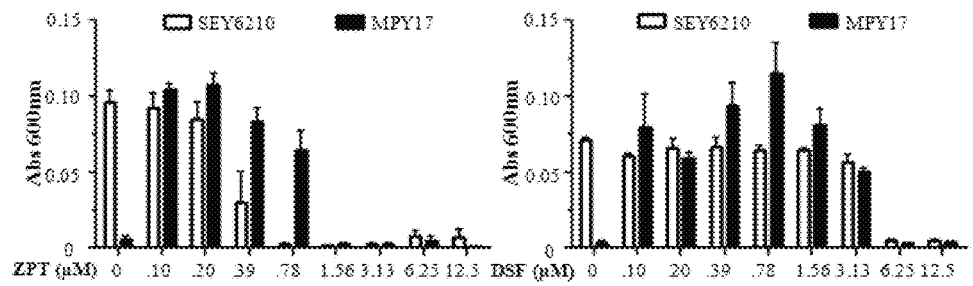
FIG. 4D

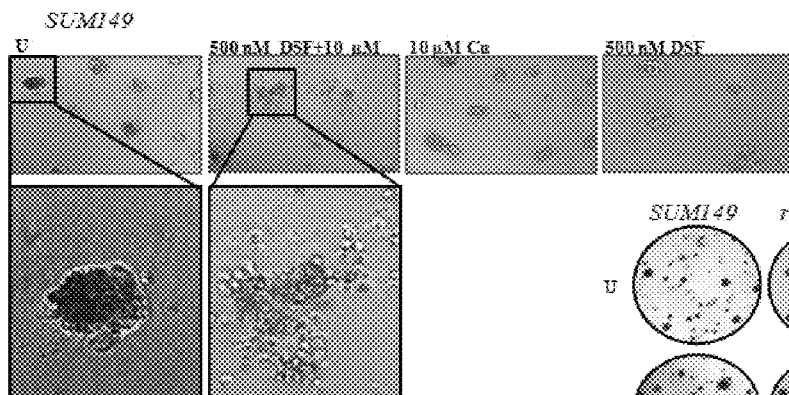
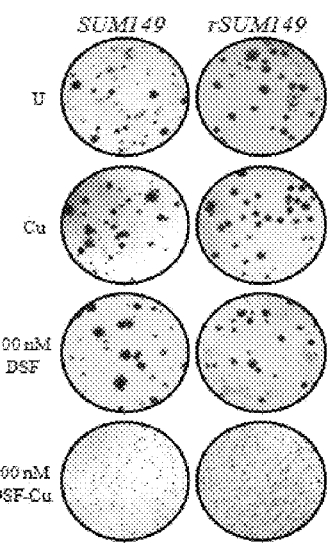
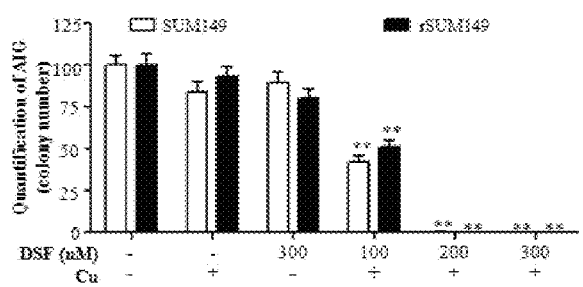
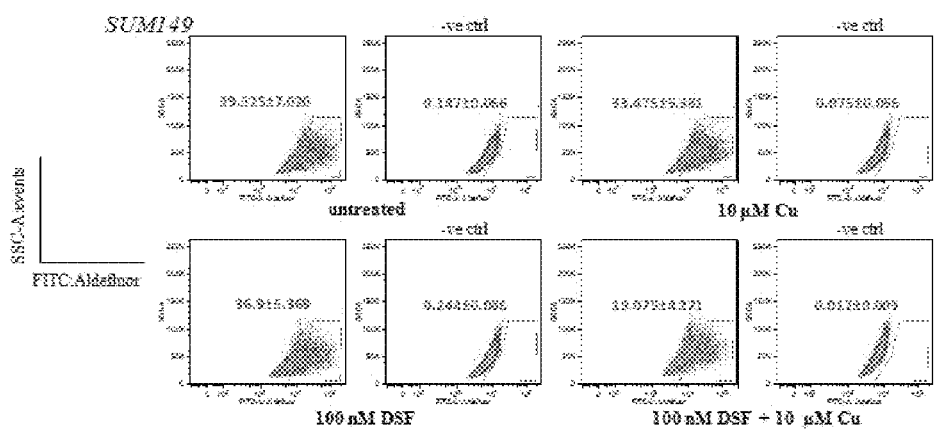

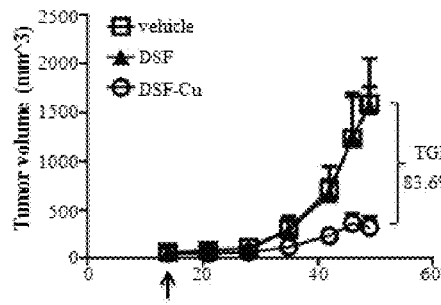
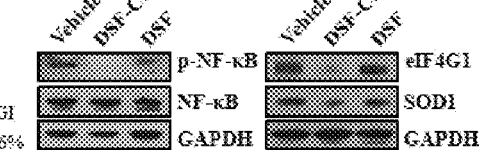
FIG. 6A
FIG. 6B
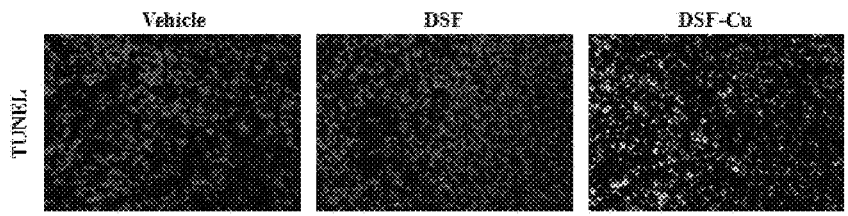
FIG. 6C
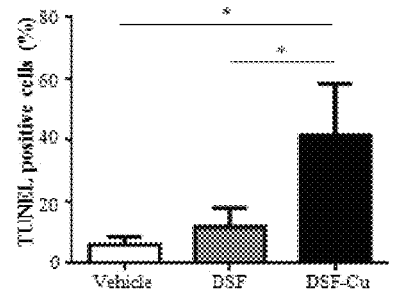
FIG. 6D
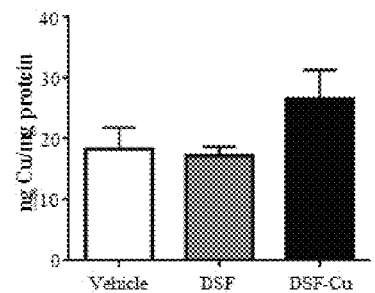
FIG. 6E
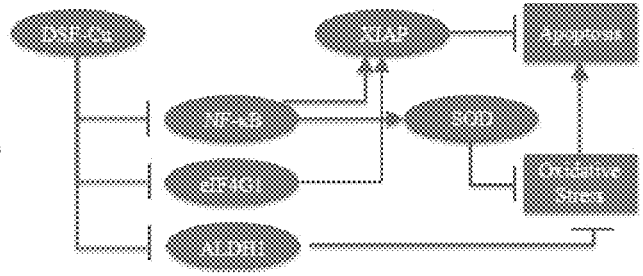
FIG. 6F

FIG. 9

| Antibody Name | Company | Catalog Number | Dilution |
|---|---|---|---|
| XIAP | BD Biosciences | 610672 | 1:2000 |
| SOD2 | BD Biosciences | 611580 | 1:1000 |
| SOD1 | Cell Signaling Tech. | 2770 | 1:1000 |
| PARP | Cell Signaling Tech. | 9532 | 1:1000 |
| eIF4G1 | Cell Signaling Tech. | 2469 | 1:1000 |
| $p$-p38 | Cell Signaling Tech. | 9211 | 1:1000 |
| p38 | Cell Signaling Tech. | 9212 | 1:1000 |
| $p$-NFκB (p65) | Cell Signaling Tech. | 3031 | 1:1000 |
| NFκB (p65) | Cell Signaling Tech. | 8242 | 1:1000 |
| $p$-ERK1/2 ($p$-p44/42) | Cell Signaling Tech. | 9101 | 1:1000 |
| ERK1/2 (p44/42) | Cell Signaling Tech. | 9102 | 1:1000 |
| GAPDH | Santa Cruz Biotechnology | 47724 | 1:4000 |
| p27/Kip1 | Cell Signaling Tech. | 3688 | 1:1000 |
| Ctrl | N/A | N/A | 1:1000 |

FIG. 10

List of 532 genes differentially expressed between treated with H2O2-treated and untreated SUM149 cell lines (p-value<5%, FDR<10%, FC>|2x|).

| Symbol | Gene Title | Chromosomal Location | Entrez Gene ID | Representative Public ID | UniGene ID | Fold-Change (log2) | Associated to |
|---|---|---|---|---|---|---|---|
| HSPA1A | heat shock 70kDa protein 1A | 6p21.3 | 3303 | NM_005345 | Hs.274402 | 3.41 | Upregulated in H2O2-treated SUM149 |
| METTL7A | methyltransferase like 7A | 12q13.12 | 25840 | NM_014033 | Hs.723867 | 2.84 | Upregulated in H2O2-treated SUM149 |
| BLM | Bloom syndrome, RecQ helicase-like | 15q26.1 | 641 | NM_000057 | Hs.169348 | 2.66 | Upregulated in H2O2-treated SUM149 |
| TYMS | thymidylate synthetase | 18p11.32 | 7298 | AB077208 | Hs.592338 | 2.56 | Upregulated in H2O2-treated SUM149 |
| KRT6B | keratin 6B | 12q12-q13 | 3854 | L42612 | Hs.708950 | 2.49 | Upregulated in H2O2-treated SUM149 |
| LIG1 | ligase I, DNA, ATP-dependent | 19q13.2-q13.3 | 3978 | NM_000234 | Hs.1770 | 2.40 | Upregulated in H2O2-treated SUM149 |
| SCD5 | stearoyl-CoA desaturase 5 | 4q21.22 | 79966 | NM_024906 | Hs.379191 | 2.34 | Upregulated in H2O2-treated SUM149 |
| POLE2 | polymerase (DNA directed), epsilon 2 (p59 subunit) | 14q21-q22 | 5427 | NM_002692 | Hs.162777 | 2.32 | Upregulated in H2O2-treated SUM149 |
| CDT1 | chromatin licensing and DNA replication factor 1 | 16q24.3 | 81620 | AF321125 | Hs.122908 | 2.27 | Upregulated in H2O2-treated SUM149 |
| CCNE2 | cyclin E2 | 8q22.1 | 9134 | NM_004702 | Hs.567387 | 2.24 | Upregulated in H2O2-treated SUM149 |
| SKP2 | S-phase kinase-associated protein 2 (p45) | 5p13 | 6502 | BG105365 | Hs.23348 | 2.24 | Upregulated in H2O2-treated SUM149 |
| E2F8 | E2F transcription factor 8 | 11p15.1 | 79733 | NM_024680 | Hs.523526 | 2.16 | Upregulated in H2O2-treated SUM149 |
| ORC1 | origin recognition complex, subunit 1 | 1p32 | 4998 | NM_004153 | Hs.17908 | 2.13 | Upregulated in H2O2-treated SUM149 |
| MCM4 | minichromosome maintenance complex component 4 | 8q11.2 | 4173 | AA604621 | Hs.460184 | 2.12 | Upregulated in H2O2-treated SUM149 |
| NOV | nephroblastoma overexpressed gene | 8q24.1 | 4856 | NM_002514 | Hs.235935 | 1.98 | Upregulated in H2O2-treated SUM149 |
| MUM1 | melanoma associated antigen (mutated) 1 | 19p13.3 | 84939 | NM_016473 | Hs.515016 | 1.96 | Upregulated in H2O2-treated SUM149 |
| MCM10 | minichromosome maintenance complex component 10 | 10p13 | 55388 | NM_018518 | Hs.198363 | 1.95 | Upregulated in H2O2-treated SUM149 |
| NAP1L3 | nucleosome assembly protein 1-like 3 | Xq21.3-q22 | 4675 | NM_004538 | Hs.21365 | 1.94 | Upregulated in H2O2-treated SUM149 |
| MCM3 | minichromosome maintenance complex component 3 | 6p12 | 4172 | NM_002388 | Hs.179565 | 1.89 | Upregulated in H2O2-treated SUM149 |
| ASF1B | ASF1 anti-silencing function 1 homolog B (S. cerevisiae) | 19p13.12 | 55723 | NM_018154 | Hs.26516 | 1.87 | Upregulated in H2O2-treated SUM149 |
| DSCC1 | defective in sister chromatid cohesion 1 homolog (S. cerevis-- | 8q24.12 | 79075 | L11372 | Hs.315167 | 1.85 | Upregulated in H2O2-treated SUM149 |
| FEN1 | flap structure-specific endonuclease 1 | 11q12 | 2237 | BC000323 | Hs.409065 | 1.83 | Upregulated in H2O2-treated SUM149 |
| TM4SF1 | transmembrane 4 L six family member 1 | 3q21-q25 | 4071 | AI346835 | Hs.723828 | 1.80 | Upregulated in H2O2-treated SUM149 |
| MCM7 | minichromosome maintenance complex component 7 | 7q21.3-q22.1 | 4176 | D55716 | Hs.438720 | 1.77 | Upregulated in H2O2-treated SUM149 |
| CDK1 | cyclin-dependent kinase 1 | 10q21.1 | 983 | AL524035 | Hs.334562 | 1.75 | Upregulated in H2O2-treated SUM149 |
| MCM6 | minichromosome maintenance complex | 2q21 | 4175 | NM_005915 | Hs.444118 | 1.75 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | component 6 | | | | | | |
| NAGPA | N-acetylglucosamine-1-phosphodiester alpha-N-acetylglucosami- | 16p13.3 | 51172 | NM_016256 | Hs.21334 | 1.73 | Upregulated in H2O2-treated SUM149 |
| ERCC6L | excision repair cross-complementing rodent repair deficiency- | Xq13.1 | 54821 | NM_017669 | Hs.47558 | 1.73 | Upregulated in H2O2-treated SUM149 |
| MSH2 | mutS homolog 2, colon cancer, nonpolyposis type 1 (E. coli) | 2p21 | 4436 | U04045 | Hs.597656 | 1.72 | Upregulated in H2O2-treated SUM149 |
| EIF2B3 | eukaryotic translation initiation factor 2B, subunit 3 gamma- | 1p34.1 | 8891 | NM_020365 | Hs.533549 | 1.70 | Upregulated in H2O2-treated SUM149 |
| GCA | grancalcin, EF-hand calcium binding protein | 2q24.2 | 25801 | NM_012198 | Hs.377894 | 1.70 | Upregulated in H2O2-treated SUM149 |
| DHFR | dihydrofolate reductase | 5q11.2-q13.2 | 1719 | BC000192 | Hs.648635 | 1.69 | Upregulated in H2O2-treated SUM149 |
| ABHD3 | abhydrolase domain containing 3 | 18q11.2 | 171586 | AL534702 | Hs.397978 | 1.69 | Upregulated in H2O2-treated SUM149 |
| LMO2 | LIM domain only 2 (rhombotin-like 1) | 11p13 | 4005 | NM_005574 | Hs.34560 | 1.68 | Upregulated in H2O2-treated SUM149 |
| IFI44L | interferon-induced protein 44-like | 1p31.1 | 10964 | NM_006820 | Hs.724492 | 1.67 | Upregulated in H2O2-treated SUM149 |
| ARHGDIB | Rho GDP dissociation inhibitor (GDI) beta | 12p12.3 | 397 | AF498927 | Hs.504877 | 1.66 | Upregulated in H2O2-treated SUM149 |
| MGST2 | microsomal glutathione S-transferase 2 | 4q28.3 | 4258 | NM_002413 | Hs.81874 | 1.64 | Upregulated in H2O2-treated SUM149 |
| GM2A | GM2 ganglioside activator | 5q33.1 | 2760 | M76477 | Hs.483873 | 1.64 | Upregulated in H2O2-treated SUM149 |
| SGK1 | serum/glucocorticoid regulated kinase 1 | 6q23 | 6446 | NM_005627 | Hs.510078 | 1.63 | Upregulated in H2O2-treated SUM149 |
| UBAP2L | ubiquitin associated protein 2-like | 1q21.3 | 9898 | NM_014847 | Hs.490551 | 1.61 | Upregulated in H2O2-treated SUM149 |
| HSPA8 | heat shock 70kDa protein 8 | 11q24.1 | 3312 | AF352832 | Hs.180414 | 1.61 | Upregulated in H2O2-treated SUM149 |
| AIM2 | absent in melanoma 2 | 1q22 | 9447 | NM_004833 | Hs.281898 | 1.61 | Upregulated in H2O2-treated SUM149 |
| MCM2 | minichromosome maintenance complex component 2 | 3q21 | 4171 | NM_004526 | Hs.477481 | 1.60 | Upregulated in H2O2-treated SUM149 |
| TACC3 | transforming, acidic coiled-coil containing protein 3 | 4p16.3 | 10460 | NM_006342 | Hs.104019 | 1.60 | Upregulated in H2O2-treated SUM149 |
| NQO1 | NAD(P)H dehydrogenase, quinone 1 | 16q22.1 | 1728 | AI039874 | Hs.406515 | 1.60 | Upregulated in H2O2-treated SUM149 |
| NAGK | N-acetylglucosamine kinase | 2p13.3 | 55577 | NM_017567 | Hs.7036 | 1.59 | Upregulated in H2O2-treated SUM149 |
| DDX19A | DEAD (Asp-Glu-Ala-As) box polypeptide 19A | 16q22.1 | 11269 | AL553254 | Hs.656037 | 1.58 | Upregulated in H2O2-treated SUM149 |
| RNASET2 | ribonuclease T2 | 6q27 | 8635 | AJ419867 | Hs.529989 | 1.55 | Upregulated in H2O2-treated SUM149 |
| LPCAT1 | lysophosphatidylcholine acyltransferase 1 | 5p15.33 | 79888 | NM_024830 | Hs.368853 | 1.55 | Upregulated in H2O2-treated SUM149 |
| GINS1 | GINS complex subunit 1 (Psf1 homolog) | 20p11.21 | 9837 | NM_021067 | Hs.658464 | 1.52 | Upregulated in H2O2-treated SUM149 |
| HJURP | Holliday junction recognition protein | 2q37.1 | 55355 | NM_018410 | Hs.532968 | 1.50 | Upregulated in H2O2-treated SUM149 |
| WRAP53 | WD repeat containing, antisense to TP53 | 17p13.1 | 55135 | NM_018081 | Hs.437460 | 1.50 | Upregulated in H2O2-treated SUM149 |
| BRCA1 | breast cancer 1, early onset | 17q21 | 672 | NM_007295 | Hs.194143 | 1.50 | Upregulated in H2O2-treated SUM149 |
| UNG | uracil-DNA glycosylase | 12q23-q24.1 | 7374 | NM_003362 | Hs.191334 | 1.49 | Upregulated in H2O2-treated SUM149 |
| C5orf13 | chromosome 5 open reading frame 13 | 5q22.1 | 9315 | U36189 | Hs.694860 | 1.49 | Upregulated in H2O2-treated SUM149 |
| SLC1A1 | solute carrier family 1 (neuronal/epithelial high affinity g- | 9p24 | 6505 | NM_004170 | Hs.444915 | 1.49 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| P4HA2 | prolyl 4-hydroxylase, alpha polypeptide II | 5q31 | 8974 | BC030525 | Hs.519568 | 1.49 | Upregulated in H2O2-treated SUM149 |
| RBL1 | retinoblastoma-like 1 (p107) | 20q11.2 | 5933 | BC032247 | Hs.207745 | 1.49 | Upregulated in H2O2-treated SUM149 |
| MCM5 | minichromosome maintenance complex component 5 | 22q13.1 | 4174 | NM_006739 | Hs.517582 | 1.48 | Upregulated in H2O2-treated SUM149 |
| AURKB | aurora kinase B | 17p13.1 | 9212 | AB011446 | Hs.442658 | 1.46 | Upregulated in H2O2-treated SUM149 |
| CD83 | CD83 molecule | 6p23 | 9308 | NM_004233 | Hs.595133 | 1.46 | Upregulated in H2O2-treated SUM149 |
| POLE | polymerase (DNA directed), epsilon | 12q24.3 | 5426 | AL080203 | Hs.524871 | 1.46 | Upregulated in H2O2-treated SUM149 |
| KIF22 | kinesin family member 22 | 16p11.2 | 3835 | NM_007317 | Hs.612151 | 1.45 | Upregulated in H2O2-treated SUM149 |
| GOT1 | glutamic-oxaloacetic transaminase 1, soluble (aspartate aminotransferase 1) | 10q24.1-q25.1 | 2805 | BC000498 | Hs.500756 | 1.44 | Upregulated in H2O2-treated SUM149 |
| NAT1 | N-acetyltransferase 1 (arylamine N-acetyltransferase) | 8p22 | 9 | NM_000662 | Hs.591847 | 1.44 | Upregulated in H2O2-treated SUM149 |
| FANCG | Fanconi anemia, complementation group G | 9p13 | 2189 | NM_004629 | Hs.591084 | 1.44 | Upregulated in H2O2-treated SUM149 |
| VCL | vinculin | 10q22.2 | 7414 | AA156675 | Hs.643896 | 1.43 | Upregulated in H2O2-treated SUM149 |
| IFI30 | interferon, gamma-inducible protein 30 | 19p13.1 | 10437 | NM_006332 | Hs.14623 | 1.43 | Upregulated in H2O2-treated SUM149 |
| ZC3HAV1 | zinc finger CCCH-type, antiviral 1 | 7q34 | 56829 | AI133727 | Hs.133512 | 1.43 | Upregulated in H2O2-treated SUM149 |
| PAQR4 | progestin and adipoQ receptor family member IV | 16p13.3 | 124222 | AL520675 | Hs.351474 | 1.43 | Upregulated in H2O2-treated SUM149 |
| SUV39H1 | suppressor of variegation 3-9 homolog 1 (Drosophila) | Xp11.23 | 6839 | NM_003173 | Hs.522639 | 1.42 | Upregulated in H2O2-treated SUM149 |
| DNA2 | DNA replication helicase 2 homolog (yeast) | 10q21.3-q22.1 | 1763 | D42046 | Hs.532446 | 1.42 | Upregulated in H2O2-treated SUM149 |
| TMEM97 | transmembrane protein 97 | 17q11.2 | 27346 | BE779865 | Hs.199695 | 1.41 | Upregulated in H2O2-treated SUM149 |
| CDC25A | cell division cycle 25 homolog A (S. pombe) | 3p21 | 993 | AY137580 | Hs.437705 | 1.41 | Upregulated in H2O2-treated SUM149 |
| NRIP3 | nuclear receptor interacting protein 3 | 11p15.3 | 56675 | NM_020645 | Hs.523467 | 1.41 | Upregulated in H2O2-treated SUM149 |
| ACOX2 | acyl-CoA oxidase 2, branched chain | 3p14.3 | 8309 | NM_003500 | Hs.444959 | 1.40 | Upregulated in H2O2-treated SUM149 |
| DNAJA1 | DnaJ (Hsp40) homolog, subfamily A, member 1 | 9p13.3 | 3301 | AL534104 | Hs.445203 | 1.40 | Upregulated in H2O2-treated SUM149 |
| MCAM | melanoma cell adhesion molecule | 11q23.3 | 4162 | BE964361 | Hs.599039 | 1.38 | Upregulated in H2O2-treated SUM149 |
| PMP22 | peripheral myelin protein 22 | 17p12 | 5376 | L03203 | Hs.372031 | 1.38 | Upregulated in H2O2-treated SUM149 |
| FRY | furry homolog (Drosophila) | 13q13.1 | 10129 | NM_023037 | Hs.507669 | 1.38 | Upregulated in H2O2-treated SUM149 |
| B3GNT1 | UDP-GlcNAc:betaGal beta-1,3-N-acetylglucosaminyltransferase | 11q13.2 | 11041 | NM_006876 | Hs.8526 | 1.38 | Upregulated in H2O2-treated SUM149 |
| FAM172A | family with sequence similarity 172, member A | 5q15 | 83989 | AI927701 | Hs.600086 | 1.37 | Upregulated in H2O2-treated SUM149 |
| DRG1 | developmentally regulated GTP binding protein 1 | 22q12.2 | 4733 | NM_004147 | Hs.115242 | 1.37 | Upregulated in H2O2-treated SUM149 |
| C3orf14 | chromosome 3 open reading frame 14 | 3p14.2 | 57415 | NM_020685 | Hs.47166 | 1.37 | Upregulated in H2O2-treated SUM149 |
| HMOX2 | heme oxygenase (decycling) 2 | 16p13.3 | 3163 | D21243 | Hs.284279 | 1.37 | Upregulated in H2O2-treated SUM149 |
| CLEC2B | C-type lectin domain family 2, member B | 12p13-p12 | 9976 | CA447397 | Hs.85201 | 1.36 | Upregulated in H2O2-treated SUM149 |
| SRRT | serrate RNA effector molecule homolog | 7q21 | 51593 | BE646076 | Hs.111801 | 1.36 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | (Arabidopsis) | | | | | | |
| ABHD11 | abhydrolase domain containing 11 | 7q11.23 | 83451 | NM_148914 | Hs.647045 | 1.36 | Upregulated in H2O2-treated SUM149 |
| EGR1 | early growth response 1 | 5q31.1 | 1958 | AV733950 | Hs.326035 | 1.35 | Upregulated in H2O2-treated SUM149 |
| FHOD1 | formin homology 2 domain containing 1 | 16q22 | 29109 | NM_013241 | Hs.95231 | 1.35 | Upregulated in H2O2-treated SUM149 |
| AKR1C2 | Aldo-keto reductase family 1 member C2 (dihydrodiol dehydro-- | 10p15-p14 | 1646 | CA425039 | Hs.567256 | 1.34 | Upregulated in H2O2-treated SUM149 |
| TACO1 | translational activator of mitochondrially encoded cytochrom-- | 17q23.3 | 51204 | NM_016360 | Hs.174134 | 1.34 | Upregulated in H2O2-treated SUM149 |
| CXorf57 | chromosome X open reading frame 57 | Xq22.3 | 55086 | AK001040 | Hs.274267 | 1.34 | Upregulated in H2O2-treated SUM149 |
| IDH2 | isocitrate dehydrogenase 2 (NADP+), mitochondrial | 15q26.1 | 3418 | AU151428 | Hs.596461 | 1.34 | Upregulated in H2O2-treated SUM149 |
| C1GALT1C1 | C1GALT1-specific chaperone 1 | Xq24 | 29071 | NM_014158 | Hs.643920 | 1.34 | Upregulated in H2O2-treated SUM149 |
| TK1 | thymidine kinase 1, soluble | 17q23.2-q25.3 | 7083 | BC007986 | Hs.515122 | 1.33 | Upregulated in H2O2-treated SUM149 |
| IFI44 | interferon-induced protein 44 | 1p31.1 | 10561 | BE049439 | Hs.82316 | 1.33 | Upregulated in H2O2-treated SUM149 |
| KIF20A | kinesin family member 20A | 5q31 | 10112 | NM_005733 | Hs.718626 | 1.33 | Upregulated in H2O2-treated SUM149 |
| AKR1C1 | aldo-keto reductase family 1, member C1 (dihydrodiol dehydro-- | 10p15-p14 | 1645 | AA594609 | Hs.567256 | 1.32 | Upregulated in H2O2-treated SUM149 |
| NUP85 | nucleoporin 85kDa | 17q25.1 | 79902 | NM_024844 | Hs.362817 | 1.32 | Upregulated in H2O2-treated SUM149 |
| VAMP1 | vesicle-associated membrane protein 1 (synaptobrevin 1) | 12p | 6843 | NM_016830 | Hs.20021 | 1.32 | Upregulated in H2O2-treated SUM149 |
| RNF8 | ring finger protein 8 | 6p21.3 | 9025 | AK022075 | Hs.485278 | 1.31 | Upregulated in H2O2-treated SUM149 |
| POLA2 | polymerase (DNA directed), alpha 2 (70kD subunit) | 11q13.1 | 23649 | NM_002689 | Hs.201897 | 1.31 | Upregulated in H2O2-treated SUM149 |
| POLA1 | polymerase (DNA directed), alpha 1, catalytic subunit | Xp22.1-p21.3 | 5422 | NM_016937 | Hs.567319 | 1.30 | Upregulated in H2O2-treated SUM149 |
| CSTF2 | cleavage stimulation factor, 3 pre-RNA, subunit 2, 64kDa | Xq22.1 | 1478 | NM_001325 | Hs.132370 | 1.30 | Upregulated in H2O2-treated SUM149 |
| RPS6KA1 | ribosomal protein S6 kinase, 90kDa, polypeptide 1 | 1p | 6195 | NM_002953 | Hs.149957 | 1.29 | Upregulated in H2O2-treated SUM149 |
| CDC5L | CDC5 cell division cycle 5-like (S. pombe) | 6p21 | 988 | AW268817 | Hs.485471 | 1.29 | Upregulated in H2O2-treated SUM149 |
| TMEM48 | transmembrane protein 48 | 1p32.3 | 55706 | NM_018087 | Hs.476525 | 1.29 | Upregulated in H2O2-treated SUM149 |
| OAS3 | 2'-5'-oligoadenylate synthetase 3, 100kDa | 12q24.2 | 4940 | NM_006187 | Hs.528634 | 1.29 | Upregulated in H2O2-treated SUM149 |
| ABCC5 | ATP-binding cassette, sub-family C (CFTR/MRP), member 5 | 3q27 | 10057 | AL707614 | Hs.368563 | 1.29 | Upregulated in H2O2-treated SUM149 |
| SNRNP25 | small nuclear ribonucleoprotein 25kDa (U11/U12) | 16p13.3 | 79622 | NM_024571 | Hs.15277 | 1.28 | Upregulated in H2O2-treated SUM149 |
| PLAUR | plasminogen activator, urokinase receptor | 19q13 | 5329 | U08839 | Hs.466871 | 1.28 | Upregulated in H2O2-treated SUM149 |
| EXO1 | exonuclease 1 | 1q42-q43 | 9156 | NM_003686 | Hs.498248 | 1.28 | Upregulated in H2O2-treated SUM149 |
| HSP90AA1 | heat shock protein 90kDa alpha (cytosolic), class A member 1 | 14q32.33 | 3320 | AF028832 | Hs.525600 | 1.28 | Upregulated in H2O2-treated SUM149 |
| CTDSPL | CTD (carboxy-terminal domain, RNA polymerase II, polypeptide-- | 3p21.3 | 10217 | BF031714 | Hs.475963 | 1.28 | Upregulated in H2O2-treated SUM149 |
| PCNA | proliferating cell nuclear antigen | 20pter-p12 | 5111 | NM_002592 | Hs.147433 | 1.28 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| CDK2 | cyclin-dependent kinase 2 | 12q13 | 1017 | M68520 | Hs.19192 | 1.28 | Upregulated in H2O2-treated SUM149 |
| HLTF | helicase-like transcription factor | 3q25.1-q26.1 | 6596 | AI760760 | Hs.3068 | 1.27 | Upregulated in H2O2-treated SUM149 |
| RAD54B | RAD54 homolog B (S. cerevisiae) | 8q22.1 | 25788 | NM_012415 | Hs.30561 | 1.27 | Upregulated in H2O2-treated SUM149 |
| POP7 | processing of precursor 7, ribonuclease P/MRP subunit (S. ce- | 7q22 | 10248 | BC001430 | Hs.416994 | 1.27 | Upregulated in H2O2-treated SUM149 |
| H2AFX | H2A histone family, member X | 11q23.3 | 3014 | NM_002105 | Hs.477879 | 1.27 | Upregulated in H2O2-treated SUM149 |
| LAGE3 | L antigen family, member 3 | Xq28 | 8270 | NM_006014 | Hs.444619 | 1.27 | Upregulated in H2O2-treated SUM149 |
| MAT2A | methionine adenosyltransferase II, alpha | 2p11.2 | 4144 | BC001686 | Hs.516157 | 1.26 | Upregulated in H2O2-treated SUM149 |
| HSPA14 | heat shock 70kDa protein 14 | 10p13 | 51182 | NM_016299 | Hs.534169 | 1.26 | Upregulated in H2O2-treated SUM149 |
| RAD54L | RAD54-like (S. cerevisiae) | 1p32 | 8438 | NM_003579 | Hs.642042 | 1.26 | Upregulated in H2O2-treated SUM149 |
| LY96 | lymphocyte antigen 96 | 8q21.11 | 23643 | NM_015364 | Hs.660766 | 1.26 | Upregulated in H2O2-treated SUM149 |
| TCTN2 | tectonic family member 2 | 12q24.31 | 79867 | NM_024809 | Hs.167165 | 1.26 | Upregulated in H2O2-treated SUM149 |
| TUBB | tubulin, beta | 6p21.33 | 203068 | AF141349 | Hs.636480 | 1.26 | Upregulated in H2O2-treated SUM149 |
| ZCCHC24 | zinc finger, CCHC domain containing 24 | 10q22.3 | 219654 | AA331324 | Hs.523080 | 1.25 | Upregulated in H2O2-treated SUM149 |
| NSDHL | NAD(P) dependent steroid dehydrogenase-like | Xq28 | 50814 | BC000245 | Hs.57698 | 1.25 | Upregulated in H2O2-treated SUM149 |
| RAD51 | RAD51 homolog (RecA homolog, E. coli) (S. cerevisiae) | 15q15.1 | 5888 | D14134 | Hs.631709 | 1.25 | Upregulated in H2O2-treated SUM149 |
| SPR | sepiapterin reductase (7,8-dihydrobiopterin:NADP+ oxidoredoc- | 2p14-p12 | 6697 | AJ951454 | Hs.301540 | 1.25 | Upregulated in H2O2-treated SUM149 |
| NTHL1 | nth endonuclease III-like 1 (E. coli) | 16p13.3 | 4913 | U79718 | Hs.66196 | 1.24 | Upregulated in H2O2-treated SUM149 |
| KEAP1 | kelch-like ECH-associated protein 1 | 19p13.2 | 9817 | NM_012289 | Hs.465870 | 1.24 | Upregulated in H2O2-treated SUM149 |
| AKR1C3 | aldo-keto reductase family 1, member C3 (3-alpha hydroxyster- | 10p15-p14 | 8644 | AB018580 | Hs.78183 | 1.24 | Upregulated in H2O2-treated SUM149 |
| RECQL4 | RecQ protein-like 4 | 8q24.3 | 9401 | NM_004260 | Hs.31442 | 1.24 | Upregulated in H2O2-treated SUM149 |
| DFFB | DNA fragmentation factor, 40kDa, beta polypeptide (caspase-a- | 1p36.3 | 1677 | NM_004402 | Hs.133089 | 1.23 | Upregulated in H2O2-treated SUM149 |
| SMCR7L | Smith-Magenis syndrome chromosome region, candidate 7-like | 22q13 | 54471 | AA046752 | Hs.148677 | 1.23 | Upregulated in H2O2-treated SUM149 |
| PGD | phosphogluconate dehydrogenase | 1p36.22 | 5226 | NM_002631 | Hs.464071 | 1.23 | Upregulated in H2O2-treated SUM149 |
| CUTC | cutC copper transporter homolog (E. coli) | 10q24.2 | 51076 | NM_015960 | Hs.16606 | 1.22 | Upregulated in H2O2-treated SUM149 |
| ETFB | electron-transfer-flavoprotein, beta polypeptide | 19q13.3 | 2109 | NM_001985 | Hs.348531 | 1.22 | Upregulated in H2O2-treated SUM149 |
| ZNF107 | zinc finger protein 107 | 7q11.2 | 51427 | BC017809 | Hs.50216 | 1.21 | Upregulated in H2O2-treated SUM149 |
| DLGAP5 | discs, large (Drosophila) homolog-associated protein 5 | 14q22.3 | 9787 | NM_014750 | Hs.77695 | 1.21 | Upregulated in H2O2-treated SUM149 |
| PLAU | plasminogen activator, urokinase | 10q24 | 5328 | NM_002658 | Hs.77274 | 1.21 | Upregulated in H2O2-treated SUM149 |
| C14orf1 | chromosome 14 open reading frame 1 | 14q24.3 | 11161 | AL136658 | Hs.15106 | 1.20 | Upregulated in H2O2-treated SUM149 |
| TUBB2C | tubulin, beta 2C | 9q34 | 10383 | BC004188 | Hs.433615 | 1.20 | Upregulated in H2O2-treated SUM149 |
| ADA | adenosine deaminase | 20q13.12 | 100 | NM_000022 | Hs.654536 | 1.20 | Upregulated in H2O2-treated |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| ADCK3 | aarF domain containing kinase 3 | 1q42.13 | 56997 | NM_020247 | Hs.118241 | 1.20 | Upregulated in H2O2-treated SUM149 |
| FABP5 | fatty acid binding protein 5 (psoriasis-associated) | 8q21.13 | 2171 | NM_001444 | Hs.408061 | 1.20 | Upregulated in H2O2-treated SUM149 |
| CENPI | centromere protein I | Xq22.1 | 2491 | BC012462 | Hs.318398 | 1.20 | Upregulated in H2O2-treated SUM149 |
| PNP | purine nucleoside phosphorylase | 14q13.1 | 4860 | NM_000270 | Hs.75514 | 1.19 | Upregulated in H2O2-treated SUM149 |
| ALG9 | asparagine-linked glycosylation 9, alpha-1,2-mannosyltransfe- | 11q23 | 79796 | NM_024740 | Hs.697132 | 1.18 | Upregulated in H2O2-treated SUM149 |
| GMPPA | GDP-mannose pyrophosphorylase A | 2q35 | 29926 | NM_013335 | Hs.27059 | 1.18 | Upregulated in H2O2-treated SUM149 |
| OPHN1 | oligophrenin 1 | Xq12 | 4983 | NM_002547 | Hs.128824 | 1.18 | Upregulated in H2O2-treated SUM149 |
| ANGPTL4 | angiopoietin-like 4 | 19p13.3 | 51129 | NM_016109 | Hs.9613 | 1.18 | Upregulated in H2O2-treated SUM149 |
| ALAS1 | aminolevulinate, delta-, synthase 1 | 3p21.1 | 211 | NM_000688 | Hs.476308 | 1.18 | Upregulated in H2O2-treated SUM149 |
| BTN3A2 | butyrophilin, subfamily 3, member A2 | 6p21.3 | 10384 | NM_006994 | Hs.167741 | 1.17 | Upregulated in H2O2-treated SUM149 |
| SPC25 | SPC25, NDC80 kinetochore complex component, homolog (S. cere- | 2q31.1 | 57405 | AF225416 | Hs.421956 | 1.17 | Upregulated in H2O2-treated SUM149 |
| POLQ | polymerase (DNA directed), theta | 3q13.33 | 10721 | NM_014125 | Hs.241517 | 1.17 | Upregulated in H2O2-treated SUM149 |
| FAM64A | family with sequence similarity 64, member A | 17p13.2 | 54478 | BC005004 | Hs.592116 | 1.17 | Upregulated in H2O2-treated SUM149 |
| S100A4 | S100 calcium binding protein A4 | 1q21 | 6275 | NM_002961 | Hs.654444 | 1.17 | Upregulated in H2O2-treated SUM149 |
| RFC3 | replication factor C (activator 1) 3, 38kDa | 13q13.2 | 5983 | BC000149 | Hs.115474 | 1.17 | Upregulated in H2O2-treated SUM149 |
| NDUFS3 | NADH dehydrogenase (ubiquinone) Fe-S protein 3, 30kDa (NADH- | 11p11.11 | 4722 | NM_004551 | Hs.502528 | 1.16 | Upregulated in H2O2-treated SUM149 |
| PCYOX1 | prenylcysteine oxidase 1 | 2p13.3 | 51449 | N45309 | Hs.567502 | 1.16 | Upregulated in H2O2-treated SUM149 |
| ABHD14A | abhydrolase domain containing 14A | 3p21.1 | 25864 | NM_000666 | Hs.334707 | 1.15 | Upregulated in H2O2-treated SUM149 |
| FGFR1OP | FGFR1 oncogene partner | 6q27 | 11116 | BC037785 | Hs.487175 | 1.15 | Upregulated in H2O2-treated SUM149 |
| TNFAIP3 | tumor necrosis factor, alpha-induced protein 3 | 6q23 | 7128 | AI738896 | Hs.211600 | 1.15 | Upregulated in H2O2-treated SUM149 |
| NCAPG | non-SMC condensin I complex, subunit G | 4p15.33 | 64151 | NM_022346 | Hs.567567 | 1.15 | Upregulated in H2O2-treated SUM149 |
| C1orf216 | chromosome 1 open reading frame 216 | 1p34.3 | 127703 | AL042729 | Hs.112023 | 1.15 | Upregulated in H2O2-treated SUM149 |
| BUB1B | budding uninhibited by benzimidazoles 1 homolog beta (yeast) | 15q15 | 701 | NM_001211 | Hs.513645 | 1.14 | Upregulated in H2O2-treated SUM149 |
| RAB40B | RAB40B, member RAS oncogene family | 17q25.3 | 10966 | NM_006822 | Hs.484068 | 1.14 | Upregulated in H2O2-treated SUM149 |
| CRYBG3 | beta-gamma crystallin domain containing 3 | 3q11.2 | 131544 | BE501352 | Hs.714457 | 1.14 | Upregulated in H2O2-treated SUM149 |
| POP1 | processing of precursor 1, ribonuclease P/MRP subunit (S. ce- | 8q22.1 | 10940 | D31765 | Hs.252828 | 1.14 | Upregulated in H2O2-treated SUM149 |
| TUBB3 | tubulin, beta 3 | 16q24.3 | 10381 | NM_006086 | Hs.511743 | 1.14 | Upregulated in H2O2-treated SUM149 |
| ACYP1 | acylphosphatase 1, erythrocyte (common) type | 14q24.3 | 97 | NM_001107 | Hs.18573 | 1.14 | Upregulated in H2O2-treated SUM149 |
| CBR1 | carbonyl reductase 1 | 21q22.13 | 873 | BC002511 | Hs.88778 | 1.13 | Upregulated in H2O2-treated SUM149 |
| MNS1 | meiosis-specific nuclear structural 1 | 15q21.3 | 55329 | NM_018365 | Hs.444483 | 1.13 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| SH3GL3 | SH3-domain GRB2-like 3 | 15q24 | 6457 | AF036269 | --- | 1.13 | Upregulated in H2O2-treated SUM149 |
| VAV3 | vav 3 guanine nucleotide exchange factor | 1p13.3 | 10451 | AF118887 | Hs.267659 | 1.13 | Upregulated in H2O2-treated SUM149 |
| CDC45 | cell division cycle 45 homolog (S. cerevisiae) | 22q11.21 | 8318 | NM_003504 | Hs.474217 | 1.13 | Upregulated in H2O2-treated SUM149 |
| NFS1 | NFS1 nitrogen fixation 1 homolog (S. cerevisiae) | 20q11.22 | 9054 | BC018471 | Hs.194692 | 1.13 | Upregulated in H2O2-treated SUM149 |
| ILF2 | interleukin enhancer binding factor 2, 45kDa | 1q21.3 | 3608 | NM_004515 | Hs.75117 | 1.13 | Upregulated in H2O2-treated SUM149 |
| POR | P450 (cytochrome) oxidoreductase | 7q11.2 | 5447 | AF258341 | Hs.354056 | 1.12 | Upregulated in H2O2-treated SUM149 |
| DDX23 | DEAD (Asp-Glu-Ala-Asp) box polypeptide 23 | 12q13.12 | 9416 | NM_004818 | Hs.130098 | 1.12 | Upregulated in H2O2-treated SUM149 |
| AK2 | adenylate kinase 2 | 1p34 | 204 | NM_013411 | Hs.470907 | 1.12 | Upregulated in H2O2-treated SUM149 |
| POLD3 | polymerase (DNA-directed), delta 3, accessory subunit | 11q14 | 10714 | D26018 | Hs.82502 | 1.12 | Upregulated in H2O2-treated SUM149 |
| TCP1 | t-complex 1 | 6q25.3-q26 | 6950 | BC000665 | Hs.363137 | 1.12 | Upregulated in H2O2-treated SUM149 |
| TUBB2A | tubulin, beta 2A | 6p25 | 7280 | NM_001069 | Hs.654543 | 1.11 | Upregulated in H2O2-treated SUM149 |
| SLC48A1 | solute carrier family 48 (heme transporter), member 1 | 12q13.11 | 55652 | AW149696 | Hs.438867 | 1.11 | Upregulated in H2O2-treated SUM149 |
| NUP188 | nucleoporin 188kDa | 9q34.11 | 23511 | AW131863 | Hs.308340 | 1.11 | Upregulated in H2O2-treated SUM149 |
| TBC1D1 | TBC1 (tre-2/USP6, BUB2, cdc16) domain family, member 1 | 4p14 | 23216 | AI872403 | Hs.176503 | 1.11 | Upregulated in H2O2-treated SUM149 |
| CBARA1 | calcium binding atopy-related autoantigen 1 | 10q22.1 | 10367 | AK022697 | Hs.524367 | 1.10 | Upregulated in H2O2-treated SUM149 |
| PI3 | peptidase inhibitor 3, skin-derived | 20q13.12 | 5266 | NM_002638 | Hs.112341 | 1.10 | Upregulated in H2O2-treated SUM149 |
| BARD1 | BRCA1 associated RING domain 1 | 2q34-q35 | 580 | NM_000465 | Hs.591642 | 1.10 | Upregulated in H2O2-treated SUM149 |
| NEIL3 | nei endonuclease VIII-like 3 (E. coli) | 4q34.3 | 55247 | NM_018248 | Hs.405467 | 1.10 | Upregulated in H2O2-treated SUM149 |
| NBL1 | neuroblastoma, suppression of tumorigenicity 1 | 1p36.13 | 4681 | NM_005380 | Hs.654502 | 1.10 | Upregulated in H2O2-treated SUM149 |
| BCAT2 | branched chain amino-acid transaminase 2, mitochondrial | 19q13 | 587 | NM_001190 | Hs.512670 | 1.10 | Upregulated in H2O2-treated SUM149 |
| LPAR6 | lysophosphatidic acid receptor 6 | 13q14 | 10161 | BC039373 | Hs.123464 | 1.09 | Upregulated in H2O2-treated SUM149 |
| HCCS | holocytochrome c synthase | Xp22.3 | 3052 | AI801013 | Hs.211571 | 1.09 | Upregulated in H2O2-treated SUM149 |
| MLF1IP | MLF1 interacting protein | 4q35.1 | 79682 | NM_024629 | Hs.575032 | 1.09 | Upregulated in H2O2-treated SUM149 |
| PML | promyelocytic leukemia | 15q22 | 5371 | NM_002675 | Hs.526464 | 1.09 | Upregulated in H2O2-treated SUM149 |
| SMARCC2 | SWI/SNF related, matrix associated, actin dependent regulato- | 12q13.2 | 6601 | AL833124 | Hs.236030 | 1.09 | Upregulated in H2O2-treated SUM149 |
| ESPL1 | extra spindle pole bodies homolog 1 (S. cerevisiae) | 12q | 9700 | NM_012291 | Hs.153479 | 1.08 | Upregulated in H2O2-treated SUM149 |
| KRT6A | keratin 6A | 12q12-q13 | 3853 | J00269 | Hs.700779 | 1.08 | Upregulated in H2O2-treated SUM149 |
| CDCA8 | cell division cycle associated 8 | 1p34.3 | 55143 | BC001651 | Hs.524571 | 1.08 | Upregulated in H2O2-treated SUM149 |
| TUBA4A | tubulin, alpha 4a | 2q35 | 7277 | AL565074 | Hs.75318 | 1.08 | Upregulated in H2O2-treated SUM149 |
| MAP3K5 | mitogen-activated protein kinase kinase kinase 5 | 6q22.33 | 4217 | D84476 | Hs.186486 | 1.08 | Upregulated in H2O2-treated SUM149 |
| CD59 | CD59 molecule, complement regulatory protein | 11p13 | 966 | BF983379 | Hs.709466 | 1.08 | Upregulated in H2O2-treated SUM149 |
| SPHK1 | sphingosine kinase 1 | 17q25.2 | 8877 | NM_021972 | Hs.68061 | 1.07 | Upregulated in H2O2-treated SUM149 |
| HDAC1 | histone deacetylase 1 | 1p34 | 3065 | NM_004964 | Hs.88556 | 1.07 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | | | | | | | SUM149 |
| ANKMY2 | ankyrin repeat and MYND domain containing 2 | 7p21 | 57037 | AK001389 | Hs.157378 | 1.07 | Upregulated in H2O2-treated SUM149 |
| STIP1 | stress-induced-phosphoprotein 1 | 11q13 | 10963 | AL553320 | Hs.337295 | 1.07 | Upregulated in H2O2-treated SUM149 |
| ICMT | isoprenylcysteine carboxyl methyltransferase | 1p36.21 | 23463 | AL578502 | Hs.515688 | 1.06 | Upregulated in H2O2-treated SUM149 |
| SLC25A11 | solute carrier family 25 (mitochondrial carrier; oxoglutarat- | 17p13.3 | 8402 | NM_003562 | Hs.184877 | 1.06 | Upregulated in H2O2-treated SUM149 |
| RECK | reversion-inducing-cysteine-rich protein with kazal motif | 9p13.3 | 8434 | BC032240 | Hs.388918 | 1.06 | Upregulated in H2O2-treated SUM149 |
| BTD | biotinidase | 3p25 | 686 | NM_000060 | Hs.517830 | 1.05 | Upregulated in H2O2-treated SUM149 |
| LMNB1 | lamin B1 | 5q23.2 | 4001 | NM_005573 | Hs.89497 | 1.05 | Upregulated in H2O2-treated SUM149 |
| RRM2 | ribonucleotide reductase M2 | 2p25-p24 | 6241 | BE966236 | Hs.226390 | 1.05 | Upregulated in H2O2-treated SUM149 |
| CERK | ceramide kinase | 22q13.31 | 64781 | NM_022766 | Hs.200668 | 1.04 | Upregulated in H2O2-treated SUM149 |
| CCDC28B | coiled-coil domain containing 28B | 1p35.1 | 79140 | NM_024296 | Hs.724544 | 1.04 | Upregulated in H2O2-treated SUM149 |
| DNAJB1 | DnaJ (Hsp40) homolog, subfamily B, member 1 | 19p13.2 | 3337 | BG537255 | Hs.515210 | 1.04 | Upregulated in H2O2-treated SUM149 |
| PARP2 | poly (ADP-ribose) polymerase 2 | 14q11.2-q12 | 10038 | NM_005484 | Hs.409412 | 1.04 | Upregulated in H2O2-treated SUM149 |
| ICAM3 | intercellular adhesion molecule 3 | 19p13.3-p13.2 | 3385 | NM_002162 | Hs.654563 | 1.04 | Upregulated in H2O2-treated SUM149 |
| OBSL1 | obscurin-like 1 | 2q35 | 23363 | AI978623 | Hs.526594 | 1.03 | Upregulated in H2O2-treated SUM149 |
| CHAF1A | chromatin assembly factor 1, subunit A (p150) | 19p13.3 | 10036 | BF000239 | Hs.79018 | 1.03 | Upregulated in H2O2-treated SUM149 |
| TUBG1 | tubulin, gamma 1 | 17q21 | 7283 | NM_001070 | Hs.279669 | 1.03 | Upregulated in H2O2-treated SUM149 |
| NMI | N-myc (and STAT) interactor | 2q23 | 9111 | NM_004688 | Hs.54483 | 1.03 | Upregulated in H2O2-treated SUM149 |
| PDSS1 | prenyl (decaprenyl) diphosphate synthase, subunit 1 | 10p12.1 | 23590 | NM_014317 | Hs.558468 | 1.02 | Upregulated in H2O2-treated SUM149 |
| DHX9 | DEAH (Asp-Glu-Ala-His) box polypeptide 9 | 1q25 | 1660 | NM_001357 | Hs.191518 | 1.02 | Upregulated in H2O2-treated SUM149 |
| TARBP1 | TAR (HIV-1) RNA binding protein 1 | 1q42.3 | 6894 | NM_005646 | Hs.498115 | 1.02 | Upregulated in H2O2-treated SUM149 |
| TIMELESS | timeless homolog (Drosophila) | 12q12-q13 | 8914 | NM_003920 | Hs.118631 | 1.02 | Upregulated in H2O2-treated SUM149 |
| RPP30 | ribonuclease P/MRP 30kDa subunit | 10q23.31 | 10556 | AI760272 | Hs.139120 | 1.02 | Upregulated in H2O2-treated SUM149 |
| TRIP13 | thyroid hormone receptor interactor 13 | 5p15.33 | 9319 | NM_004237 | Hs.436187 | 1.02 | Upregulated in H2O2-treated SUM149 |
| SUCLG1 | succinate-CoA ligase, alpha subunit | 2p11.2 | 8802 | NM_003849 | Hs.270428 | 1.02 | Upregulated in H2O2-treated SUM149 |
| GNE | glucosamine (UDP-N-acetyl-2-epimerase/N-acetylmannosamine k~ | 9p13.3 | 10020 | NM_005476 | Hs.5920 | 1.02 | Upregulated in H2O2-treated SUM149 |
| CTPS2 | CTP synthase II | Xp22 | 56474 | NM_019857 | Hs.227049 | 1.01 | Upregulated in H2O2-treated SUM149 |
| ALDH3A2 | aldehyde dehydrogenase 3 family, member A2 | 17p11.2 | 224 | L47162 | Hs.499886 | 1.01 | Upregulated in H2O2-treated SUM149 |
| CCNF | cyclin F | 16p13.3 | 899 | NM_001761 | Hs.1973 | 1.01 | Upregulated in H2O2-treated SUM149 |
| MYBL1 | v-myb myeloblastosis viral oncogene homolog (avian)-like 1 | 8q22 | 4603 | AW592266 | Hs.445898 | 1.01 | Upregulated in H2O2-treated SUM149 |
| ST5 | suppression of tumorigenicity 5 | 11p15 | 6764 | NM_005418 | Hs.117715 | 1.01 | Upregulated in H2O2-treated SUM149 |
| GYS1 | glycogen synthase 1 (muscle) | 19q13.3 | 2997 | NM_002103 | Hs.386225 | 1.01 | Upregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| KPNA2 | karyopherin alpha 2 (RAG cohort 1, importin alpha 1) | 17q24.2 | 3838 | NM_002266 | Hs.594238 | 1.01 | Upregulated in H2O2-treated SUM149 |
| NPTX2 | neuronal pentraxin II | 7q21.3-q22.1 | 4885 | U26662 | Hs.3281 | 1.01 | Upregulated in H2O2-treated SUM149 |
| APOBEC3B | apolipoprotein B mRNA editing enzyme, catalytic polypeptide-- | 22q13.1-q13.2 | 9582 | NM_004900 | Hs.226307 | 1.01 | Upregulated in H2O2-treated SUM149 |
| NPRL2 | nitrogen permease regulator-like 2 (S. cerevisiae) | 3p21.3 | 10641 | NM_006545 | Hs.437083 | 1.00 | Upregulated in H2O2-treated SUM149 |
| MANSC1 | MANSC domain containing | 12p13.2 | 54682 | NM_018050 | Hs.591145 | 1.00 | Upregulated in H2O2-treated SUM149 |
| ALG6 | asparagine-linked glycosylation 6, alpha-1,3-glucosyltransfe- | 1p31.3 | 29929 | NM_013339 | Hs.258501 | 1.00 | Upregulated in H2O2-treated SUM149 |
| ACOT7 | acyl-CoA thioesterase 7 | 1p36 | 11332 | NM_007274 | Hs.126137 | 1.00 | Upregulated in H2O2-treated SUM149 |
| CIRBP | cold inducible RNA binding protein | 19p13.3 | 1153 | NM_001280 | Hs.618145 | -1.00 | Downregulated in H2O2-treated SUM149 |
| RB1CC1 | RB1-inducible coiled-coil 1 | 8q11 | 9821 | BG402105 | Hs.196102 | -1.00 | Downregulated in H2O2-treated SUM149 |
| SPEN | spen homolog, transcriptional regulator (Drosophila) | 1p36 | 23013 | W92026 | Hs.724378 | -1.00 | Downregulated in H2O2-treated SUM149 |
| CGRRF1 | cell growth regulator with ring finger domain 1 | 14q22.2 | 10668 | NM_006568 | Hs.59106 | -1.00 | Downregulated in H2O2-treated SUM149 |
| NFYB | nuclear transcription factor Y beta | 12q22-q23 | 4801 | AI804118 | Hs.84928 | -1.00 | Downregulated in H2O2-treated SUM149 |
| CSRNP2 | cysteine-serine-rich nuclear protein 2 | 12q13.11-q13.12 | 81566 | NM_030809 | Hs.524425 | -1.00 | Downregulated in H2O2-treated SUM149 |
| TK2 | thymidine kinase 2, mitochondrial | 16q22-q23.1 | 7084 | NM_004614 | Hs.512619 | -1.00 | Downregulated in H2O2-treated SUM149 |
| DLG1 | discs, large homolog 1 (Drosophila) | 3q29 | 1739 | AW139131 | Hs.292549 | -1.00 | Downregulated in H2O2-treated SUM149 |
| CEP63 | centrosomal protein 63kDa | 3q22.2 | 80254 | NM_025180 | Hs.443301 | -1.01 | Downregulated in H2O2-treated SUM149 |
| RBM41 | RNA binding motif protein 41 | Xq22.3 | 55285 | NM_018301 | Hs.139053 | -1.01 | Downregulated in H2O2-treated SUM149 |
| CLIP1 | CAP-GLY domain containing linker protein 1 | 12q24.3 | 6249 | BF673049 | Hs.524809 | -1.01 | Downregulated in H2O2-treated SUM149 |
| CGGBP1 | CGG triplet repeat binding protein 1 | 3p12-p11.1 | 8545 | NM_003663 | Hs.444818 | -1.01 | Downregulated in H2O2-treated SUM149 |
| GGPS1 | geranylgeranyl diphosphate synthase 1 | 1q43 | 9453 | AW299507 | Hs.724624 | -1.01 | Downregulated in H2O2-treated SUM149 |
| VPS28 | vacuolar protein sorting 28 homolog (S. cerevisiae) | 8q24.3 | 51160 | NM_016208 | Hs.418175 | -1.01 | Downregulated in H2O2-treated SUM149 |
| TFPI | tissue factor pathway inhibitor (lipoprotein-associated coag- | 2q32 | 7035 | J03225 | Hs.516578 | -1.02 | Downregulated in H2O2-treated SUM149 |
| STK4 | serine/threonine kinase 4 | 20q11.2-q13.2 | 6789 | BC039023 | Hs.472838 | -1.02 | Downregulated in H2O2-treated SUM149 |
| PIK3R1 | phosphoinositide-3-kinase, regulatory subunit 1 (alpha) | 5q13.1 | 5295 | AI680192 | Hs.132225 | -1.02 | Downregulated in H2O2-treated SUM149 |
| ZRSR2 | zinc finger (CCCH type), RNA-binding motif and serine/argini- | Xp22.1 | 8233 | NM_005089 | Hs.171909 | -1.02 | Downregulated in H2O2-treated SUM149 |
| SEC63 | SEC63 homolog (S. cerevisiae) | 6q21 | 11231 | AK001465 | Hs.26904 | -1.02 | Downregulated in H2O2-treated SUM149 |
| TFE3 | transcription factor binding to IGHM enhancer 3 | Xp11.22 | 7030 | AY034078 | Hs.274184 | -1.02 | Downregulated in H2O2-treated SUM149 |
| SAMD4A | sterile alpha motif domain containing 4A | 14q22.2 | 23034 | AB028976 | Hs.98259 | -1.02 | Downregulated in H2O2-treated SUM149 |
| NRIP1 | nuclear receptor interacting protein 1 | 21q11.2 | 8204 | NM_003489 | Hs.155017 | -1.02 | Downregulated in H2O2-treated SUM149 |
| NOP56 | NOP56 ribonucleoprotein homolog (yeast) | 20p13 | 10528 | BE796327 | Hs.376064 | -1.02 | Downregulated in H2O2-treated SUM149 |
| AHR | aryl hydrocarbon receptor | 7p15 | 196 | NM_001621 | Hs.171189 | -1.02 | Downregulated in H2O2-treated SUM149 |
| UPF2 | UPF2 regulator of nonsense | 10p14-p13 | 26019 | NM_015542 | Hs.370689 | -1.03 | Downregulated in H2O2- |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | transcripts homolog (yeast) | | | | | | treated SUM149 |
| TNC | tenascin C | 9q33 | 3371 | NM_002160 | Hs.143250 | -1.03 | Downregulated in H2O2-treated SUM149 |
| CRIM1 | cysteine rich transmembrane BMP regulator 1 (chordin-like) | 2p21 | 51232 | BG546884 | Hs.699247 | -1.03 | Downregulated in H2O2-treated SUM149 |
| C6orf106 | chromosome 6 open reading frame 106 | 6p21.31 | 64771 | NM_024294 | Hs.643498 | -1.03 | Downregulated in H2O2-treated SUM149 |
| MEF2A | myocyte enhancer factor 2A | 15q26 | 4205 | NM_005587 | Hs.268675 | -1.03 | Downregulated in H2O2-treated SUM149 |
| NIPBL | Nipped-B homolog (Drosophila) | 5p13.2 | 25836 | NM_015384 | Hs.481927 | -1.03 | Downregulated in H2O2-treated SUM149 |
| SEMA3C | sema domain, immunoglobulin domain (Ig), short basic domain,~ | 7q21-q31 | 10512 | AI962897 | Hs.269109 | -1.03 | Downregulated in H2O2-treated SUM149 |
| POLI | polymerase (DNA directed) iota | 18q21.1 | 11201 | NM_007195 | Hs.438533 | -1.03 | Downregulated in H2O2-treated SUM149 |
| CRYBB2P1 | Crystallin, beta B2 pseudogene 1 | 22q11.2-q12.1 | 1416 | AI686936 | Hs.571835 | -1.03 | Downregulated in H2O2-treated SUM149 |
| GADD45A | growth arrest and DNA-damage-inducible, alpha | 1p31.2 | 1647 | NM_001924 | Hs.80409 | -1.04 | Downregulated in H2O2-treated SUM149 |
| NR3C1 | nuclear receptor subfamily 3, group C, member 1 (glucocortic~ | 5q31.3 | 2908 | AI432196 | Hs.122926 | -1.04 | Downregulated in H2O2-treated SUM149 |
| SLC35F2 | solute carrier family 35, member F2 | 11q22.3 | 54733 | NM_017515 | Hs.524014 | -1.04 | Downregulated in H2O2-treated SUM149 |
| CREB3L2 | cAMP responsive element binding protein 3-like 2 | 7q34 | 64764 | BE675139 | Hs.703865 | -1.04 | Downregulated in H2O2-treated SUM149 |
| PPP4R4 | protein phosphatase 4, regulatory subunit 4 | 14q32.2 | 57718 | NM_020958 | Hs.259599 | -1.04 | Downregulated in H2O2-treated SUM149 |
| HIST3H2A | histone cluster 3, H2a | 1q42.13 | 92815 | BC001193 | Hs.26331 | -1.04 | Downregulated in H2O2-treated SUM149 |
| VAMP4 | vesicle-associated membrane protein 4 | 1q24-q25 | 8674 | NM_003762 | Hs.6651 | -1.04 | Downregulated in H2O2-treated SUM149 |
| HERPUD1 | homocysteine-inducible, endoplasmic reticulum stress inducib~ | 16q13 | 9709 | AF217990 | Hs.146393 | -1.04 | Downregulated in H2O2-treated SUM149 |
| RNMT | RNA (guanine-7-) methyltransferase | 18p11.21 | 8731 | NM_003799 | Hs.592347 | -1.04 | Downregulated in H2O2-treated SUM149 |
| PDCD4 | programmed cell death 4 (neoplastic transformation inhibitor~ | 10q24 | 27250 | BC043171 | Hs.711490 | -1.04 | Downregulated in H2O2-treated SUM149 |
| TGIF1 | TGFB-induced factor homeobox 1 | 18p11.3 | 7050 | AL832409 | Hs.373550 | -1.04 | Downregulated in H2O2-treated SUM149 |
| PPP1R15A | protein phosphatase 1, regulatory (inhibitor) subunit 15A | 19q13.2 | 23645 | NM_014330 | Hs.631593 | -1.05 | Downregulated in H2O2-treated SUM149 |
| PPP3R1 | protein phosphatase 3, regulatory subunit B, alpha | 2p15 | 5534 | AL544951 | Hs.280604 | -1.05 | Downregulated in H2O2-treated SUM149 |
| KIF5B | kinesin family member 5B | 10p11.22 | 3799 | BF223224 | Hs.327736 | -1.05 | Downregulated in H2O2-treated SUM149 |
| LAMB1 | laminin, beta 1 | 7q22 | 3912 | NM_002291 | Hs.650585 | -1.05 | Downregulated in H2O2-treated SUM149 |
| COL4A5 | collagen, type IV, alpha 5 | Xq22 | 1287 | AW052179 | Hs.369089 | -1.05 | Downregulated in H2O2-treated SUM149 |
| EGFR | epidermal growth factor receptor | 7p12 | 1956 | AF277897 | Hs.488293 | -1.05 | Downregulated in H2O2-treated SUM149 |
| HSPA13 | heat shock protein 70kDa family, member 13 | 21q11.1\|21q11 | 6782 | AI718418 | Hs.352341 | -1.05 | Downregulated in H2O2-treated SUM149 |
| ACSL1 | acyl-CoA synthetase long-chain family member 1 | 4q35 | 2180 | NM_021122 | Hs.406678 | -1.06 | Downregulated in H2O2-treated SUM149 |
| PHF3 | PHD finger protein 3 | 6q12 | 23469 | AI949220 | Hs.348921 | -1.06 | Downregulated in H2O2-treated SUM149 |
| CDK17 | cyclin-dependent kinase 17 | 12q23.1 | 5128 | NM_002595 | Hs.506415 | -1.06 | Downregulated in H2O2-treated SUM149 |
| N6AMT1 | N-6 adenine-specific DNA methyltransferase 1 (putative | 21q21.3 | 29104 | NM_013240 | Hs.163846 | -1.06 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| FOXO1 | forkhead box O1 | 13q14.1 | 2308 | AW117498 | Hs.370666 | -1.06 | Downregulated in H2O2-treated SUM149 |
| COL5A2 | collagen, type V, alpha 2 | 2q14-q32 | 1290 | AL575735 | Hs.445827 | -1.06 | Downregulated in H2O2-treated SUM149 |
| STK17B | serine/threonine kinase 17b | 2q32.3 | 9262 | NM_004226 | Hs.88297 | -1.07 | Downregulated in H2O2-treated SUM149 |
| MLL | myeloid/lymphoid or mixed-lineage leukemia (trithorax homolo~ | 11q23 | 4297 | AF272379 | Hs.258855 | -1.07 | Downregulated in H2O2-treated SUM149 |
| FAM190B | family with sequence similarity 190, member B | 10q23.1 | 54462 | BC030528 | Hs.461988 | -1.07 | Downregulated in H2O2-treated SUM149 |
| TSPAN4 | tetraspanin 4 | 11p15.5 | 7106 | BC000389 | Hs.654836 | -1.07 | Downregulated in H2O2-treated SUM149 |
| DCAF10 | DDB1 and CUL4 associated factor 10 | 9p13.2 | 79269 | NM_024345 | Hs.118394 | -1.07 | Downregulated in H2O2-treated SUM149 |
| IQGAP2 | IQ motif containing GTPase activating protein 2 | 5q13.3 | 10788 | NM_006633 | Hs.291030 | -1.08 | Downregulated in H2O2-treated SUM149 |
| TNKS2 | tankyrase, TRF1-interacting ankyrin-related ADP-ribose polym~ | 10q23.3 | 80351 | NM_025235 | Hs.329327 | -1.08 | Downregulated in H2O2-treated SUM149 |
| MED13L | mediator complex subunit 13 like | 12q24.21 | 23389 | BG426689 | Hs.603766 | -1.08 | Downregulated in H2O2-treated SUM149 |
| WIPI1 | WD repeat domain, phosphoinositide interacting 1 | 17q24.2 | 55062 | NM_017983 | Hs.463964 | -1.08 | Downregulated in H2O2-treated SUM149 |
| CCND2 | cyclin D2 | 12p13 | 894 | AW026491 | Hs.376071 | -1.08 | Downregulated in H2O2-treated SUM149 |
| AAK1 | AP2 associated kinase 1 | 2p14 | 22848 | AW451954 | Hs.468878 | -1.08 | Downregulated in H2O2-treated SUM149 |
| CAMSAP1L1 | calmodulin regulated spectrin-associated protein 1-like 1 | 1q32.1 | 23271 | AW593213 | Hs.23585 | -1.08 | Downregulated in H2O2-treated SUM149 |
| CBLB | Cas-Br-M (murine) ecotropic retroviral transforming sequence~ | 3q13.11 | 868 | NM_004351 | Hs.430589 | -1.08 | Downregulated in H2O2-treated SUM149 |
| NKTR | natural killer-tumor recognition sequence | 3p23-p21 | 4820 | AI880383 | Hs.529509 | -1.09 | Downregulated in H2O2-treated SUM149 |
| ABCA11P | ATP-binding cassette, sub-family A (ABC1), member 11 (pseudo~ | 4p16.3 | 79963 | NM_024903 | Hs.428360 | -1.09 | Downregulated in H2O2-treated SUM149 |
| MBNL1 | muscleblind-like (Drosophila) | 3q25 | 4154 | AF401998 | Hs.478000 | -1.09 | Downregulated in H2O2-treated SUM149 |
| SSH1 | slingshot homolog 1 (Drosophila) | 12q24.11 | 54434 | AB072356 | Hs.199763 | -1.09 | Downregulated in H2O2-treated SUM149 |
| GNAI1 | guanine nucleotide binding protein (G protein), alpha inhibi~ | 7q21 | 2770 | AL049933 | Hs.134587 | -1.09 | Downregulated in H2O2-treated SUM149 |
| CEBPG | CCAAT/enhancer binding protein (C/EBP), gamma | 19q13.11 | 1054 | NM_001806 | Hs.429666 | -1.09 | Downregulated in H2O2-treated SUM149 |
| INTS6 | integrator complex subunit 6 | 13q14.3 | 26512 | AW665713 | Hs.439440 | -1.09 | Downregulated in H2O2-treated SUM149 |
| RBFOX2 | RNA binding protein, fox-1 homolog (C. elegans) 2 | 22q13.1 | 23543 | N95026 | Hs.282998 | -1.09 | Downregulated in H2O2-treated SUM149 |
| PAWR | PRKC, apoptosis, WT1, regulator | 12q21 | 5074 | AI336206 | Hs.643130 | -1.10 | Downregulated in H2O2-treated SUM149 |
| TAB2 | TGF-beta activated kinase 1/MAP3K7 binding protein 2 | 6q25.1 | 23118 | AF241230 | Hs.269775 | -1.10 | Downregulated in H2O2-treated SUM149 |
| RPS6KA2 | ribosomal protein S6 kinase, 90kDa, polypeptide 2 | 6q27 | 6196 | BQ710550 | Hs.655277 | -1.10 | Downregulated in H2O2-treated SUM149 |
| NCAM1 | neural cell adhesion molecule 1 | 11q23.1 | 4684 | U63041 | Hs.503878 | -1.10 | Downregulated in H2O2-treated SUM149 |
| ELF1 | E74-like factor 1 (ets domain transcription factor) | 13q13 | 1997 | M82882 | Hs.135646 | -1.10 | Downregulated in H2O2-treated SUM149 |
| CELF1 | CUGBP, Elav-like family member 1 | 11p11 | 10658 | AF267533 | Hs.595333 | -1.11 | Downregulated in H2O2-treated SUM149 |
| SGPP1 | sphingosine-1-phosphate phosphatase 1 | 14q23.2 | 81537 | NM_030791 | Hs.24678 | -1.13 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| IFRD1 | interferon-related developmental regulator 1 | 7q31.1 | 3475 | AA747426 | Hs.7879 | -1.11 | Downregulated in H2O2-treated SUM149 |
| AZI2 | 5-azacytidine induced 2 | 3p24.1 | 64343 | NM_022461 | Hs.706676 | -1.12 | Downregulated in H2O2-treated SUM149 |
| GATAD1 | GATA zinc finger domain containing 1 | 7q21-q22 | 57798 | NM_021167 | Hs.21145 | -1.12 | Downregulated in H2O2-treated SUM149 |
| NAB1 | NGFI-A binding protein 1 (EGR1 binding protein 1) | 2q32.3-q33 | 4664 | NM_005966 | Hs.723892 | -1.12 | Downregulated in H2O2-treated SUM149 |
| DST | dystonin | 6p12.1 | 667 | NM_020388 | Hs.604915 | -1.12 | Downregulated in H2O2-treated SUM149 |
| FAM129A | family with sequence similarity 129, member A | 1q25 | 116496 | NM_022083 | Hs.518662 | -1.12 | Downregulated in H2O2-treated SUM149 |
| CTSZ | cathepsin Z | 20q13 | 1522 | AF073890 | Hs.252549 | -1.13 | Downregulated in H2O2-treated SUM149 |
| KLF5 | Kruppel-like factor 5 (intestinal) | 13q22.1 | 688 | AF132818 | Hs.508234 | -1.13 | Downregulated in H2O2-treated SUM149 |
| SPIN1 | spindlin 1 | 9q22.1 | 10927 | NM_006717 | Hs.146804 | -1.13 | Downregulated in H2O2-treated SUM149 |
| HIPK2 | homeodomain interacting protein kinase 2 | 7q32-q34 | 28996 | R37104 | Hs.724392 | -1.14 | Downregulated in H2O2-treated SUM149 |
| LITAF | lipopolysaccharide-induced TNF factor | 16p13.13 | 9516 | AF010312 | Hs.459940 | -1.14 | Downregulated in H2O2-treated SUM149 |
| PIP5K1A | phosphatidylinositol-4-phosphate 5-kinase, type I, alpha | 1q21.3 | 8394 | NM_003557 | Hs.655131 | -1.14 | Downregulated in H2O2-treated SUM149 |
| ZNF222 | zinc finger protein 222 | 19q13.2 | 7673 | NM_013360 | Hs.279840 | -1.15 | Downregulated in H2O2-treated SUM149 |
| BET1 | blocked early in transport 1 homolog (S. cerevisiae) | 7q21.1-q22 | 10282 | BC000899 | Hs.489132 | -1.15 | Downregulated in H2O2-treated SUM149 |
| GTPBP2 | GTP binding protein 2 | 6p21 | 54676 | NM_019096 | Hs.485449 | -1.15 | Downregulated in H2O2-treated SUM149 |
| CPEB3 | cytoplasmic polyadenylation element binding protein 3 | 10q23.32 | 22849 | BC036444 | Hs.131683 | -1.15 | Downregulated in H2O2-treated SUM149 |
| PEA15 | phosphoprotein enriched in astrocytes 15 | 1q21.1 | 8682 | BC002426 | Hs.517216 | -1.15 | Downregulated in H2O2-treated SUM149 |
| YPEL5 | yippee-like 5 (Drosophila) | 2p23.1 | 51646 | NM_016061 | Hs.515890 | -1.15 | Downregulated in H2O2-treated SUM149 |
| PRKAG2 | Protein kinase, AMP-activated, gamma 2 non-catalytic subunit | 7q36.1 | 51422 | AU144309 | Hs.647072 | -1.15 | Downregulated in H2O2-treated SUM149 |
| KDM5A | lysine (K)-specific demethylase 5A | 12p11 | 5927 | NM_005056 | Hs.76272 | -1.16 | Downregulated in H2O2-treated SUM149 |
| ZNF804A | zinc finger protein 804A | 2q32.1 | 91752 | AF052145 | Hs.159528 | -1.16 | Downregulated in H2O2-treated SUM149 |
| ZMYND11 | zinc finger, MYND domain containing 11 | 10p14 | 10771 | BC034784 | Hs.292265 | -1.16 | Downregulated in H2O2-treated SUM149 |
| NR1D2 | nuclear receptor subfamily 1, group D, member 2 | 3p24.2 | 9975 | N32859 | Hs.37288 | -1.16 | Downregulated in H2O2-treated SUM149 |
| TMF1 | TATA element modulatory factor 1 | 3p21-p12 | 7110 | BF593908 | Hs.267632 | -1.16 | Downregulated in H2O2-treated SUM149 |
| REL | v-rel reticuloendotheliosis viral oncogene homolog (avian) | 2p13-p12 | 5966 | NM_002908 | Hs.631886 | -1.16 | Downregulated in H2O2-treated SUM149 |
| PSPH | phosphoserine phosphatase | 7p11.2 | 5723 | NM_003832 | Hs.512656 | -1.16 | Downregulated in H2O2-treated SUM149 |
| KLF9 | Kruppel-like factor 9 | 9q13 | 687 | BF438302 | Hs.150557 | -1.17 | Downregulated in H2O2-treated SUM149 |
| PHLDA1 | pleckstrin homology-like domain, family A, member 1 | 12q15 | 22822 | AA576961 | Hs.602085 | -1.17 | Downregulated in H2O2-treated SUM149 |
| SLC35E2B | solute carrier family 35, member E2B | 1p36.33 | 728661 | AL031282 | Hs.655255 | -1.17 | Downregulated in H2O2-treated SUM149 |
| CLINT1 | clathrin interactor 1 | 5q33.3 | 9685 | BC004467 | Hs.644000 | -1.17 | Downregulated in H2O2-treated SUM149 |
| RBM7 | RNA binding motif protein 7 | 11q23.1-q23.2 | 10179 | NM_016090 | Hs.7527 | -1.17 | Downregulated in H2O2-treated SUM149 |
| PCNX | pecanex homolog (Drosophila) | 14q24.2 | 22990 | AB018348 | Hs.446559 | -1.18 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| TMEM40 | transmembrane protein 40 | 3p25.2 | 55287 | NM_018306 | Hs.475502 | -1.18 | Downregulated in H2O2-treated SUM149 |
| SATB1 | SATB homeobox 1 | 3p23 | 6304 | NM_002971 | Hs.517717 | -1.18 | Downregulated in H2O2-treated SUM149 |
| CDC42BPA | CDC42 binding protein kinase alpha (DMPK-like) | 1q42.11 | 8476 | NM_014826 | Hs.35433 | -1.18 | Downregulated in H2O2-treated SUM149 |
| TEAD1 | TEA domain family member 1 (SV40 transcriptional enhancer fa~ | 11p15.2 | 7003 | NM_021961 | Hs.655331 | -1.19 | Downregulated in H2O2-treated SUM149 |
| ACTR2 | ARP2 actin-related protein 2 homolog (yeast) | 2p14 | 10097 | BC036253 | Hs.723952 | -1.19 | Downregulated in H2O2-treated SUM149 |
| PMAIP1 | phorbol-12-myristate-13-acetate-induced protein 1 | 18q21.32 | 5366 | AI857639 | Hs.96 | -1.19 | Downregulated in H2O2-treated SUM149 |
| TAF13 | TAF13 RNA polymerase II, TATA box binding protein (TBP)-asso~ | 1p13.3 | 6884 | NM_005645 | Hs.632426 | -1.19 | Downregulated in H2O2-treated SUM149 |
| NMT2 | N-myristoyltransferase 2 | 10p13 | 9397 | AW293531 | Hs.60339 | -1.19 | Downregulated in H2O2-treated SUM149 |
| TFAP2A | transcription factor AP-2 alpha (activating enhancer binding~ | 6p24 | 7020 | BF343007 | Hs.519880 | -1.19 | Downregulated in H2O2-treated SUM149 |
| TMOD3 | tropomodulin 3 (ubiquitous) | 15q21.1-q21.2 | 29766 | NM_014547 | Hs.4998 | -1.20 | Downregulated in H2O2-treated SUM149 |
| ALDH6A1 | aldehyde dehydrogenase 6 family, member A1 | 14q24.3 | 4329 | NM_005589 | Hs.293970 | -1.20 | Downregulated in H2O2-treated SUM149 |
| MAP4K5 | mitogen-activated protein kinase kinase kinase kinase 5 | 14q11.2-q21 | 11183 | AW298170 | Hs.130491 | -1.20 | Downregulated in H2O2-treated SUM149 |
| KCNE4 | potassium voltage-gated channel, Isk-related family, member ~ | 2q36.3 | 23704 | NM_080671 | Hs.348522 | -1.20 | Downregulated in H2O2-treated SUM149 |
| MYOZ2 | myozenin 2 | 4q26-q27 | 51778 | NM_016599 | Hs.381047 | -1.21 | Downregulated in H2O2-treated SUM149 |
| IL6ST | interleukin 6 signal transducer (gp130, oncostatin M recepto~ | 5q13 | 3572 | BE856546 | Hs.532082 | -1.21 | Downregulated in H2O2-treated SUM149 |
| RABGAP1L | RAB GTPase activating protein 1-like | 1q24 | 9910 | BC041888 | Hs.585378 | -1.22 | Downregulated in H2O2-treated SUM149 |
| FLRT3 | fibronectin leucine rich transmembrane protein 3 | 20p11 | 23767 | NM_013281 | Hs.41296 | -1.22 | Downregulated in H2O2-treated SUM149 |
| EBAG9 | estrogen receptor binding site associated, antigen, 9 | 8q23 | 9166 | AA812215 | Hs.409368 | -1.22 | Downregulated in H2O2-treated SUM149 |
| GALK2 | galactokinase 2 | 15q21.1-q21.2 | 2585 | NM_002044 | Hs.122006 | -1.22 | Downregulated in H2O2-treated SUM149 |
| SMG1 | SMG1 homolog, phosphatidylinositol 3-kinase-related kinase (~ | 16p12.3 | 23049 | U32581 | Hs.460179 | -1.22 | Downregulated in H2O2-treated SUM149 |
| ACBD3 | acyl-CoA binding domain containing 3 | 1q42.12 | 64746 | AI636775 | Hs.520207 | -1.23 | Downregulated in H2O2-treated SUM149 |
| CCPG1 | cell cycle progression 1 | 15q21.1 | 9236 | AU144243 | Hs.285051 | -1.23 | Downregulated in H2O2-treated SUM149 |
| SGPL1 | sphingosine-1-phosphate lyase 1 | 10q21 | 8879 | NM_003901 | Hs.499984 | -1.23 | Downregulated in H2O2-treated SUM149 |
| PDGFC | platelet derived growth factor C | 4q32 | 56034 | NM_016205 | Hs.570855 | -1.24 | Downregulated in H2O2-treated SUM149 |
| SLC7A1 | solute carrier family 7 (cationic amino acid transporter, y+~ | 13q12-q14 | 6541 | NM_003045 | Hs.14846 | -1.24 | Downregulated in H2O2-treated SUM149 |
| CCNG2 | cyclin G2 | 4q21.1 | 901 | BC032518 | Hs.724499 | -1.25 | Downregulated in H2O2-treated SUM149 |
| CDC42EP1 | CDC42 effector protein (Rho GTPase binding) 1 | 22q13.1 | 11135 | NM_007061 | Hs.225356 | -1.25 | Downregulated in H2O2-treated SUM149 |
| IGF1R | insulin-like growth factor 1 receptor | 15q26.3 | 3480 | AI830698 | Hs.643120 | -1.26 | Downregulated in H2O2-treated SUM149 |
| RSRC2 | arginine/serine-rich coiled-coil 2 | 12q24.31 | 65117 | BE396879 | Hs.432996 | -1.26 | Downregulated in H2O2-treated SUM149 |
| INTS12 | integrator complex subunit 12 | 4q24 | 57117 | NM_020395 | Hs.480454 | -1.27 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| VEGFA | vascular endothelial growth factor A | 6p12 | 7422 | AF022375 | Hs.73793 | -1.27 | Downregulated in H2O2-treated SUM149 |
| EREG | epiregulin | 4q13.3 | 2069 | BC035806 | Hs.115263 | -1.27 | Downregulated in H2O2-treated SUM149 |
| MARS | methionyl-tRNA synthetase | 12q13.2 | 4141 | NM_004990 | Hs.632707 | -1.28 | Downregulated in H2O2-treated SUM149 |
| EEA1 | early endosome antigen 1 | 12q22 | 8411 | AI916242 | Hs.567367 | -1.29 | Downregulated in H2O2-treated SUM149 |
| EPRS | glutamyl-prolyl-tRNA synthetase | 1q41 | 2058 | AI342677 | Hs.497788 | -1.29 | Downregulated in H2O2-treated SUM149 |
| NRBF2 | nuclear receptor binding factor 2 | 10q21.3 | 29982 | AA883074 | Hs.449628 | -1.29 | Downregulated in H2O2-treated SUM149 |
| TUFT1 | tuftelin 1 | 1q21 | 7286 | NM_020127 | Hs.489922 | -1.30 | Downregulated in H2O2-treated SUM149 |
| TTBK2 | tau tubulin kinase 2 | 15q15.2 | 146057 | BC041876 | Hs.724640 | -1.30 | Downregulated in H2O2-treated SUM149 |
| DUSP1 | dual specificity phosphatase | 5q34 | 1843 | NM_004417 | Hs.171695 | -1.30 | Downregulated in H2O2-treated SUM149 |
| CDH12 | cadherin 12, type 2 (N-cadherin 2) | 5p14.3 | 1010 | L33477 | Hs.113684 | -1.30 | Downregulated in H2O2-treated SUM149 |
| SEC24A | SEC24 family, member A (S cerevisiae) | 5q31.1 | 10802 | AJ131244 | Hs.595540 | -1.31 | Downregulated in H2O2-treated SUM149 |
| TSC22D3 | TSC22 domain family, member 3 | Xq22.3 | 1831 | NM_004089 | Hs.522074 | -1.31 | Downregulated in H2O2-treated SUM149 |
| DNAJB9 | DnaJ (Hsp40) homolog, subfamily B, member 9 | q31\|14q24.2-q24.3 | 4189 | AF115512 | Hs.6790 | -1.31 | Downregulated in H2O2-treated SUM149 |
| CADM1 | cell adhesion molecule 1 | 11q23.2 | 23705 | NM_014333 | Hs.370510 | -1.31 | Downregulated in H2O2-treated SUM149 |
| ZBTB38 | zinc finger and BTB domain containing 38 | 3q23 | 253461 | BE386445 | Hs.518301 | -1.32 | Downregulated in H2O2-treated SUM149 |
| LARP6 | La ribonucleoprotein domain family, member 6 | 15q23 | 55323 | NM_018357 | Hs.416755 | -1.32 | Downregulated in H2O2-treated SUM149 |
| SNAPC1 | small nuclear RNA activating complex, polypeptide 1, 43kDa | 14q22 | 6617 | NM_003082 | Hs.179312 | -1.32 | Downregulated in H2O2-treated SUM149 |
| NFE2L1 | nuclear factor (erythroid-derived 2)-like 1 | 17q21.3 | 4779 | AI361227 | Hs.514284 | -1.33 | Downregulated in H2O2-treated SUM149 |
| WDR5B | WD repeat domain 5B | 3q21.1 | 54554 | NM_019069 | Hs.567513 | -1.33 | Downregulated in H2O2-treated SUM149 |
| DIO2 | deiodinase, iodothyronine, type II | 14q24.2-q24.3 | 1734 | U53506 | Hs.202354 | -1.33 | Downregulated in H2O2-treated SUM149 |
| STC2 | stanniocalcin 2 | 5q35.1 | 8614 | AI435828 | Hs.233160 | -1.33 | Downregulated in H2O2-treated SUM149 |
| GATA3 | GATA binding protein 3 | 10p15 | 2625 | AI796169 | Hs.524134 | -1.33 | Downregulated in H2O2-treated SUM149 |
| BRD4 | bromodomain containing 4 | 19p13.1 | 23476 | BF718610 | Hs.187763 | -1.34 | Downregulated in H2O2-treated SUM149 |
| ARNTL | aryl hydrocarbon receptor nuclear translocator-like | 11p15 | 406 | AB000812 | Hs.65734 | -1.34 | Downregulated in H2O2-treated SUM149 |
| CTBS | chitobiase, di-N-acetyl- | 1p22 | 1486 | AW304174 | Hs.513557 | -1.34 | Downregulated in H2O2-treated SUM149 |
| SKAP2 | src kinase associated phosphoprotein 2 | 7p15.2 | 8935 | AB014486 | Hs.200770 | -1.35 | Downregulated in H2O2-treated SUM149 |
| PCDH9 | protocadherin 9 | 13q21.32 | 5101 | AI524125 | Hs.654709 | -1.35 | Downregulated in H2O2-treated SUM149 |
| ACVR1 | activin A receptor, type I | 2q23-q24 | 90 | NM_001105 | Hs.470316 | -1.35 | Downregulated in H2O2-treated SUM149 |
| LRRFIP2 | leucine rich repeat (in FLII) interacting protein 2 | 3p22.2 | 9209 | NM_017724 | Hs.724588 | -1.35 | Downregulated in H2O2-treated SUM149 |
| CREB5 | cAMP responsive element binding protein 5 | 7p15.1 | 9586 | NM_004904 | Hs.437075 | -1.35 | Downregulated in H2O2-treated SUM149 |
| ALG13 | asparagine-linked glycosylation 13 homolog (S cerevisiae) | Xq23 | 79868 | NM_024810 | Hs.443061 | -1.36 | Downregulated in H2O2-treated SUM149 |
| SNAP23 | synaptosomal-associated protein, 23kDa | 15q14 | 8773 | BC003686 | Hs.724586 | -1.36 | Downregulated in H2O2-treated SUM149 |
| PBLD | phenazine biosynthesis-like | 10pter-q25.3 | 64081 | BC009738 | Hs.198158 | -1.36 | Downregulated in H2O2- |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | protein domain containing | | | | | | treated SUM149 |
| APBB2 | amyloid beta (A4) precursor protein-binding, family B, membe-- | 4p13 | 323 | AI694303 | Hs.479602 | -1.36 | Downregulated in H2O2-treated SUM149 |
| ALDH1A1 | aldehyde dehydrogenase 1 family, member A1 | 9q21.13 | 216 | NM_000689 | Hs.76392 | -1.36 | Downregulated in H2O2-treated SUM149 |
| DLC1 | deleted in liver cancer 1 | 8p22 | 10395 | AF026219 | Hs.134296 | -1.36 | Downregulated in H2O2-treated SUM149 |
| SETD4 | SET domain containing 4 | 21q22.13 | 54093 | AB004853 | Hs.606200 | -1.37 | Downregulated in H2O2-treated SUM149 |
| NRP1 | Neuropilin 1 | 10p12 | 8829 | AA609131 | Hs.131704 | -1.37 | Downregulated in H2O2-treated SUM149 |
| GPM6A | glycoprotein M6A | 4q34 | 2823 | BF939489 | Hs.724382 | -1.38 | Downregulated in H2O2-treated SUM149 |
| SIM2 | single-minded homolog 2 (Drosophila) | 21q22.2\|21q22.13 | 6493 | NM_005069 | Hs.146186 | -1.39 | Downregulated in H2O2-treated SUM149 |
| IL1RAP | interleukin 1 receptor accessory protein | 3q28 | 3556 | NM_002182 | Hs.478673 | -1.40 | Downregulated in H2O2-treated SUM149 |
| RIT1 | Ras-like without CAAX 1 | 1q22 | 6016 | AF084462 | Hs.491234 | -1.40 | Downregulated in H2O2-treated SUM149 |
| ZFAND3 | zinc finger, AN1-type domain 3 | 6pter-p22.3 | 60685 | NM_021943 | Hs.36959 | -1.40 | Downregulated in H2O2-treated SUM149 |
| SLC1A4 | solute carrier family 1 (glutamate/neutral amino aci transp-- | 2p15-p13 | 6509 | BF340083 | Hs.654352 | -1.42 | Downregulated in H2O2-treated SUM149 |
| RANBP9 | RAN binding protein 9 | 6p23 | 10048 | AF306510 | Hs.708182 | -1.43 | Downregulated in H2O2-treated SUM149 |
| PTP4A1 | protein tyrosine phosphatase type IVA, member 1 | 6q12 | 7803 | BF576710 | Hs.227777 | -1.43 | Downregulated in H2O2-treated SUM149 |
| KCNMA1 | potassium large conductance calcium-activated channel, subfa-- | 10q22.3 | 3778 | U02632 | Hs.144795 | -1.44 | Downregulated in H2O2-treated SUM149 |
| PRNP | prion protein | 20p13 | 5621 | NM_000311 | Hs.472010 | -1.45 | Downregulated in H2O2-treated SUM149 |
| LPHN3 | latrophilin 3 | 4q13.1 | 23284 | R50822 | Hs.570770 | -1.45 | Downregulated in H2O2-treated SUM149 |
| MAP1LC3B | microtubule-associated protein 1 light chain 3 beta | 16q24.2 | 81631 | BE893893 | Hs.356061 | -1.45 | Downregulated in H2O2-treated SUM149 |
| ZFR | zinc finger RNA binding protein | 5p13.3 | 51663 | BC000376 | Hs.435231 | -1.45 | Downregulated in H2O2-treated SUM149 |
| MAP4 | microtubule-associated protein 4 | 3p21 | 4134 | AI553791 | Hs.517949 | -1.45 | Downregulated in H2O2-treated SUM149 |
| SYNE2 | spectrin repeat containing, nuclear envelope 2 | 14q23.2 | 23224 | BQ363771 | Hs.525392 | -1.46 | Downregulated in H2O2-treated SUM149 |
| LRP12 | low density lipoprotein receptor-related protein 12 | 8q22.2 | 29967 | NM_024937 | Hs.600630 | -1.46 | Downregulated in H2O2-treated SUM149 |
| ATF3 | activating transcription facto 3 | 1q32.3 | 467 | AB078026 | Hs.460 | -1.47 | Downregulated in H2O2-treated SUM149 |
| TNFAIP6 | tumor necrosis factor, alpha-induced protein 6 | 2q23.3 | 7130 | AW188198 | Hs.437322 | -1.47 | Downregulated in H2O2-treated SUM149 |
| CHMP1B | chromatin modifying protein 1B | 18p11.21 | 57132 | AA293502 | Hs.656244 | -1.48 | Downregulated in H2O2-treated SUM149 |
| SLCO1B3 | solute carrier organic anion transporter family, member 1B3 | 12p12 | 28234 | NM_019844 | Hs.504966 | -1.48 | Downregulated in H2O2-treated SUM149 |
| DBT | dihydrolipoamide branched chain transacylase E2 | 1p31 | 1629 | J03208 | Hs.709187 | -1.48 | Downregulated in H2O2-treated SUM149 |
| YAF2 | YY1 associated factor 2 | 12q12 | 10138 | NM_005748 | Hs.708084 | -1.48 | Downregulated in H2O2-treated SUM149 |
| KLF4 | Kruppel-like factor 4 (gut) | 9q31 | 9314 | NM_004235 | Hs.376206 | -1.49 | Downregulated in H2O2-treated SUM149 |
| SLC2A9 | solute carrier family 2 (facilitated glucose transporter), m-- | 4p16.1 | 56606 | NM_020041 | Hs.656895 | -1.50 | Downregulated in H2O2-treated SUM149 |
| H1F0 | H1 histone family, member 0 | 22q13.1 | 3005 | BC000145 | Hs.723964 | -1.52 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| XIAP | X-linked inhibitor of apoptosis | Xq25 | 331 | U32974 | Hs.356076 | -1.53 | Downregulated in H2O2-treated SUM149 |
| PPFIBP1 | PTPRF interacting protein, binding protein 1 (liprin beta 1) | 12p12.1 | 8496 | BC001560 | Hs.172445 | -1.53 | Downregulated in H2O2-treated SUM149 |
| LMAN1 | lectin, mannose-binding, 1 | 18q21.3-q22 | 3998 | NM_005570 | Hs.465295 | -1.54 | Downregulated in H2O2-treated SUM149 |
| EHBP1 | EH domain binding protein 1 | 2p15 | 23301 | BF116032 | Hs.271667 | -1.55 | Downregulated in H2O2-treated SUM149 |
| ACTA2 | actin, alpha 2, smooth muscle, aorta | 10q23.3 | 59 | NM_001613 | Hs.500483 | -1.55 | Downregulated in H2O2-treated SUM149 |
| KDM5B | lysine (K)-specific demethylase 5B | 1q32.1 | 10765 | AA729218 | Hs.443650 | -1.55 | Downregulated in H2O2-treated SUM149 |
| SNX24 | sorting nexin 24 | 5q23.2 | 28966 | NM_014035 | Hs.483200 | -1.57 | Downregulated in H2O2-treated SUM149 |
| GABARAPL1 | GABA(A) receptor-associated protein like 1 | 12p13.2 | 23710 | BF125756 | Hs.524250 | -1.57 | Downregulated in H2O2-treated SUM149 |
| SENP6 | SUMO1/sentrin specific peptidase 6 | 6q13-q14.3 | 26054 | AF306508 | Hs.485784 | -1.57 | Downregulated in H2O2-treated SUM149 |
| ULK1 | unc-51-like kinase 1 (C. elegans) | 12q24.3 | 8408 | AB018265 | Hs.47061 | -1.59 | Downregulated in H2O2-treated SUM149 |
| JAG1 | jagged 1 | 20p12.1-p11.23 | 182 | BF056748 | Hs.724464 | -1.59 | Downregulated in H2O2-treated SUM149 |
| PCK2 | phosphoenolpyruvate carboxykinase 2 (mitochondrial) | 14q11.2 | 5106 | NM_004563 | Hs.75812 | -1.60 | Downregulated in H2O2-treated SUM149 |
| PTPN2 | protein tyrosine phosphatase, non-receptor type 2 | 18p11.3-p11.2 | 5771 | NM_002828 | Hs.654527 | -1.60 | Downregulated in H2O2-treated SUM149 |
| EPHA3 | EPH receptor A3 | 3p11.2 | 2042 | AF213459 | Hs.123642 | -1.61 | Downregulated in H2O2-treated SUM149 |
| TIMP3 | TIMP metallopeptidase inhibitor 3 | 22q12.1-q13.2|22q12.3 | 7078 | BF347089 | Hs.644633 | -1.61 | Downregulated in H2O2-treated SUM149 |
| AGFG1 | ArfGAP with FG repeats 1 | 2q36.3 | 3267 | AI742626 | Hs.352962 | -1.62 | Downregulated in H2O2-treated SUM149 |
| CDV3 | CDV3 homolog (mouse) | 3q22.1 | 55573 | AK025647 | Hs.518265 | -1.63 | Downregulated in H2O2-treated SUM149 |
| NUPR1 | nuclear protein, transcriptional regulator, 1 | 16p11.2 | 26471 | AF135266 | Hs.513463 | -1.63 | Downregulated in H2O2-treated SUM149 |
| VCAN | versican | 5q14.3 | 1462 | BF590263 | Hs.643801 | -1.63 | Downregulated in H2O2-treated SUM149 |
| PTER | phosphotriesterase related | 10p12 | 9317 | NM_030664 | Hs.444321 | -1.63 | Downregulated in H2O2-treated SUM149 |
| MST4 | serine/threonine protein kinase MST4 | Xq26.2 | 51765 | NM_016542 | Hs.444247 | -1.64 | Downregulated in H2O2-treated SUM149 |
| ZBTB43 | zinc finger and BTB domain containing 43 | 9q33-q34 | 23099 | AI745225 | Hs.355581 | -1.68 | Downregulated in H2O2-treated SUM149 |
| ARFRP1 | ADP-ribosylation factor related protein 1 | 20q13.3 | 10139 | NM_003224 | Hs.389277 | -1.69 | Downregulated in H2O2-treated SUM149 |
| TRIB3 | tribbles homolog 3 (Drosophila) | 20p13-p12.2 | 57761 | AF250311 | Hs.516826 | -1.70 | Downregulated in H2O2-treated SUM149 |
| PLAC8 | placenta-specific 8 | 4q21.22 | 51316 | NM_016619 | Hs.546392 | -1.71 | Downregulated in H2O2-treated SUM149 |
| WSB1 | WD repeat and SOCS box-containing 1 | 17q11.1 | 26118 | N24643 | Hs.446017 | -1.72 | Downregulated in H2O2-treated SUM149 |
| ADARB1 | adenosine deaminase, RNA-specific, B1 | 21q22.3 | 104 | NM_015833 | Hs.474018 | -1.72 | Downregulated in H2O2-treated SUM149 |
| COBLL1 | COBL-like 1 | 2q24.3 | 22837 | BF002844 | Hs.470457 | -1.73 | Downregulated in H2O2-treated SUM149 |
| THBS1 | thrombospondin 1 | 15q15 | 7057 | AI812030 | Hs.164226 | -1.73 | Downregulated in H2O2-treated SUM149 |
| UNC5B | unc-5 homolog B (C. elegans) | 10q22.1 | 219699 | AA127885 | Hs.522997 | -1.73 | Downregulated in H2O2-treated SUM149 |
| SOHLH2 | spermatogenesis and oogenesis specific basic helix-loop-helix 2 | 13q13.3 | 54937 | BC025383 | Hs.124519 | -1.75 | Downregulated in H2O2-treated SUM149 |
| LOC388796 | hypothetical LOC388796 | 20q11.23 | 388796 | AA827892 | Hs.400876 | -1.76 | Downregulated in H2O2-treated SUM149 |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| JHDM1D | jumonji C domain containing histone demethylase 1 homolog D | 7q34 | 80853 | BE217882 | Hs.308710 | -1.77 | Downregulated in H2O2-treated SUM149 |
| RNF41 | ring finger protein 41 | 12q13.13 | 10193 | AL583171 | Hs.524502 | -1.78 | Downregulated in H2O2-treated SUM149 |
| CHAC1 | ChaC, cation transport regulator homolog 1 (E. coli) | 15q15.1 | 79094 | NM_024111 | Hs.155569 | -1.79 | Downregulated in H2O2-treated SUM149 |
| PICALM | phosphatidylinositol binding clathrin assembly protein | 11q14 | 8301 | NM_007166 | Hs.163893 | -1.79 | Downregulated in H2O2-treated SUM149 |
| ABCG1 | ATP-binding cassette, sub-family G (WHITE), member 1 | 21q22.3 | 9619 | NM_004915 | Hs.124649 | -1.84 | Downregulated in H2O2-treated SUM149 |
| ZMYM5 | zinc finger, MYM-type 5 | 13q12 | 9205 | NM_016384 | Hs.530988 | -1.84 | Downregulated in H2O2-treated SUM149 |
| COL8A1 | collagen, type VIII, alpha 1 | 3q12.3 | 1295 | BE877796 | Hs.654548 | -1.86 | Downregulated in H2O2-treated SUM149 |
| FYN | FYN oncogene related to SRC, FGR, YES | 6q21 | 2534 | AK090692 | Hs.390567 | -1.86 | Downregulated in H2O2-treated SUM149 |
| IL1A | interleukin 1, alpha | 2q14 | 3552 | NM_000575 | Hs.1722 | -1.89 | Downregulated in H2O2-treated SUM149 |
| CALCB | calcitonin-related polypeptide beta | 11p15.2-p15.1 | 797 | AA747379 | Hs.534305 | -1.91 | Downregulated in H2O2-treated SUM149 |
| WAC | WW domain containing adaptor with coiled-coil | --- | 51322 | NM_016628 | Hs.435610 | -1.93 | Downregulated in H2O2-treated SUM149 |
| PPM1A | protein phosphatase, Mg2+/Mn2+ dependent, 1A | 14q23.1 | 5494 | NM_021003 | Hs.130036 | -1.96 | Downregulated in H2O2-treated SUM149 |
| BMPR2 | bone morphogenetic protein receptor, type II (serine/threoni- | 2q33-q34 | 659 | U20165 | Hs.471119 | -1.96 | Downregulated in H2O2-treated SUM149 |
| SETD2 | SET domain containing 2 | 3p21.31 | 29072 | AI761110 | Hs.517941 | -2.01 | Downregulated in H2O2-treated SUM149 |
| PDE4D | phosphodiesterase 4D, cAMP-specific | 5q12 | 5144 | BC008390 | Hs.117545 | -2.01 | Downregulated in H2O2-treated SUM149 |
| SLC7A11 | solute carrier family 7, (cationic amino acid transporter, y- | 4q28-q32 | 23657 | NM_014331 | Hs.390594 | -2.01 | Downregulated in H2O2-treated SUM149 |
| TANC2 | tetratricopeptide repeat, ankyrin repeat and coiled-coi con- | 17q23.3 | 26115 | NM_015623 | Hs.410889 | -2.14 | Downregulated in H2O2-treated SUM149 |
| IL1B | interleukin 1, beta | 2q14 | 3553 | NM_000576 | Hs.126256 | -2.14 | Downregulated in H2O2-treated SUM149 |
| KRCC1 | lysine-rich coiled-coil 1 | 2p11.2 | 51315 | NM_016618 | Hs.469254 | -2.14 | Downregulated in H2O2-treated SUM149 |
| GDF15 | growth differentiation factor 15 | 19p13.11 | 9518 | BC000529 | Hs.616962 | -2.16 | Downregulated in H2O2-treated SUM149 |
| ABCA1 | ATP-binding cassette, sub-family A (ABC1), member 1 | 9q31.1 | 19 | BC034824 | Hs.429294 | -2.18 | Downregulated in H2O2-treated SUM149 |
| COL4A6 | collagen, type IV, alpha 6 | Xq22 | 1288 | BC005305 | Hs.145586 | -2.20 | Downregulated in H2O2-treated SUM149 |
| FGF2 | fibroblast growth factor 2 (basic) | 4q26 | 2247 | M27968 | Hs.284244 | -2.22 | Downregulated in H2O2-treated SUM149 |
| TREM1 | triggering receptor expressed on myeloid cells 1 | 6p21.1 | 54210 | NM_018643 | Hs.283022 | -2.22 | Downregulated in H2O2-treated SUM149 |
| ABCA6 | ATP-binding cassette, sub-family A (ABC1), member 6 | 17q24.3 | 23460 | AA099357 | Hs.769514 | -2.23 | Downregulated in H2O2-treated SUM149 |
| CTH | cystathionase (cystathionine gamma-lyase) | 1p31.1 | 1491 | NM_001902 | Hs.19904 | -2.27 | Downregulated in H2O2-treated SUM149 |
| ECM2 | extracellular matrix protein 2 female organ and adipocyte s- | 9q22.3 | 1842 | AI473096 | Hs.117060 | -2.38 | Downregulated in H2O2-treated SUM149 |
| OASL | 2'-5'-oligoadenylate synthetase-like | 12q24.2 | 8638 | NM_003733 | Hs.118633 | -2.43 | Downregulated in H2O2-treated SUM149 |
| CEBPD | CCAAT/enhancer binding protein (C/EBP), delta | 8p11.2-p11.1 | 1052 | NM_005195 | Hs.440829 | -2.44 | Downregulated in H2O2-treated SUM149 |
| TP63 | tumor protein p63 | 3q28 | 8626 | AF075429 | Hs.137569 | -2.45 | Downregulated in H2O2-treated SUM149 |
| RAB5A | RAB5A, member RAS | 3p24-p22 | 5868 | NM_004162 | Hs.475663 | -2.47 | Downregulated in H2O2- |

FIG. 10 (CONT.)

| Symbol | Gene Title | Chromosomal Location | Entrez Gene ID | Representative Public ID | UniGene ID | Fold-Change (log2) | Associated to |
|---|---|---|---|---|---|---|---|
| | oncogene family | | | | | | treated SUM149 |
| SLC4A7 | solute carrier family 4, sodium bicarbonate cotransporter, m- | 3p22 | 9497 | NM_003615 | Hs.250072 | -2.49 | Downregulated in H2O2-treated SUM149 |
| MBNL2 | Muscleblind-like 2 (Drosophila) | 13q32.1 | 10150 | NM_018615 | Hs.657347 | -2.50 | Downregulated in H2O2-treated SUM149 |
| RBMS3 | RNA binding motif, single stranded interacting protein 3 | 3p24-p23 | 27303 | AL831860 | Hs.696468 | -2.51 | Downregulated in H2O2-treated SUM149 |
| KLHL24 | kelch-like 24 (Drosophila) | 3q27.1 | 54800 | NM_017644 | Hs.407709 | -2.51 | Downregulated in H2O2-treated SUM149 |
| TXNIP | thioredoxin interacting protein | 1q21.1 | 10628 | AA812232 | Hs.724431 | -2.55 | Downregulated in H2O2-treated SUM149 |
| FCAR | Fc fragment of IgA, receptor for | 19q13.2-q13.4 | 2204 | NM_002000 | Hs.659872 | -2.68 | Downregulated in H2O2-treated SUM149 |
| AREG | amphiregulin | 4q13-q21 | 374 | NM_001657 | Hs.270833 | -2.81 | Downregulated in H2O2-treated SUM149 |
| ANXA3 | annexin A3 | 4q21.21 | 306 | M63310 | Hs.480042 | -2.88 | Downregulated in H2O2-treated SUM149 |
| PTGS2 | prostaglandin-endoperoxide synthase 2 (prostaglandin G/H syn- | 1q25.2-q25.3 | 5743 | AY151286 | Hs.196384 | -2.88 | Downregulated in H2O2-treated SUM149 |
| NRG1 | neuregulin 1 | 8p12 | 3084 | NM_013957 | Hs.453951 | -3.15 | Downregulated in H2O2-treated SUM149 |
| INHBE | inhibin, beta E | 12q13.3 | 83729 | BC005161 | Hs.632713 | -3.49 | Downregulated in H2O2-treated SUM149 |

FIG. 11

| Group (n) | Mouse weight (g) | | Tumor burden (mg/g) | Tumor doubling (days) |
|---|---|---|---|---|
| | starting | ending | | |
| Vehicle (6) | 22.7±1.5 | 22.9±1.6 | 62.4±7.4 | 4.9±2.0 |
| DSF (7) | 20.6±1.3 | 22.0±1.0 | 35.7±6.1 | 8.4±4.2 |
| DSF-Cu (7) | 19.5±0.4 | 20.7±0.3 | 16.2±3.2 | N/A (lag phase) |

Result 1:

DSF-Cu inhibits 3D Tumor spheroids derived from SUM149 and an isotype matched multidrug resistant rSUM149 cells DSF-Cu inhibits in vitro tumor emboli formation. SUM149 cells in lymphatic simulating tumor emboli model (Lehman, 2013) treated with DSF, Cu and DSF-Cu at the time of seeding. Spheroids manually counted using phase contrast microscopy on day 4.

Result 3:
High Content, High Throughput Assay used to study the effect of DSF-Cu on in vitro IBC Tumor Emboli

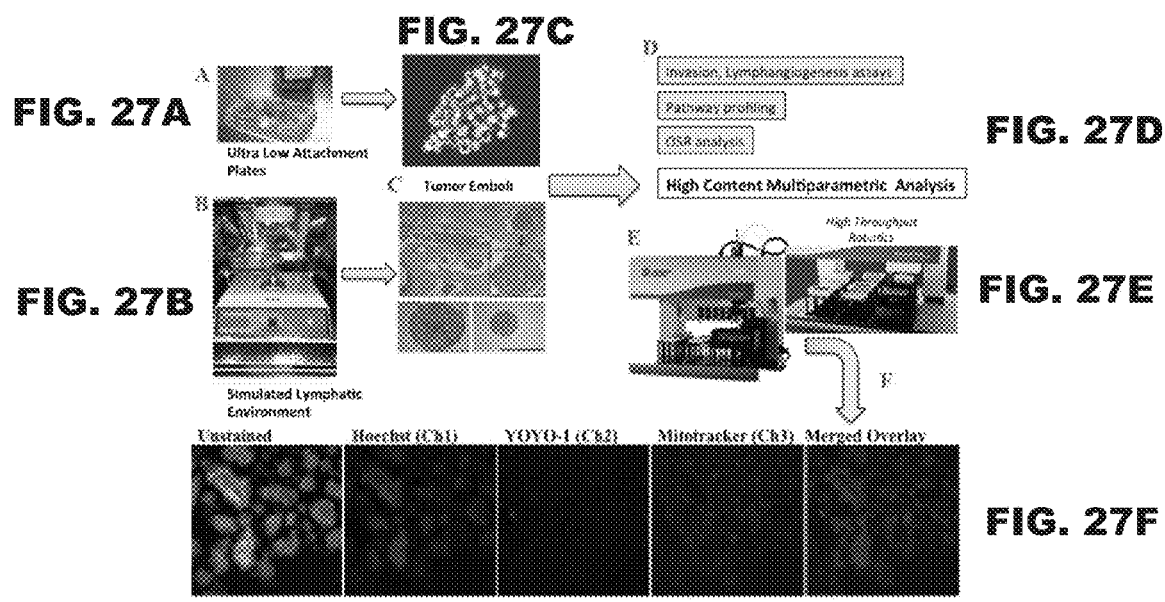

USE OF DISULFIRAM FOR INFLAMMATORY BREAST CANCER THERAPY

CROSS-REFERENCES TO RELATED APPLICATIONS

This application is related to, claims priority to, and incorporated herein in its entirety by reference U.S. Provisional Patent Application No. 62/160,791, filed May 13, 2015.

STATEMENT REGARDING FEDERALLY SPONSORED RESEARCH

N/A

BACKGROUND OF THE INVENTION

1. Field of the Invention

This invention relates to compositions of matter and methods for treatment of breast cancer, specifically inflammatory breast cancer.

2. Description of the Related Art

Inflammatory breast cancer (IBC) is one of the most aggressive forms of disease that presents with a unique pathobiology in which hyperproliferative clusters, or tumor emboli, are formed (Robertson et al., 2010). IBC is a distinct subtype of advanced breast cancer which disproportionately affects younger women of childbearing age (Robertson et al. 2010). A critical clinical challenge is that there are very few therapeutic options for IBC patients with metastatic recurrence (Robertson et al. 2010). Due to its high metastatic potential and frequent occurrence of therapeutic resistance, the prognosis remains poor with a 3-year survival of ~40% despite progress in multimodality treatment (Masuda et al., 2014). Following trimodal therapy including neoadjuvant chemotherapy (CT), surgery, and post-operative radiation, patients with IBC are more likely to have residual disease and have a significantly higher risk of recurrence (Rueth et al., 2014; Saigal et al., 2013). Both residual disease and recurrence following what appears to have been clearance of the tumor are a direct result of resistant cells that are able to survive these anticancer therapies. One of the hallmarks of this disease is engorgement of the dermal lymphatics on the chest wall. Morbidities associated with local recurrence include: pain, ulceration, odor, bleeding, lymphedema and the psychological distress of having visible local disease. These changes in the chest wall are due to the presence of clusters of tumor cells that invade skin lymphatics and lymph nodes. It is postulated that the tumor emboli or tumor emboli drive metastasis in this aggressive cancer type (Nguyen et al. 2006; Vermeulen et al. 2010).

Therapeutic resistance is a serious problem for the IBC population, and new molecular therapeutic targets need to be identified to improve treatment and increase patient survival. Further, IBC can serve as a model for studying the role of cellular oxidative stress responses in modulating the efficacy of anti-cancer therapies.

SUMMARY OF THE INVENTION

This disclosure provides pharmaceutical compositions and methods for treatment of breast cancer, including IBC, as described in the specification and claims herein.

In one aspect, the present disclosure provides a method of treating breast cancer in a patient, the method comprising administering an effective amount of a pharmaceutical composition comprising at least one redox modulating agent to treat the patient with breast cancer. In some aspects, the at least one redox modulating agent is disulfiram (DSF). In some aspects, the pharmaceutical composition comprises disulfiram (DSF) and copper (Cu) in an effective amount to treat breast cancer.

In another aspect, the disclosure provides a method of reducing or inhibiting breast cancer cell growth in a patient, comprising the step of administering a effective amount of a pharmaceutical composition comprising DSF to reduce, inhibit or prevent breast cancer cell growth.

In another aspect, the disclosure provides a pharmaceutical composition comprising an effective amount of at least one redox modulating agent to treat breast cancer.

In yet another aspect, the disclosure provides a pharmaceutical composition comprising an effective amount of the combination of disulfiram and copper to treat breast cancer.

These and other features, aspects, and advantages of the present invention will become better understood upon consideration of the following detailed description, drawings and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts a schematic of development of oxidative stress response (OSR) metagene in SUM149 cells, comparing untreated to $H_2O_2$ administration.

FIG. 1B depicts expression values of the "oxidative stress response" metagene set generated from $H_2O_2$-treated and untreated SUM149 cells; values are reported as a box plot according to the type of samples (normal breast, IBC, non-IBC). p-values are indicated (t-test).

FIG. 1C shows the classification of 389 breast cancer samples from left to right based upon decreasing metagene value; the IBC/non-IBC type is shown above the curve: black for IBC, white for non-IBC.

FIG. 1D depicts a heatmap showing expression values in BC samples from C for the top 40 genes most differentially expressed. Genes ordered from top to bottom according to decreasing $log_2$-ratio. Each row represents a gene and each column a sample. Expression levels are depicted according to the color scale at the bottom left, and color saturation represents the magnitude of deviation from the median.

FIG. 4A shows DSF acts as an ionophore to induce Ctr1-independent Cu uptake. Cu content (ng) normalized to protein (mg) in SUM149 (white bars) and rSUM149 (black bars) treated with DSF alone or in combination with Cu measured by ICP-HRMS. *$p<0.05$, **$p<0.005$.

FIG. 4B shows Ctr1 expression in normal and IBC cell lines. ←g indicates glycosylated form, ←t indicates truncated form. GAPDH as loading control.

FIG. 4C shows Viability of SUM149 cells treated with Ctr1-targeting siRNAs (black and gray bars) or control luciferase-targeting siRNA (white bars) following DSF (300 nM), Cu (10 μM), or DSF-Cu (100-300 nM, 10 μM) treatment for 24 h. on left. Immunoblot analysis of SUM149 cells treated with Ctr1-targeting siRNAs (A and B) or control luciferase-targeting siRNA on right.

FIG. 4D shows growth of SEY6210 and Ctr1/3-deficient MPY17 S. cerevisiae cells in YPEG media with addition of ZPT (left) or DSF (right) measured by absorbance at 600 nm.

FIG. 5A shows representative images of SUM149 mammospheres treated with DSF-Cu and demonstrates DSF-Cu inhibits AIG and ALDH activity of IBC cells. Magnification: 10×, inset: 20×.

FIG. 5B shows the quantification of AIG assay (by colony number) relative to untreated in SUM149 (white bars) and rSUM149 (black bars) cells treated with DSF, Cu (10 μM), or DSF-Cu complex.

FIG. 5C shows representative AIG images of cells treated as indicated.

FIG. 5D shows representative dot-plots of ALDH1 activity. Cells were incubated with ALDEFLUOR substrate (BAAA), and the specific inhibitor of ALDH1, DEAB, was used to establish the baseline fluorescence and define ALDEFLUOR-positivity (gated population). DEAB-treated plots are labeled as –ve ctrl. Mean±SEM of four independent experiments. Inset, Labeling of X and Y axes FIG. 6A shows DSF-Cu inhibits tumor growth in an in vivo model of IBC. Tumor volumes (measured $V=(L \times W^2)/2$) of mice with SUM149 subcutaneous flank tumors treated with vehicle, DSF, or DSF-Cu.

FIG. 6B shows representative immunoblot analysis of indicated proteins in tumor lysates from mice treated with vehicle, DSF, or DSF-Cu. GAPDH as loading control.

FIG. 6C shows representative images of tumor tissue from mice treated with vehicle, DSF, or DSF-Cu with TUNEL staining. Magnification: 40×.

FIG. 6D shows quantification of TUNEL positive cells (from 5C). Mean±SEM % TUNEL positive/total number of cells, *$p<0.05$.

FIG. 6E shows Cu content of excised tumors (ng) measured by ICP-HRMS relative to protein (mg).

FIG. 6F shows schematic representation of DSF-Cu mechanisms of action. DSF-Cu complex acts as a prooxidant, induces ROS-mediated cancer cell death by inhibiting NF-κB, which attenuates NF-κB-dependent antioxidant and anti-apoptotic gene expression. DSF-Cu inhibits ALDH1, which has been implicated in protection from ROS. DSF-Cu also inhibits the potent anti-apoptotic protein, XIAP, and translation initiation factor eIF4G1 (which can enhance XIAP translation during cell stress), promoting apoptosis.

FIG. 9 contains a list of antibodies, companies, catalog numbers, and dilutions used in this study.

FIG. 10 contains a list of 532 genes differentially expressed between $H_2O_2$-treated and untreated SUM149 cells FIG. 11 contains the statistics for mice used in the in vivo study. Tumor burden was determined by dividing tumor weight by final mouse weight; tumor doubling time was found by fitting a nonlinear regression model to tumor volumes in GraphPad Prism.

FIG. 27A shows a RTC/TE in vitro Model Flow Chart: FIG. 27A depicts using ultra-low attachment plates and specialized media.

FIG. 27B depicts the simulation of lymphatic shear stress and viscosity to mimic lymphatic microenvironment through addition of PEG or hyaluronic acid to normal growth media in a RTC/TE in vitro Model.

FIG. 27C are images showing TE formation in the RTC/TE in vitro Model (Lehaman, 2013).

FIG. 27D depicts this HCA TE system can be modified for a variety of in vitro experiments including invasion, migration as well as expression analysis.

FIG. 27E depicts high-throughput liquid handling allows for rapid, economical screening of multiple compounds in dose-response for high content multiparametric analysis using the RTC/TE in vitro Model (FIG. 27F).

FIG. 27F depicts representative images of cells from the in vitro RTC/TE model that allows simultaneous measurement of: nuclear morphology (size, aspect ratio, texture—Hoechst), cell proliferation (Hoechst), cell viability (YOYO-1), and mitochondrial function (MitoTracker). For quantitative analysis, an initial threshold for the size of untreated wells is set as indicative of a stable TE and excludes small spheroids. The minimum area cutoff is also set for qualifying mammospheres as 1821 square microns. Fluorescence quantification and localization is determined using a ThermoFisher CellInsight NXT and 3-channel Cell Health Profiling protocol in HCS Screen software (ThermoFisher).

DETAILED DESCRIPTION OF THE INVENTION

Figure 2A:
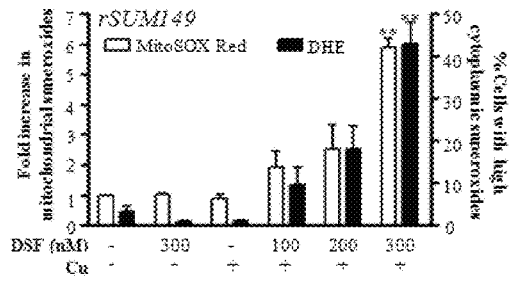
FIG. 2A depicts DSF-Cu reduces cellular antioxidant capacity to induce ROS and activate redox signaling. SUM149, rSUM149 cells treated with DSF, DSF+Cu (100-300 nM, 10 µM), Cu alone (10 µM) and fold induction of mitochondrial superoxides (white bars) and percentage of cells with high cytoplasmic superoxides (black bars) measured by flow cytometry.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a," "an," and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The present disclosure is based on the surprising discovery that IBC has an oxidative stress response (OSR) signature in surviving IBC cells after administration of an acute dose of an ROS inducer, and that redox modulators can target these surviving cells and result in a reduction or inhibition of breast cancer cell growth, spread or metastasis. The redox modulator includes disulfiram (DSF) alone or in combination with copper (Cu).

This disclosure provides a method of treating breast cancer in a patient, including inflammatory breast cancer. This method comprises administering an effective amount of a pharmaceutical composition comprising at least one redox modulating agent to treat the patient with breast cancer. In preferred aspects, the pharmaceutical compositions comprises DSF in combination with Cu.

The term "redox modulator" and "redox modulating agent" are used interchangeably herein and refer to an agent that can modulate the pathway induced by the oxidative stress response in cells.

The "treating" or "treatment" of breast cancer includes, but not limited to, reducing, inhibiting or preventing the growth of cancer cells, reducing, inhibiting or preventing metastasis of breast cancer cells and/or reducing, inhibiting or preventing one or more symptoms of breast cancer or metastasis thereof.

In some aspects, the pharmaceutical compositions comprise at least one redox modulating agent selected from the group consisting of disulfiram, manganese (MnP) porphyrin-based superoxide dismutase (SOD) mimics, and ribonucleotide reductase inhibitor Didox (DX; 3,4-Dihydroxy-benzohydroxamic acid) (Molecules for Health, Inc.).

In some aspects, the pharmaceutical compositions comprises at least one redox modulating agent, wherein the redox modulating agent is disulfiram (DSF). In some aspects, the pharmaceutical composition comprises DSF and copper. The DSF and copper are provided in an effective amount to treat the cancer. DSF forms a complex with copper (DSF-Cu) increasing intracellular copper concentration both in vitro and in vivo bypassing the need for membrane transport. DSF-Cu surprisingly provides anti-tumor efficacy for IBC. Not to be bound by any theory, DSF-Cu antagonize NFκB signaling, aldehyde dehydrogenase activity, and antioxidant levels, inducing oxidative stress-mediated apoptosis of cancer cells. DSF-Cu inhibits tumor/cancer growth without significant toxicity to non-tumor cells, specifically targeting tumor/cancer cells for apoptosis leading to a reduction, inhibition or prevention of tumor cell growth and/or metastasis.

The terms "tumor cell growth" or "tumor cell proliferation" are used herein interchangeably to refer to the increase in number of tumor cells.

Not to be bound by any theories, advanced breast cancer, such as IBC tumor, are highly redox adapted, which may render them resistant to ROS-inducing therapies (e.g., radiation and/or chemotherapy). DSF (alone or in combination with Cu), through redox modulation, may enhance chemo- and/or radio-sensitivity of these tumors that may be resistant to ROS-inducing therapies resulting in a reduction, inhibition or prevention of tumor cell growth and metastasis.

The terms "cancer" and "tumor" are used herein interchangeably. The terms "breast cancer" or "breast tumor" refer to or describe the physiological condition in mammals in which a population of cells are characterized by unregulated cell growth that originates in the breast tissue of the mammal. All stages of breast cancer are included, including primary cancer or a secondary (metastatic) lesions thereof. Examples of breast cancer include, but are not limited to, advanced stage breast cancer, inflammatory breast cancer, metastatic reoccurrence, secondary tumors originating from breast cancer, among others.

The term "subject suffering from breast cancer" refers to a subject that presents one or more symptoms indicative of a breast cancer (e.g., a noticeable lump or mass) and/or metastasis thereof, or has been diagnosed as having breast cancer or metastasis thereof.

The terms "effective amount" or "therapeutically effective amount" refer to an amount sufficient to effect beneficial or desirable biological and/or clinical results.

The term "metastasis" or "secondary tumor" refers to cancer cells that have spread to a secondary site, e.g., outside of the breast tissue. Secondary sites include, but are not limited to, the lymphatic system, skin, distant organs (e.g., liver, stomach, pancreas, brain, etc.) and the like.

In some aspects, the method of treating breast cancer comprises administering the pharmaceutical composition prior to, concurrently with, or after treatment with standard therapies. Suitable standard therapies include, but are not limited to, surgery (e.g. lumpectomy or mastectomy), radiation therapy (RT), and chemotherapy (CT), among others.

In some aspects, the pharmaceutical composition is administered in an effective amount increasing efficacy of radiotherapy or chemotherapy in the treatment of cancer in a patient. Suitable modes of chemotherapy are known by one skilled in the art. Chemotherapies include, but are not limited to, the anthracyclines (doxorubicin), taxanes (paclitaxel, docetaxel), alkylating agents, and platinum compounds (cisplatin, carboplatin), among others.

As described herein, in IBC metastasis, tumor cells that separate from the primary tumor mass form multicellular spheroids, termed tumor emboli, which then invade through the lymphatic system and reach distant organs to form secondary tumors. In some aspects, a method of reducing, inhibiting or preventing IBC tumor emboli formation is contemplated. The method comprises administering an effective amount of the pharmaceutical compositions provided here, including, for example, DSF alone or in combination with copper.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

In some aspects, methods of reducing, inhibiting or preventing breast cancer cell growth in a patient are provided. The method comprises administering an effective amount of the pharmaceutical compositions provided here, including, for example, a pharmaceutical composition comprising at least one redox modulating agent, e.g., DSF alone or in combination with copper, wherein the pharmaceutical composition is administered in an effective amount to reduce, inhibit or prevent breast cancer cell growth.

In some aspects, reducing, inhibiting or preventing breast cancer cell growth comprises inhibiting, reducing or preventing breast cancer cell proliferation, invasiveness of breast cancer cells, or breast cancer cell metastasis in a patient.

In some aspects, a method of inhibiting X-linked inhibitor of apoptosis protein (XIAP, also known as inhibitor of apoptosis protein 3 (IAP3)) expression in cancer cells is provided. XIAP is a potent mammalian caspase inhibitor and anti-apoptotic protein. The method comprises administering a pharmaceutical composition comprising at least one redox modulating agent preferably an agent that targets XIAP. Preferably, the redox modulating agent is DSF, alone or in combination with Cu. Not to be bound by any theory, but by targeting and downregulating XIAP in cancer cells, leads to an increase apoptosis of cancer cells and thus a reduction in tumor size, growth and metastasis.

In some aspects, the pharmaceutical compositions can be used to selectively increase the cell death of tumor cells within a patient, leading to a reduction in the size of tumors, inhibition of tumor growth and/or reduction or inhibition of metastasis.

In some aspects, methods of reducing therapeutically resistant residual tumor cells (RTC) in a patient suffering from IBC are described. The method comprises administering an effective amount of at least one redox modulating agent, for example, DSF alone or in combination with Cu. In some aspects, the RTC form tumor emboli (TE) in the patient and thus results in a reduction or inhibition of formation of TE.

Accordingly, some aspects of this invention is to overcome the limitations in IBC treatment, by providing a compositions and method for inhibiting the growth processes characteristic of cancer cells, including inhibiting invasiveness and metastasis, as well as inducing regression of primary tumors. The compositions and methods may induce cytotoxicity of cancer cells within the patient.

Aspects of the disclosure described with respect to the former method can be applicable to the latter method, and vice versa, unless the context clearly dictates otherwise.

The methods disclosed herein can include a conventional treatment regimen, which can be altered to include the steps of the methods described herein. The methods disclosed herein can include monitoring the patient to determine efficacy of treatment and further modifying the treatment in response to the monitoring. The methods disclosed herein can include administering a therapeutically effective amount of at least one redox modifying agent. The pharmaceutical compositions may further include a pharmaceutically acceptable carrier. The term "pharmaceutically acceptable carrier" refers any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents.

For parenteral administration, the active agent may be mixed with a suitable carrier or diluent such as water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Suitable amounts of DSF are able to be determined by one skilled in the art, and include, but are not limited to, a ranges from about 1 to about 1000 mg/day, suitably about 50 to 500 mg/day, for example, about 125-500 mg/day, alternatively about 250/500 mg/day, including any amounts and ranges inbetween.

Suitable forms of copper for administration are known to by one skilled in the art, and may depend on the mode of administration. Suitable forms of copper include, but are not limited to, copper gluconate, and the like [are there other suitable or preferred forms of copper?] Suitable dosages of copper include, but are not limited to, 0.1-10 mg/day, alternatively 0.5 mg-8 mg/day, for example, but not limited to, 1 mg/day, 2 mg/day, 4 mg/day, 6 mg/day, 8 mg/day and the like.

In IBC metastasis, tumor cells that separate from the primary tumor mass form multicellular spheroids, termed tumor emboli, which then invade through the lymphatic system and reach distant organs to form secondary tumors. Therefore, it is important to understand the cellular and molecular characteristics of tumor emboli in IBC for better drug development strategies to inhibit metastasis and improve patient survival. Currently, the only preclinical models available to study IBC tumor emboli are: Mary-X, an in vivo triple-negative xenograft model (Alpaugh et al. 1999) and in vitro tumor emboli derived from triple-negative SUM149 and HER-2 overexpressing SUM190 cells (Lehman et al. 2013; Mu et al. 2013). These models have predominantly been used for immunohistochemical analysis and assessment of viability of the tumor emboli as a whole after treatment with anticancer agents. However, current assays do not quantitatively measure cell morphology parameters of the 3D spheroids, both the individual cells that make up the spheroid and the spheroid as a whole.

Therefore, the present disclosure provides a reproducible, high content assay for the comprehensive, quantitative assessment of IBC tumor emboli morphology adapted for high-throughput analysis. The derived IBC cell lines can be used to simultaneously image multiple cell health characteristics of three dimensional (3D) IBC tumor emboli and quantitatively measure morphological parameters. This assay can further be used to determine the effects of cytotoxic compounds on IBC tumor emboli formation and individual tumor cell survival.

Aspects of the present disclosure that are described with respect to methods can be utilized in the context of the pharmaceutical compositions or kits discussed in this disclosure. Similarly, aspects of the present disclosure that are described with respect to the pharmaceutical compositions can be utilized in the context of the methods and kits, and aspects of the present disclosure that are described with respect to kits can be utilized in the context of the methods and compositions.

This disclosure provides kits. The kits can be suitable for use in the methods described herein. Suitable kits include a kit for treating breast cancer comprising a pharmaceutical composition comprising at least one redox modulating agent. In one aspect, the kit provides pharmaceutical composition comprising DSF and Cu in amounts effective for treating breast cancer. In some aspects, instructions on how to administer the pharmaceutical composition and/or active agents.

The following non-limiting examples are included for purposes of illustration only, and are not intended to limit the scope of the range of techniques and protocols in which the compositions and methods of the present invention may find utility, as will be appreciated by one of skill in the art and can be readily implemented.

Example 1. Disulfiram (DSF) Acts as a Copper Ionophore to Induce Copper-Dependent Oxidative Stress and Mediate Anti-Tumor Efficacy in Inflammatory Breast Cancer This example demonstrates using a cellular model of IBC, we identified an oxidative stress response (OSR) signature in surviving IBC cells after administration of an acute dose of an ROS inducer. Metagene analysis of patient samples revealed significantly higher OSR scores in IBC tumor samples compared to normal or non-IBC tissues, which may contribute to the poor response of IBC tumors to common treatment strategies, which often rely heavily on ROS induction.

This example also demonstrates using a potent redox modulator, the FDA-approved small molecule Disulfiram (DSF), alone and in combination with copper (Cu). DSF forms a complex with copper (DSF-Cu) increasing intracellular copper concentration both in vitro and in vivo, bypassing the need for membrane transporters. DSF-Cu antagonized NF-κB signaling, aldehyde dehydrogenase activity and antioxidant levels inducing oxidative stress-mediated apoptosis in multiple IBC cellular models. In vivo, DSF-Cu significantly inhibited tumor growth without significant toxicity, causing apoptosis only in tumor cells. These results indicate that IBC tumors are highly redox adapted, which may render them resistant to ROS-inducing therapies. DSF, through redox modulation, may be a useful approach to enhance chemo- and/or radio-sensitivity for advanced BC subtypes where therapeutic resistance is an impediment to durable responses to current standard of care.

Introduction

Oxidative stress is an imbalance between the levels of ROS within the cell and the antioxidant systems responsible for detoxifying ROS. Cancer cells are often characterized by increased levels of ROS due to metabolic and signaling aberrations (Gorrini et al., 2013); in order to compensate for high levels of ROS, cancer cells specially advanced subtypes survive by activating redox adaptive mechanisms including increased expression and activity of ROS-scavenging systems and antioxidants (Trachootham et al., 2009). Many anti-cancer regimens work at least in part through the generation of ROS, and thus may be rendered ineffective by redox adaptation. Chemotherapies including the anthracyclines (doxorubicin), taxanes (paclitaxel, docetaxel), alkylating agents, and platinum compounds (cisplatin, carboplatin) as well as radiation therapy all rely heavily on the induction of oxidative stress-induced apoptosis for their anti-tumor activities (Brown and Bicknell, 2001; Manda et al., 2009; Trachootham et al., 2009); thus, redox adaptation can confer resistance to many breast cancer therapies.

Therapeutic resistance is a serious problem for the IBC population, and new molecular therapeutic targets need to be identified to improve treatment and increase patient survival.

Further, IBC can serve as a model for studying the role of cellular oxidative stress responses in modulating the efficacy of anti-cancer therapies.

Gene expression analyses show that IBC tumors have elevated expression of the redox-sensitive nuclear transcription factor NF-κB, and related survival signaling pathways compared to non-IBC tumors (Iwamoto et al., 2011; Nguyen et al., 2006; Van Laere et al., 2006). Pre-clinical evidence in cellular models of IBC indicates that redox adaptation through enhancement of cellular antioxidant capacity can confer therapeutic resistance to a number of drugs including classical ROS inducers, chemotherapeutics, and targeted agents (Aird et al., 2012; Allensworth et al., 2012; Williams et al., 2013). We hypothesize that redox adaptation via enhancement of the oxidative stress response plays a significant role in therapeutic resistance in the IBC patient population; thus, to overcome resistance, induction of ROS must be accompanied by rational targeting of those adaptive mechanisms.

Disulfiram (DSF), a member of the dithiocarbamate family, is an FDA-approved drug for alcoholism which can react with redox-sensitive sulfhydryl groups (thiols) and bind copper (Cu) (Hogarth, 2012), an essential cofactor for the key cellular enzymes (e.g. cytochrome c oxidase and superoxide dismutase 1 (SOD1)) involved in oxidative stress response (Fraga, 2005). Notably, DSF is a redox modulator whose induction of ROS is enhanced by the addition of Cu (Yip et al., 2011), and it has been reported to inhibit the activity of NF-κB (Wang et al., 2003; Yip et al., 2011), a potential mediator of redox adaptation in IBC. These properties highlight DSF as an attractive agent by which to enhance cancer cell death and enhance therapeutic sensitivity in IBC.

This example analyzed a cohort of IBC and non-IBC pre-treatment biopsies using an oxidative stress response (OSR) metagene generated by analyzing the genes activated and repressed in IBC cells in culture that mount a successful protective response to an ROS inducer. IBC patient samples exhibited significantly higher OSR scores, indicating an enhancement of protective mechanisms that enables them to survive an onslaught of ROS, i.e. redox adaptation. This example further includes mechanistic studies in both cellular and animal models of IBC to provide strong evidence that DSF, in conjunction with Cu, targets tumor redox adaptation to reverse therapeutic resistance and supports the use of DSF as a novel anti-cancer drug in IBC.

Materials and Methods 2.1 Gene Expression Profiling of $H_2O_2$-Treated SUM149 Cell Lines and Clinical Samples Messenger RNA triplicates of SU1V1149 cells treated with or without $H_2O_2$ were profiled using the Affymetrix HGU133A2 GeneChip at Duke University Institute for Genome Sciences and Policy Microarray Facility. Raw expression data were background-corrected, normalized, and summarized using Robust Multiarray Averaging method taking into account probe sequence information (GCRMA). Normalized data were filtered to include only probe sets that showed expression above $\log_2(100)$ in at least 2/6 expression profiles, resulting in 9,962 informative data points. Differential gene expression analysis between treated and untreated cells was performed using linear regression models implemented in the limma package of BioConductor in R. P-values were corrected for false discovery rate (FDR) using the Benjamini and Hochberg correction. Probe sets were considered significant if the nominal p-value was smaller than 0.05, the FDR-adjusted P-values smaller than 0.1, and the fold change (ratio SUM149 cells $H_2O_2$-treated versus untreated) higher than |2|. A metagene signature designated "oxidative stress response" (OSR) was generated from the resulting gene list and defined for each sample as follows: ratio between average expression level of genes upregulated and average expression level of genes downregulated in $H_2O_2$-treated cells. This classifier was applied to a series of 389 pre-treatment IBC and non-IBC samples previously described (Bertucci et al., 2013; Van Laere et al., 2013). Those samples were obtained from pre-treatment biopsies from patients treated in three institutions: Institut Paoli-Calmettes (IPC, Marseille, France: 71 IBC and 139 non-IBC), MD Anderson Cancer Center (MDA, Houston, Tex., USA: 25 IBC and 58 non-IBC), and General Hospital Sint-Augustinus (TCRU, Antwerp, Belgium: 41 IBC and 55 non-IBC). Patients with IBC were selected by strictly adhering to the consensus diagnostic criteria published by Dawood and colleagues (Dawood and Cristofanilli, 2011). Each patient gave written informed consent, and this study was approved by the institutional review boards of all 3 participating centers. The normal breast samples series contained 21 samples extracted from the GEO public database (GSE31448, GSE16873, GSE21422). Before applying the metagene signature, Empirical Bayes normalization method with inSilicoMerging package (Taminau et al., 2012) was applied to merge all expression data sets and remove interstudy bias; correct normalization was checked using PCA (data not shown). The molecular subtype of tumors was based on the ER, PR and HER2 statutes (Bertucci et al., 2013; Van Laere et al., 2013) as follows: hormone receptor (HR)+/HER2− for ER and/or PR+ and HER2− samples, HER2+ for HER2+ samples, and triple negative (TN) for ER−/PR−/HER2− samples. A metagene score was calculated based upon the genes common to the signature and all data sets after background filtering. In addition, we tested the relationship between the IBC/non-IBC phenotype from our 389-sample series and another "oxidative stress" expression signature represented by the 84-gene list from the Human Oxidative Stress RT2 Profiler PCR Array (Qiagen). Fifty-five out of 84 genes were present in our data set and retained after background filtering, and used to classify the 389 samples by unsupervised analysis (Principal Component Analysis, PCA). We then defined the "Qiagen oxidative stress" metagene as the first component of PCA and compared its distribution between IBC and non-IBC.

2.2 Cell Culture

SUM149 and SUM190 cells were obtained from Asterand, Inc. and cultured as described previously (Aird et al., 2008). Asterand routinely characterizes cell lines by short tandem repeat polymorphism analysis. Cells were banked upon receipt and cultured for no more than 6 months before use in any assay. rSUM149 and rSUM190 are isogenic acquired resistance models established in the laboratory (Aird et al., 2010). MDA-IBC-3 cells were kindly provided by Dr. Woodward (MD Anderson Cancer Center) and cultured as described (Klopp et al., 2010).

2.3 Trypan Blue Viability Assay

Cells were treated for 24 h in regular growth medium with Disulfiram (Sigma), $CuSO_4$ (VWR), SOD mimetic (MnTnHex-2-PyP$^{5+}$), bathocuproine disulfonate (BCS, Sigma), and tetrathiomolybdate (TM, Sigma). Cell viability was determined by trypan blue exclusion as described previously (Aird et al., 2008) where % viability was calculated as live cells/total cells×100.

2.4 Western Immunoblotting

Cell lysates were harvested after treatment with DSF±Cu for 24 h. Membranes were incubated with primary antibodies against XIAP, SOD2 (BD Bioscience), SOD1, PARP, eIF4G1, p38, ERK1/2 (p44/42 MAPK), NF-κB (p65 subunit) (Cell Signaling Technologies), Ctr1 (Nose et al., 2006), actin, or GAPDH (Santa Cruz Biotechnology Inc.) overnight at 4° C. as described previously (Aird et al., 2008). Additional information about antibodies used in this study is provided in Supplementary Table 1. Stripping of membranes to detect total protein was done as previously (Aird et al., 2010). Densitometric analysis was conducted using NIH ImageJ software (Abramoff, 2004).

2.5 Measurement of ROS

Mitochondrial (Mitosox Red) and cytoplasmic (DHE) ROS were measured as described previously (Aird et al., 2012). Cells were treated with DSF±Cu for 24 h, harvested, and analyzed by flow cytometry. 25,000 events were collected on a FACSCalibur (Becton Dickinson) flow cytometer and analyzed using Cellquest (Becton Dickinson). For DRE, high fluorescence was calculated by setting a gate on control cells where the peak reached a minimum; experimental samples were compared to this control.

2.6 Glutathione Assay

Reduced glutathione levels were assessed as described previously (Aird et al., 2012) using the GSH-Glo Glutathione Assay (Promega) according to manufacturer's instructions.

2.7 Nrf2 Activity Assay

Cells in opaque 96-well plates (Greiner Bio-One) were transfected with pGL4.37 (ARE firefly luciferase reporter, Promega) and pGL4.75 (Renilla luciferase control, Promega) plasmids using a 3:1 ratio of Xtremegene HP (Roche Applied Science, Indianapolis, Ind.) to DNA. The next day, cells were treated with as indicated. After 24 h, the Dual-Glo Luciferase Assay System (Promega) was used and luminescence read on a Veritas microplate luminometer (Turner BioSystems). Firefly luminescence was normalized to Renilla luminescence for each sample, and this value normalized to untreated.

2.8 Measurement of Cell-Associated Cu in Cell Lysates and Murine Tumor Tissue

Cell lysates were prepared as above. For tumors, a portion of each tumor was placed into tissue lysis buffer (GoldBio Technology) and homogenized using the Bullet Blender Storm and lysis beads (MidSci). Lysates were analyzed for Cu content using a Thermo Scientific Element 2 inductively coupled plasma high-resolution mass spectrometer (ICP-HRMS) at the W. M. Keck Elemental Geochemistry Laboratory (University of Michigan, Ann Arbor, Mich.), and Cu content of lysis buffer blank was subtracted from each sample. Values were normalized to protein for reporting as ng Cu/mg protein.

2.9 Ctr1 Knockdown

A luciferase-targeting control or Ctr1-targeting siRNAs (A and B, Invitrogen) were transfected into cells using Dharmafect 1 reagent (Thermo Scientific). 24 h post-transfection, DSF, Cu, or DSF-Cu was added and cells were harvested for trypan blue staining and western immunoblotting to confirm knockdown after 24 h.

2.10 Complementation of *Saccharomyces Cerevisiae* $Cu^+$-transport Mutants

SEY6210 (wild type) (Robinson et al., 1988) and ctr1/ctr3Δ mutant MPY17 *S. cerevisiae* cells (Pena et al., 1998) were grown in YPEG media (3% ethanol, 3% glycerol, 1% yeast extract, 2% Bacto Peptone, 2% agar) with addition of 0-50 μM known Cu ionophore, zinc pyrithione (ZPT) (Reeder et al., 2011), or DSF. Cells were allowed to grow at 30° C. for 3 days; growth was assessed by measuring optical density at 600 nm on a Spectramax Plus 384 plate reader (Molecular Devices).

2.11 ALDEFLUOR Assay

ALDH enzymatic activity was assessed using the ALDEFLUOR kit (Stem Cell Technologies) according to the manufacturer's instructions. Briefly, cells were incubated with ALDH substrate for 35 minutes at 37° C. The specific ALDH inhibitor diethylaminobenzaldehyde (DEAB) was used as negative control. Sorting gates were established using 7-AAD stained cells for viability and ALDEFLUOR-stained cells treated with DEAB as negative controls. Dot plots from a representative experiment are shown with mean±SEM from four experiments.

2.12 Mammosphere Growth

Matrigel was applied to 24-well plates at 150 μL/cm$^2$ and incubated at 37° C. for 30 min to allow gel to solidify, after which 25,000 cells were seeded. After overnight incubation, treatments were applied for 24 h; images were recorded using a Motic AE2000 microscope, M14 camera, and Infinity Capture (Lumenera) software.

2.13 Anchorage-Independent Growth Assay

AIG was measured as previously described (Allensworth et al., 2013). Images of representative fields were taken with 5× magnification using a Zeiss Axio Observer microscope, Hamamatsu Orca ER digital camera, and MetaMorph software (Molecular Devices).

2.14 Human Breast Tumor Xenograft Studies

Female SCID mice were obtained from a breeding colony at the Cancer Center Isolation Facility at Duke University. All experiments were performed in accordance with the Duke University International Animal Care and Use Committee. SUM149 cells ($1\times10^6$) were suspended in 50 μL PBS/50 μL Matrigel and injected into the flank subcutaneously. Once tumors were palpable (50-60 mm$^3$ volume or approximately 4.5-5 mm length or width), mice were randomly assigned to treatment groups: vehicle control (V=5% DMSO, 5% EtOH, 90% corn oil), DSF (50 mg/kg in V), or combination of DSF in V and Cu (0.5 mg/kg) in saline (n=5-6). Animals were treated daily via intraperitoneal injection, and tumor volume measured using the formula V=(L×W$^2$)/2 where L is length and W is width of the tumor. Tumor growth inhibition was calculated using the formula: TGI=(1−(T/V))*100, where T is mean tumor volume for DSF-Cu or DSF and V is mean tumor volume for vehicle. When control tumors reached humane endpoint, the experiment was terminated and all mice were sacrificed. Tumors were removed, and tissue was harvested for H&E staining, TUNEL assay, western immunoblotting, and Cu measurement.

2.15 TUNEL Staining of Murine Tumor Tissue

Tumor xenografts were fixed in 10% formalin, processed and embedded in paraffin. Serial sections were cut and deparaffinized in a series of 100%, 95% and 70% ethanol for 5 min each and washed in 1×PBS. Sections were incubated with 20 μg/mL Proteinase K solution (Roche Diagnostics) for 15 min at 25° C. After 2 washes in 1×PBS, sections were incubated with In Situ cell death enzyme as per manufacturer's instructions (In Situ Cell Death Detection Kit, Roche). Sections were coverslipped and mounted with Prolong Anti-fade mounting medium with DAPI (Invitrogen), imaged using the Zeiss Axio Imager microscope, and analyzed with Metamorph and ImageJ software.

2.16 Statistical Analysis

The statistical analyses were conducted using GraphPad Prism (GraphPad Software, Inc.) Student's 2-tailed t-test and Fisher's exact test. Differences were considered significant at $p<0.05$.

3. Results 3.1 Altered Oxidative Stress Response in IBC Versus Non-IBC Clinical Samples This Example defined an oxidative stress response (OSR) signature by performing a supervised analysis comparing expression profiles of untreated SUM149 cells with SUM149 cells challenged with an acute 1 h exposure to 500 µM $H_2O_2$. Following $H_2O_2$ exposure, the cells were allowed to recover for 24 h, and then the OSR response was analyzed in the surviving tumor cells. 642 differentially expressed probe sets representing 532 genes, 248 genes upregulated and 284 downregulated, were identified in response to $H_2O_2$ challenge and recovery (FIG. 1A). A metagene set designated "oxidative stress response" (OSR) was generated from this gene list (521 out of 532 genes retained after filtering), with genes upregulated including NF-κB targets, antioxidants, heat shock proteins, DNA damage repair systems, and many others previously validated as participants in the oxidative stress response (FIG. 10).

Not to be bound by any one theory, to investigate our hypothesis that IBC tumors are inherently more resistant to ROS-mediated cancer therapies as a result of an enhanced oxidative stress response, we applied the OSR metagene to gene expression data from 137 IBC patients and 252 non-IBC patients treated across three centers as well as 21 normal breast samples. All BC samples were from diagnostic biopsies taken before systemic therapeutic intervention. As shown in FIG. 1B, OSR metagene values were higher in BC patient tissues (both IBC and non-IBC) than in normal breast samples (p=2.35E-06 for IBC vs normal), and IBC samples exhibited significantly higher OSR values than non-IBC samples (p=1.54E-04). FIG. 1C shows an enrichment of IBC tumors among the BC samples that display a higher metagene value and conversely, an enrichment of non-IBC tumors among the breast cancer samples that display a lower value (p=3E-03; Fisher's exact test). FIG. 1D shows the heatmap built from the 40 most differentially expressed genes out of 521. Per molecular subtype, we found that the OSR metagene was significantly higher in IBC than in nIBC in the HR+/HER2− subtype (p=0.026) and the HER2+ subtype (p=9.7E-04), whereas there was no significant difference in the TN subtype (p=0.23) (data not shown). In order to validate the findings of our OSR metagene, we compared the distribution of values between IBC and non-IBC in a metagene set from Qiagen, which includes 55 genes that are known to regulate oxidative stress response in multiple cell types. Here again, IBC showed significantly higher metagene values than non-IBC (p=0.01; Student's t-test; data not shown), indicating that the pronounced activation of the oxidative stress response observed with the 521-gene signature does not depend on the fact that this signature was identified in a preclinical model of IBC. Together, these results support a general enhancement of the oxidative stress response in BC cells compared to their normal counterparts, indicative of redox adaptation. Within BC, IBC tumors are characterized by an especially strong activation of this protective regimen, which may contribute to therapeutic resistance, residual disease, and high rate of recurrence following treatment. Therefore, advanced breast cancer like IBC is likely to benefit significantly from the addition of a redox modulatory therapy that targets mediators of the oxidative stress response.

Figure 2B:
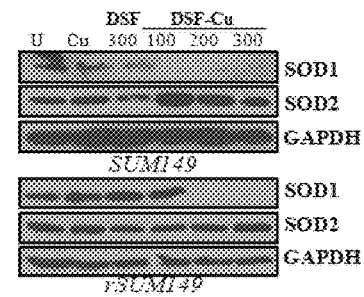
FIG. 2B depicts the immunoblot analysis of SOD1/2.
Figure 2C:
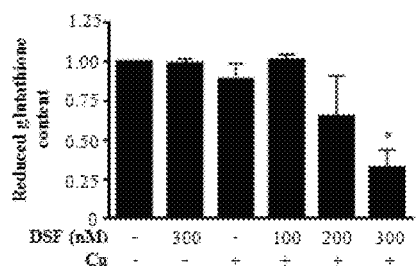
FIG. 2C depicts the reduced glutathione content relative to untreated (rSUM149 shown).
Figure 2D:
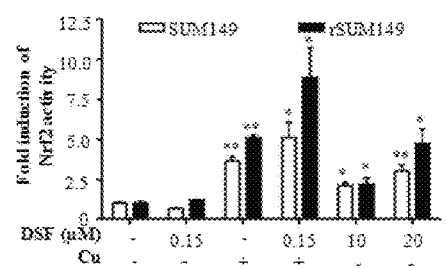
FIG. 2D depicts the fold induction of Nrf2 activity measured by ARE-responsive luciferase activity.
Figure 2E:
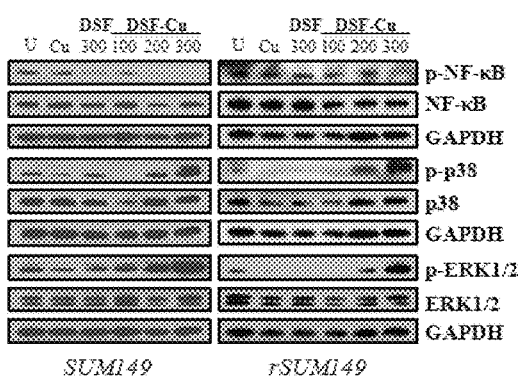
FIG. 2E depicts the immunoblot analysis of indicated proteins in treated cells at 4 h time point.
Figure 2F:
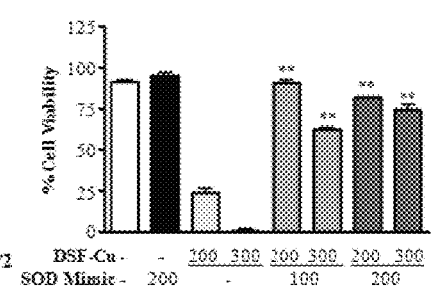
FIG. 2F depicts the effect of SOD mimetic (MnTnHexyl-2-Pyp$^{5+}$, 100-200 µM) on viability measured by trypan blue exclusion assay (rSUM149 shown). *p<0.05, **p<0.005 in all panels. GAPDH and respective total proteins as loading controls.

3.2 A Novel Redox Modulatory Strategy (DSF-Cu) Overcomes the OSR in Therapy-Resistant IBC Cells Having determined that the oxidative stress response is especially strong in IBC patient samples, we next sought to discern whether targeting this system could enhance ROS-induced therapeutic cell death in these aggressive tumors. For this purpose we selected DSF, a redox modulator that can react with protein thiols, bind Cu, and has been reported to inhibit NF-κB. We characterized the effects of DSF alone and in combination with exogenous Cu on ROS generation and downstream redox signaling in therapy-resistant, redox-adapted rSUM149 cells [isogenic clonal derivatives (Aird et al., 2010) of well-established, triple-negative SUM149 IBC cell line show increased tolerance to ROS-inducing agents ($H_2O_2$, paraquat), kinase inhibitors (lapatinib, sorafenib, sunitinib, gefitinib) and chemotherapies (including taxanes, vinca alkaloids, capecitabine, mitoxantrone, mitomycin C, and anti-aromatases) (Williams et al., 2013). Data in FIG. 2A show that DSF-Cu induced significant levels [comparable to levels in SUM149 cells exposed to ROS-inducing agents (Aird et al., 2012; Evans et al., 2013)] of mitochondrial (white bars) and cytoplasmic (black bars) superoxide radicals compared to DSF or Cu alone. Increased ROS corresponded with decreased superoxide dismutase 1 (SOD1) expression (FIG. 2B) and decreased levels of GSH (rSUM149 shown), the most potent cellular ROS scavenging system (FIG. 2C). We then investigated the effects of DSF-Cu on activity of Nrf2 and NF-κB redox-responsive transcription factors (Bellezza et al., 2010). FIG. 2D shows that Cu (10 µM) and high-dose DSF (10-20 µM) induced Nrf2 transcriptional activity; however, the strongest induction was observed with low dose DSF-Cu (150 nM, 10 µM). DSF-Cu decreased NF-κB phosphorylation within 4 h following treatment (FIG. 2E), and this reduction was sustained 24 h post-treatment (Suppl. FIG. S1). The ROS increase also corresponded with increased phosphorylation of p38 MAPK and ERK1/2 (FIG. 2E). Incubation of cells with an exogenous SOD mimetic (MnTnHexyl-2-PyP$^{5+}$) with potent antioxidant activity blocked cell death caused by DSF-Cu treatment (FIG. 2F, gray bars, rSUM149 shown), confirming the pro-oxidant role of DSF-Cu in inducing cell death in redox-adapted rSUM149 cells.

3.3 DSF-Cu Induces Cell Death Corresponding with XIAP and eIF4G1 Downregulation

The next experiment compared the effect of DSF and DSF-Cu on viability of multiple BC cell lines. DSF induced cell death only at higher micromolar concentrations (FIG. 3A: SUM149—left, squares, $IC_{50}$~17 µM; rSUM149—right, squares, $IC_{50}$~25-30 and Cu alone was not cytotoxic. DSF's potency was significantly enhanced by addition of 10 µM Cu (DSF-Cu), with approximately 100-fold decrease in $IC_{50}$ values in SUM149 and rSUM149. Remarkably, DSF-Cu caused cell death in redox-adapted rSUM149 cells at levels comparable to parental redox-sensitive SUM149 cells. DSF-Cu has been found to be non-toxic to normal, immortalized breast cells (MCF10A) at up to 20 µM (Chen et al., 2006). In addition, similar to SUM149 cells, DSF-induced cell death by Cu was observed in other IBC cell lines tested (Suppl. FIG. S2), which included MDA-IBC-3 (Her2-overexpressing), SUM190 (Her2-overexpressing, ROS sensitive), and rSUM190 (isogenic derivative of SUM190 with therapeutic resistance, redox adaptation). SUM190 cells were highly sensitive to DSF-Cu treatment even at very low DSF concentrations. Comparison with other nonIBC cell lines revealed that similar to IBC cells, addition of Cu to DSF induced cell death at similar dose range of DSF and Cu doses tested albeit with a fold higher potency in SUM149 cells compared to T47D, MDA-MB436 and MDA-MB-468 (data not shown).

Figure 3A:
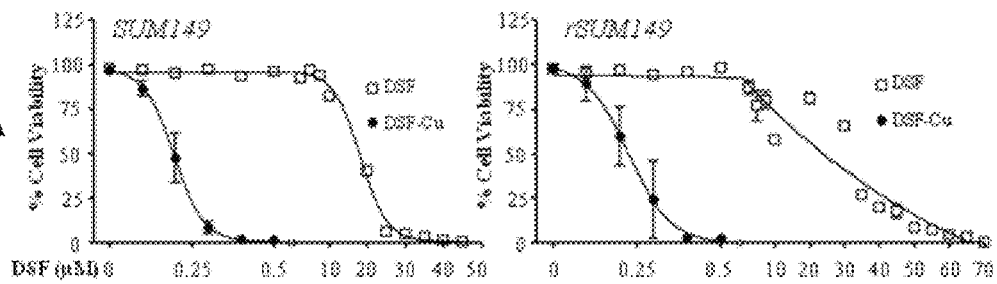
FIG. 3A depicts DSF induces Cu-dependent apoptosis and shows dose-dependent measurement of viability in cells treated with DSF, Cu (10 μM), or DSF-Cu.
Figure 3B:
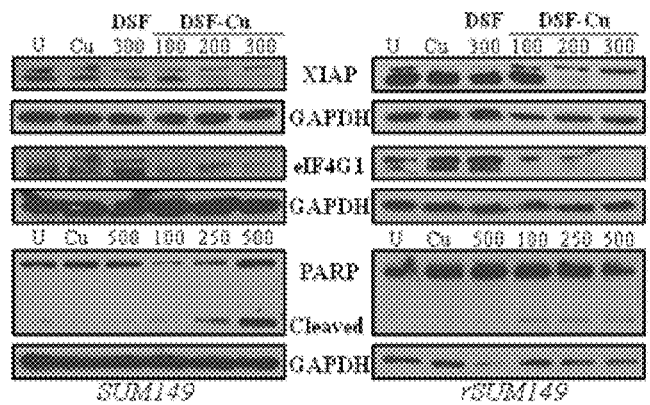
FIG. 3B depicts an immunoblot analysis of apoptotic pathway proteins. GAPDH as loading control.

Decrease in IBC cell viability in the presence of DSF-Cu correlated with decreased levels of XIAP, considered the most potent mammalian caspase inhibitor and anti-apoptotic protein (FIG. 3B). This is consistent with the fact that oxidative stress can trigger the intrinsic apoptotic pathway, and our previous studies identified that XIAP overexpression in IBC cells correlates with resistance to therapeutic apoptosis (Aird et al., 2008; Aird et al., 2010; Allensworth et al., 2012). Further, DSF-Cu-mediated cell death was associated with decreased expression of eIF4G1 (a disease progression factor identified in IBC tumors (Silvera et al., 2009)) and increased PARP cleavage (FIG. 3B). Together, these data suggest that induction of apoptotic cell death is a primary mode of action of DSF-Cu.

Figure 3C:
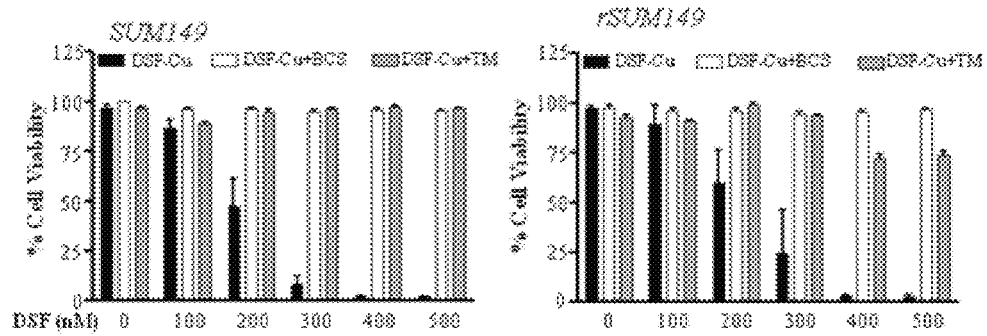
FIG. 3C depicts the viability in the presence of Cu chelators bathocuproine disulphonate (BCS, 100 μM, white bars) or tetrathiomolybdate (TM, 10 μM, gray bars) measured by trypan blue exclusion assay.
Figure 7:
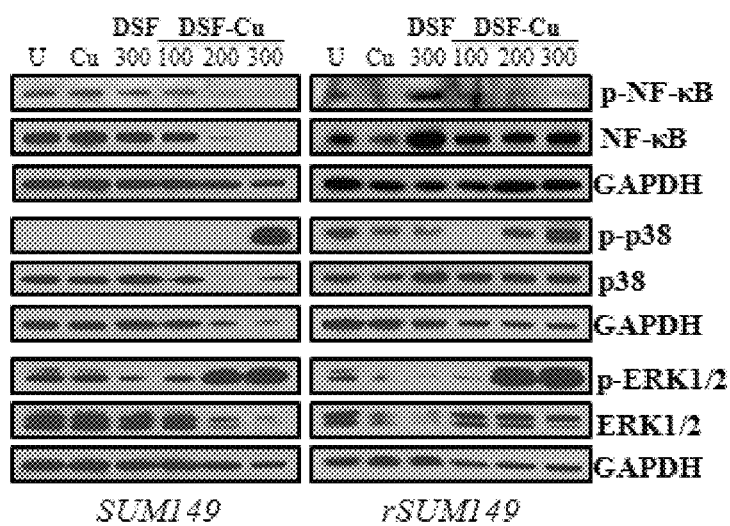
FIG. 7 depicts immunoblot analysis of phosphorylation status of indicated proteins in SUM149 and rSUM149 cells treated with DSF (100-300 nM), Cu (10 μM), or DSF-Cu (100-300 nM, 10 μM) for 24 h. Respective total proteins and GAPDH as loading controls.
Figure 8A:
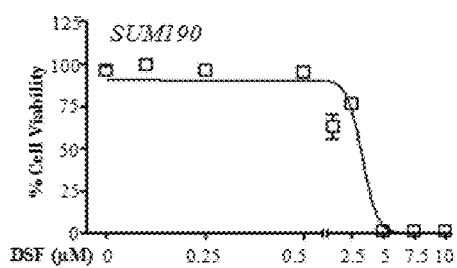
FIG. 8A shows the viability of SUM190 IBC cells treated with DSF (0-70 μM, squares), Cu (10 μM) or DSF-Cu (100-500 nM, 10 μM, circles) measured by trypan blue exclusion assay. DSF-Cu is not shown for SUM190 as the combination resulted in 0% cell viability at all doses test (as low as 50 nM DSF, 10 μM Cu).
Figure 8B:
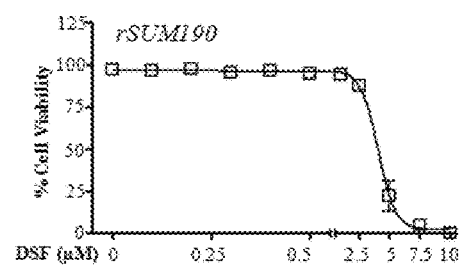
FIG. 8B shows the viability of rSUM190 IBC cells treated with DSF (0-70 μM, squares), Cu (10 μM) or DSF-Cu (100-500 nM, 10 μM, circles) measured by trypan blue exclusion assay. DSF-Cu is not shown for rSUM190 as the combination resulted in 0% cell viability at all doses test (as low as 50 nM DSF, 10 μM Cu).
Figure 8C:
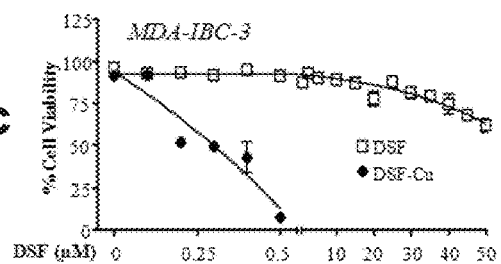
FIG. 8C shows the viability of MDA-IBC-3 IBC cells treated with DSF (0-70 μM, squares), Cu (10 μM) or DSF-Cu (100-500 nM, 10 μM, circles) measured by trypan blue exclusion assay.

To determine whether the interaction between DSF and Cu is necessary for DSF's mechanism of action, we evaluated the impact of disrupting the DSF-Cu interaction using high affinity chelators to sequester free Cu. Addition of bathocuproine disulphonate (BCS, white bars) (Cen et al., 2004), or tetrathiomolybdate (TM, gray bars) (Brewer, 2009) almost completely blocked DSF-Cu-induced cell death (black bars) SUM149 (FIG. 3C, left) and rSUM149 (FIG. 3C, right) cells, highlighting the importance of Cu binding for enhancement of DSF's cytotoxic effects. While TM has been previously reported to induce cancer cell death through its ability to sequester Cu (Brewer, 2009), the TM-Cu mixture was without effect in these models of IBC. These data confirm that the activity of DSF is not related to Cu sequestration, but rather a gain of function that results in increased ROS production.

3.4 DSF is a Cu Ionophore that Induces Ctrl-Independent Cu Accumulation in IBC Cells.

Given that Cu interacts with DSF, and this interaction is necessary for cytotoxicity, it was of interest to address whether DSF affects Cu accumulation in IBC cells. A slight increase in Cu accumulation at 24 h, measured by ICP-HRMS, was observed upon treatment with 10 μM Cu; however, there was a dramatic dose-dependent increase in cell-associated Cu following treatment with DSF-Cu, with up to a 30-fold increase at the maximum concentration tested (FIG. 4A). Analysis of protein levels of the Cu transporter Ctrl, which tightly regulates Cu import, revealed expression (FIG. 4B) in mammary epithelial cells (HME1), normal-like MCF10A cells, and the IBC cell lines (SUM149, rSUM149, SUM190, MDA-IBC-3). rSUM149 cells expressed Ctrl at much lower levels than SUM149, but notably, Cu accumulation in the presence of DSF (FIG. 4A) was similar in SUM149 and rSUM149 cells irrespective of Ctrl expression status. These findings suggest that transport via the classical cellular Ctrl mechanism may not play a significant role in DSF-mediated Cu accumulation. To investigate the possibility that DSF may promote cellular uptake of Cu in a Ctrl-independent fashion, two Ctrl-targeting siRNAs were used to knock down expression of the Cu transporter in SUM149 cells (FIG. 4C, right). Assessment of viability revealed that Ctrl knockdown (FIG. 4C, left, black and gray bars) does not change the sensitivity of SUM149 cells to DSF (FIG. 4C, left, white bars).

In addition, to further evaluate the Cu ionophore activity of DSF, we took advantage of a novel yeast model. We examined the growth of wild type S. cerevisiae (SEY6210) and a ctr1/ctr3Δ mutant (MPY17) lacking both high affinity Cu transporters (yeast express Ctrl and Ctr3, while humans have only Ctrl) (Pena et al., 1998) in YPEG media, where Cu is required for growth. Data in FIG. 4D show that while wild type SEY6210 cells (white bars) grew well in YPEG due to their ability to take up trace levels of Cu from the media, the ctr1/ctr3Δ MPY17 cells (black bars) did not. However, in the presence of the known Cu ionophore zinc pyrithione (ZPT) (Reeder et al., 2011), MPY17 cells grew similarly to the SEY6210 cells. In this assay, the addition of DSF to MPY17 cells enhanced their growth similar to ZPT treatment. These results strongly support that DSF acts as a Cu ionophore in a Ctrl-independent manner leading to DSF-Cu mediated cell death in IBC cells.

3.5 DSF-Cu Inhibits Anchorage-Independent Growth and ALDH1 Activity in IBC Cells Because SUM149 cells can form mammospheres (Debeb et al., 2012) and therapeutic response of 3D cultures is generally more indicative of in vivo activity, the effects of DSF, Cu, and DSF-Cu on 3D IBC structure were assessed. We observed ablation of IBC cell mammospheres formed in Matrigel after treatment with DSF-Cu, evidenced by dispersion of cell clusters (FIG. 5A). Paralleling 2D culture conditions, SUM149 mammospheres remained intact following treatment with either agent alone.

Anchorage-independent growth (AIG) in soft agar is widely used as an in vitro model to assess cancer cell tumorigenicity and is considered a useful predictor of in vivo activity (Debeb et al., 2012). AIG (measured by colony number) was significantly inhibited by DSF-Cu in both SUM149 and rSUM149 cell lines (FIG. 5B). Representative images in FIG. 5C show an abundance of large colonies in untreated and single treatment samples, while only diffuse individual cells are seen in DSF-Cu-treated samples.

Since DSF is an inhibitor of the aldehyde dehydrogenase class of enzymes (Johansson, 1992), we wanted to determine whether DSF or DSF-Cu could inhibit the tumorigenic factor ALDH. SUM149 cells were treated for 24 h with a sub-lethal dose of DSF or DSF-Cu and analyzed for ALDH activity using the ALDEFLUOR assay. Data in FIG. 5D show that while neither DSF nor Cu alone affected the ALDH+ population, DSF-Cu significantly reduced the proportion of ALDH+ cells (FIG. 5D, $p<0.005$). These data are highly relevant as IBC tumors and cell lines, including SUM149, are often characterized by a high degree of ALDH activity, which has been linked with increased growth capacity in 3D culture and enhanced tumorigenicity in vivo (Charafe-Jauffret et al., 2010).

3.6 DSF-Cu Inhibits Growth of SUM149-Derived Tumors in an In Vivo Murine Model

To further investigate DSF as a potential therapeutic strategy for IBC, we utilized an in vivo tumor model to evaluate the anti-tumoral efficacy of systemically administered DSF and Cu. Mice were treated daily with vehicle control, DSF, or DSF-Cu, and tumor volume was monitored. DSF-Cu significantly inhibited growth of SUM149 tumors compared to vehicle control and DSF alone ($p=3.4E-06$, FIG. 6A). Mice treated with DSF-Cu reached an average tumor volume of 363 $mm^3$ over the study, while all vehicle-treated tumors exceeded 1500 $mm^3$, revealing ~84% inhibition of tumor growth (FIG. 6A). Tumor burden in the DSF treatment group was reduced at the time of dissection despite no reduction in tumor growth, however tumor burden was lowest in the DSF-Cu group (~75%; $p<0.0001$). Whole animal weights did not change significantly in any group during treatment (Suppl. Table 3). Data in FIG. 6B show reduced levels of NFκB p65 phosphorylation, eIF4G1 and SOD1 expression in DSF-Cu-treated tumor lysates, consistent with results from our in vitro studies (FIG. 2B, 3B). Tumors from mice treated with vehicle control and DSF showed little to no TUNEL staining (apoptotic marker) (FIG. 6C, left and middle panel), while tumor cells from DSF-Cu-treated mice showed significant TUNEL staining (FIG. 6C, right panel). Quantitation of the number of TUNEL positive cells is displayed in FIG. 6D.

Our own studies (FIG. 4), consistent with a previous report (Cen et al., 2004), indicated that DSF can increase uptake of Cu by cancer cells in culture. Because bioavailability and tissue distribution are important pharmacokinetic factors, we investigated whether administered Cu reached the tumor by comparing Cu concentrations between treated tumors. DSF-Cu treatment resulted in higher intratumoral Cu concentrations measured via ICP-HRMS, although the difference was not statistically significant potentially due to limited sample size (FIG. 6E). Together, these results indicate that DSF-Cu is an effective combination whose mechanisms including targeting of the oxidative stress response and the anti-apoptotic program work together to inhibit tumor growth in an in vivo setting. The schematic in FIG. 6F summarizes the multi-factorial mechanisms that contribute to DSF-Cu's anti-tumoral efficacy.

4. Discussion

Cancer cells are under persistent oxidative stress relative to normal cells, and redox status regulates many cancer cell characteristics such as activation of proto-oncogenes and transcription factors, genomic instability, and therapeutic outcome. To compensate for increased oxidative stress, cancer cells activate redox adaptive mechanisms which enhance their ability to detoxify ROS (Trachootham et al., 2009). To examine oxidative stress response in BC, we identified 521 differentially expressed genes in SUM149 cells (an established, well-studied model of IBC) with and without addition of the classical ROS inducer, $H_2O_2$. We applied this oxidative stress response (OSR) metagene to expression data from pretreatment IBC and non-IBC clinical samples and normal breast tissue. The data revealed the identified OSR metagene scores were significantly higher in IBC samples than in non-IBC samples or normal breast tissue. As the efficacy of many anti-cancer agents depends on a strong induction of ROS and oxidative stress-induced cell death, resistance to those therapies develops when cancer types with inherently high ROS levels like IBC evolve redox adaptive mechanisms that allow them to survive in an environment of increased oxidative stress. Thus, the IBC tumor cells with an inherently high OSR may represent a redox-adapted population that develops high rates of failure to ROS-inducing treatments like chemo- and radiotherapy. Therefore, introduction of a redox modulatory strategy has the potential to block the oxidative stress response, tip the balance toward ROS-mediated cell death, and enhance efficacy of traditional therapies in cancer cells (Trachootham et al., 2009). In the current study, DSF, an FDA-approved anti-alcoholism drug used for over 40 years with extensive pre-clinical, clinical, and safety data (Johansson, 1992), induced potent ROS accumulation and death in IBC cells when combined with exogenous Cu. Further, DSF-Cu equalized the response of cells with acquired therapeutic resistance (rSUM149 and rSUM190) to that of their more sensitive parental counterparts.

In addition to the fact that dithiocarbamates like DSF can bind Cu (Hogarth, 2012), we identified that DSF acts as a Cu ionophore, facilitating cellular Cu accumulation in a Ctr1-independent manner. Although use of Cu as an anti-cancer agent is considered attractive (Gupte and Mumper, 2009), intracellular transport of Cu is a major challenge due to stringent control by Cu transporters. One scenario for the mechanism of DSF-Cu complex formation is that lipophilic DSF penetrates into cancer cells to form the apoptosis-inducing $Cu(deDTC)_2$ complex with intracellular Cu. As many cancer cells, including breast, have higher levels of Cu than normal tissue (two- to three-fold increases) (Mulay et al., 1971; Rizk and Sky-Peck, 1984), the increase in Cu(deDTC)$_2$ after DSF enters may enable DSF to target cancer cells selectively (Chen et al., 2006). However, in the IBC cells tested here, DSF induced toxicity only at concentrations greater than 10 μM, a dose that is not readily achievable in human plasma where the accepted daily dosing of 250-500 mg yields a plasma concentration <2 μM (Faiman et al., 1984). DSF's potency was significantly enhanced by exogenous Cu, with $IC_{50}$s for DSF-Cu in the 200-300 nM range in SUM149 and rSUM149 (FIG. 3A). In the present study, the addition of DSF significantly enhanced cell-associated Cu concentrations (FIG. 4A), indicating that DSF plays a role in mediating Cu uptake rather than just binding intracellular Cu. Further, the fact that DSF-Cu is equally effective in rSUM149 cells, which express Ctr1 at significantly lower levels than SUM149 (FIG. 4B), indicates that a Ctr1-independent mechanism is behind DSF-Cu efficacy. The inability of Ctr1 knockdown to inhibit DSF-Cu-mediated cell death (FIG. 4C) confirms the Ctr1-independence of DSF-Cu and provides further evidence for DSF as a Cu ionophore. These results are consistent with a model in which DSF complexes with Cu in the extracellular space and transports it across the plasma membrane into the cell as part of the $Cu(deDTC)_2$ complex.

It has been shown that dysregulation of NF-κB (a pro-survival factor and redox sensor) and its target genes is a critical molecular determinant in IBC disease progression (Iwamoto et al., 2011; Nguyen et al., 2006; Van Laere et al., 2006). DSF-Cu inhibited NF-κB activation and decreased antioxidants levels in SUM149 and rSUM149 cells, leading to activation of a pro-apoptotic redox response (FIGS. 2B, C, and E). Another observation of significance is downregulation of XIAP by DSF-Cu (FIG. 3B). XIAP, the most potent anti-apoptotic protein, is considered a chemoresistance factor in many cancer types (Kashkar, 2010), and we have previously reported a strong correlation between XIAP overexpression and acquired resistance to trastuzumab (Aird et al., 2008), TRAIL (Allensworth et al., 2012), lapatinib (Aird et al., 2010), and other therapies (Williams et al., 2013) in IBC. Further, XIAP is a Cu homeostasis factor, and formation of a Cu-XIAP complex can inhibit XIAP's anti-apoptotic function (Mufti et al., 2007), identifying a potential mechanism by which DSF-Cu induces apoptosis. Inhibition of NF-κB, a positive transcriptional regulator of XIAP, may also play a role in XIAP's downregulation. Further, XIAP is translationally upregulated during cell stress, which may involve the translation initiation factor eIF4G1 (Silvera et al., 2009). As eIF4G1 overexpression is a critical factor in tumor emboli formation and the metastatic nature of IBC (Silvera et al., 2009), reduction in eIF4G1 levels by DSF-Cu in IBC cells (FIG. 3B) and tumors (FIG. 6D) would be expected to reduce tumor aggressiveness. DSF-Cu also inhibited ALDH1 activity, which is linked to cancer stem cells (CSCs) (Croker et al., 2009), enhanced tumorigenic and metastatic potential (Croker et al., 2009), and resistance to chemo- and targeted therapies (Januchowski et al., 2013). Additionally, CSCs exhibit low basal levels of ROS (Diehn et al., 2009), and some studies have shown that ALDH1A1 plays an important role in protection again oxidative stress in stem cells (Singh et al., 2013); thus, ALDH represents an important target for anti-tumor therapy, particularly in redox-adapted cells.

5. Conclusion

Together, these data reveal the role of DSF as a Cu ionophore and demonstrate anti-cancer efficacy of DSF-Cu in in vitro and in vivo models of IBC. The metagene analyses of pre-treatment samples supports translation of this FDA-approved drug into clinical trials for advanced breast cancers to enhance and prolong sensitivity to standard chemotherapy.

References for Example 1

Abramoff, M. D., Magalhaes, P. J., Ram, S. J., 2004. Image Processing with ImageJ. Biophotonics International 11, 36-42.

Aird, K. M., Allensworth, J. L., Batinic-Haberle, I., Lyerly, H. K., Dewhirst, M. W., Devi, G. R., 2012. ErbB1/2 tyrosine kinase inhibitor mediates oxidative stress-induced apoptosis in inflammatory breast cancer cells. Breast cancer research and treatment 132, 109-119.

Aird, K. M., Ding, X., Baras, A., Wei, J., Morse, M. A., Clay, T., Lyerly, H. K., Devi, G. R., 2008. Trastuzumab signaling in ErbB2-overexpressing inflammatory breast cancer correlates with X-linked inhibitor of apoptosis protein expression. Molecular cancer therapeutics 7, 38-47.

Aird, K. M., Ghanayem, R. B., Peplinski, S., Lyerly, H. K., Devi, G. R., 2010. X-linked inhibitor of apoptosis protein inhibits apoptosis in inflammatory breast cancer cells with acquired resistance to an ErbB1/2 tyrosine kinase inhibitor. Molecular cancer therapeutics 9, 1432-1442.

Allensworth, J. L., Aird, K. M., Aldrich, A. J., Batinic-Haberle, I., Devi, G. R., 2012. XIAP inhibition and generation of reactive oxygen species enhances TRAIL sensitivity in inflammatory breast cancer cells. Molecular cancer therapeutics 11, 1518-1527.

Allensworth, J. L., Sauer, S. J., Lyerly, H. K., Morse, M. A., Devi, G. R., 2013. Smac mimetic Birinapant induces apoptosis and enhances TRAIL potency in inflammatory breast cancer cells in an IAP-dependent and TNF-alpha-independent mechanism. Breast cancer research and treatment 137, 359-371.

Bellezza, I., Mierla, A. L., Minelli, A., 2010. Nrf2 and NF-kappaB and Their Concerted Modulation in Cancer Pathogenesis and Progression. Cancers 2, 483-497.

Bertucci, F., Ueno, N. T., Finetti, P., Vermeulen, P., Lucci, A., Robertson, F. M., Marsan, M., Iwamoto, T., Krishnamurthy, S., Masuda, H., Van Dam, P., Woodward, W. A., Cristofanilli, M., Reuben, J. M., Dirix, L., Viens, P., Symmans, W. F., Birnbaum, D., Van Laere, S. J., 2013. Gene expression profiles of inflammatory breast cancer: correlation with response to neoadjuvant chemotherapy and metastasis-free survival. Annals of oncology: official journal of the European Society for Medical Oncology/ESMO.

Brewer, G. J., 2009. The use of copper-lowering therapy with tetrathiomolybdate in medicine. Expert opinion on investigational drugs 18, 89-97.

Brown, N. S., Bicknell, R., 2001. Hypoxia and oxidative stress in breast cancer. Oxidative stress: its effects on the growth, metastatic potential and response to therapy of breast cancer. Breast cancer research: BCR 3, 323-327.

Cen, D., Brayton, D., Shahandeh, B., Meyskens, F. L., Jr., Farmer, P. J., 2004. Disulfiram facilitates intracellular Cu uptake and induces apoptosis in human melanoma cells. Journal of medicinal chemistry 47, 6914-6920.

Charafe-Jauffret, E., Ginestier, C., Iovino, F., Tarpin, C., Diebel, M., Esterni, B., Houvenaeghel, G., Extra, J. M., Bertucci, F., Jacquemier, J., Xerri, L., Dontu, G., Stassi, G., Xiao, Y., Barsky, S. H., Birnbaum, D., Viens, P., Wicha, M. S., 2010. Aldehyde dehydrogenase 1-positive cancer stem cells mediate metastasis and poor clinical outcome in inflammatory breast cancer. Clinical cancer research: an official journal of the American Association for Cancer Research 16, 45-55.

Chen, D., Cui, Q. C., Yang, H., Dou, Q. P., 2006. Disulfiram, a clinically used anti-alcoholism drug and copper-binding agent, induces apoptotic cell death in breast cancer cultures and xenografts via inhibition of the proteasome activity. Cancer research 66, 10425-10433.

Croker, A. K., Goodale, D., Chu, J., Postenka, C., Hedley, B. D., Hess, D. A., Allan, A. L., 2009. High aldehyde dehydrogenase and expression of cancer stem cell markers selects for breast cancer cells with enhanced malignant and metastatic ability. Journal of cellular and molecular medicine 13, 2236-2252.

Dawood, S., Cristofanilli, M., 2011. Inflammatory breast cancer: what progress have we made? Oncology (Williston Park, N.Y.) 25, 264-270, 273.

Debeb, B. G., Cohen, E. N., Boley, K., Freiter, E. M., Li, L., Robertson, F. M., Reuben, J. M., Cristofanilli, M., Buchholz, T. A., Woodward, W. A., 2012. Pre-clinical studies of Notch signaling inhibitor RO4929097 in inflammatory breast cancer cells. Breast cancer research and treatment 134, 495-510.

Diehn, M., Cho, R. W., Lobo, N. A., Kalisky, T., Dorie, M. J., Kulp, A. N., Qian, D., Lam, J. S., Ailles, L. E., Wong, M., Joshua, B., Kaplan, M. J., Wapnir, I., Dirbas, F. M., Somlo, G., Garberoglio, C., Paz, B., Shen, J., Lau, S. K., Quake, S. R., Brown, J. M., Weissman, I L., Clarke, M. F., 2009. Association of reactive oxygen species levels and radioresistance in cancer stem cells. Nature 458, 780-783.

Evans, M. K., Tovmasyan, A., Batinic-Haberle, I., Devi, G. R., 2013. Mn porphyrin in combination with ascorbate acts as a pro-oxidant and mediates caspase-independent cancer cell death. Free radical biology & medicine 68c, 302-314.

Faiman, M. D., Jensen, J. C., Lacoursiere, R. B., 1984. Elimination kinetics of disulfiram in alcoholics after single and repeated doses. Clinical pharmacology and therapeutics 36, 520-526.

Fraga, C. G., 2005. Relevance, essentiality and toxicity of trace elements in human health. Molecular aspects of medicine 26, 235-244.

Gorrini, C., Harris, I S., Mak, T. W., 2013. Modulation of oxidative stress as an anticancer strategy. Nature reviews. Drug discovery 12, 931-947.

Gupte, A., Mumper, R. J., 2009. Elevated copper and oxidative stress in cancer cells as a target for cancer treatment. Cancer treatment reviews 35, 32-46.

Hogarth, G., 2012. Metal-dithiocarbamate complexes: chemistry and biological activity. Mini reviews in medicinal chemistry 12, 1202-1215.

Iwamoto, T., Bianchini, G., Qi, Y., Cristofanilli, M., Lucci, A., Woodward, W. A., Reuben, J. M., Matsuoka, J., Gong, Y., Krishnamurthy, S., Valero, V., Hortobagyi, G. N., Robertson, F., Symmans, W. F., Pusztai, L., Ueno, N. T., 2011. Different gene expressions are associated with the different molecular subtypes of inflammatory breast cancer. Breast cancer research and treatment 125, 785-795.

Januchowski, R., Wojtowicz, K., Zabel, M., 2013. The role of aldehyde dehydrogenase (ALDH) in cancer drug resistance. Biomedicine & pharmacotherapy=Biomedecine & pharmacotherapie 67, 669-680.

Johansson, B., 1992. A review of the pharmacokinetics and pharmacodynamics of disulfiram and its metabolites. Acta psychiatrica Scandinavica. Supplementum 369, 15-26.

Kashkar, H., 2010. X-linked inhibitor of apoptosis: a chemoresistance factor or a hollow promise. Clinical cancer research : an official journal of the American Association for Cancer Research 16, 4496-4502.

Klopp, A. H., Lacerda, L., Gupta, A., Debeb, B. G., Solley, T., Li, L., Spaeth, E., Xu, W., Zhang, X., Lewis, M. T., Reuben, J. M., Krishnamurthy, S., Ferrari, M., Gaspar, R., Buchholz, T. A., Cristofanilli, M., Marini, F., Andreeff, M., Woodward, W. A., 2010. Mesenchymal stem cells promote mammosphere formation and decrease E-cadherin in normal and malignant breast cells. PloS one 5, e12180.

Manda, G., Nechifor, M. T., Neagu, T.-M., 2009. Reactive Oxygen Species, Cancer and Anti-Cancer Therapies. Current Chemical Biology 3, 22-46.

Masuda, H., Brewer, T. M., Liu, D. D., Iwamoto, T., Shen, Y., Hsu, L., Willey, J. S., Gonzalez-Angulo, A. M., Chavez-MacGregor, M., Fouad, T. M., Woodward, W. A., Reuben, J. M., Valero, V., Alvarez, R. H., Hortobagyi, G. N., Ueno, N. T., 2014. Long-term treatment efficacy in primary inflammatory breast cancer by hormonal receptor- and HER2-defined subtypes. Annals of oncology: official journal of the European Society for Medical Oncology/ESMO 25, 384-391.

Mufti, A. R., Burstein, E., Duckett, C S., 2007. XIAP: cell death regulation meets copper homeostasis. Archives of biochemistry and biophysics 463, 168-174.

Mulay, I L., Roy, R., Knox, B. E., Suhr, N. H., Delaney, W. E., 1971. Trace-metal analysis of cancerous and noncancerous human tissues. Journal of the National Cancer Institute 47, 1-13.

Nguyen, D. M., Sam, K., Tsimelzon, A., Li, X., Wong, H., Mohsin, S., Clark, G. M., Hilsenbeck, S. G., Elledge, R. M., Allred, D. C., O'Connell, P., Chang, J. C., 2006. Molecular heterogeneity of inflammatory breast cancer: a hyperproliferative phenotype. Clinical cancer research : an official journal of the American Association for Cancer Research 12, 5047-5054.

Nose, Y., Kim, B. E., Thiele, D. J., 2006. Ctr1 drives intestinal copper absorption and is essential for growth, iron metabolism, and neonatal cardiac function. Cell metabolism 4, 235-244.

Pena, M. M., Koch, K. A., Thiele, D. J., 1998. Dynamic regulation of copper uptake and detoxification genes in *Saccharomyces cerevisiae*. Molecular and cellular biology 18, 2514-2523.

Reeder, N. L., Kaplan, J., Xu, J., Youngquist, R. S., Wallace, J., Hu, P., Juhlin, K. D., Schwartz, J. R., Grant, R. A., Fieno, A., Nemeth, S., Reichling, T., Tiesman, J. P., Mills, T., Steinke, M., Wang, S. L., Saunders, C. W., 2011. Zinc pyrithione inhibits yeast growth through copper influx and inactivation of iron-sulfur proteins. Antimicrobial agents and chemotherapy 55, 5753-5760.

Rizk, S. L., Sky-Peck, H. H., 1984. Comparison between concentrations of trace elements in normal and neoplastic human breast tissue. Cancer research 44, 5390-5394.

Robertson, F. M., Bondy, M., Yang, W., Yamauchi, H., Wiggins, S., Kamrudin, S., Krishnamurthy, S., Le-Petross, H., Bidaut, L., Player, A. N., Barsky, S. H., Woodward, W. A., Buchholz, T., Lucci, A., Ueno, N. T., Cristofanilli, M., 2010. Inflammatory breast cancer: the disease, the biology, the treatment. CA: a cancer journal for clinicians 60, 351-375.

Robinson, J. S., Klionsky, D. J., Banta, L. M., Emr, S. D., 1988. Protein sorting in *Saccharomyces cerevisiae*: isolation of mutants defective in the delivery and processing of multiple vacuolar hydrolases. Molecular and cellular biology 8, 4936-4948.

Rueth, N. M., Lin, H. Y., Bedrosian, I., Shaitelman, S. F., Ueno, N. T., Shen, Y., Babiera, G., 2014. Underuse of trimodality treatment affects survival for patients with inflammatory breast cancer: an analysis of treatment and survival trends from the national cancer database. Journal of clinical oncology: official journal of the American Society of Clinical Oncology 32, 2018-2024.

Saigal, K., Hurley, J., Takita, C., Reis, I. M., Zhao, W., Rodgers, S E., Wright, J. L., 2013. Risk factors for locoregional failure in patients with inflammatory breast cancer treated with trimodality therapy. Clinical breast cancer 13, 335-343.

Silvera, D., Arju, R., Darvishian, F., Levine, P. H., Zolfaghari, L., Goldberg, J., Hochman, T., Formenti, S. C., Schneider, R. J., 2009. Essential role for eIF4GI overexpression in the pathogenesis of inflammatory breast cancer. Nature cell biology 11, 903-908.

Singh, S., Brocker, C., Koppaka, V., Chen, Y., Jackson, B. C., Matsumoto, A., Thompson, D. C., Vasiliou, V., 2013. Aldehyde dehydrogenases in cellular responses to oxidative/electrophilic stress. Free radical biology & medicine 56, 89-101.

Taminau, J., Meganck, S., Lazar, C., Steenhoff, D., Coletta, A., Molter, C., Duque, R., de Schaetzen, V., Weiss Solis, D. Y., Bersini, H., Nowe, A., 2012. Unlocking the potential of publicly available microarray data using inSilicoDb and inSilicoMerging R/Bioconductor packages. BMC bioinformatics 13, 335.

Trachootham, D., Alexandre, J., Huang, P., 2009. Targeting cancer cells by ROS-mediated mechanisms: a radical therapeutic approach? Nature reviews. Drug discovery 8, 579-591.

Van Laere, S. J., Ueno, N. T., Finetti, P., Vermeulen, P., Lucci, A., Robertson, F. M., Marsan, M., Iwamoto, T., Krishnamurthy, S., Masuda, H., van Dam, P., Woodward, W. A., Viens, P., Cristofanilli, M., Birnbaum, D., Dirix, L., Reuben, J. M., Bertucci, F., 2013. Uncovering the molecular secrets of inflammatory breast cancer biology: an integrated analysis of three distinct affymetrix gene expression datasets. Clinical cancer research: an official journal of the American Association for Cancer Research 19, 4685-4696.

Van Laere, S. J., Van der Auwera, I., Van den Eynden, G. G., Elst, H. J., Weyler, J., Harris, A. L., van Dam, P., Van Marck, E. A., Vermeulen, P. B., Dirix, L. Y., 2006. Nuclear factor-kappaB signature of inflammatory breast cancer by cDNA microarray validated by quantitative real-time reverse transcription-PCR, immunohistochemistry, and nuclear factor-kappaB DNA-binding. Clinical cancer research : an official journal of the American Association for Cancer Research 12, 3249-3256.

Wang, W., McLeod, H. L., Cassidy, J., 2003. Disulfiram-mediated inhibition of NF-kappaB activity enhances cytotoxicity of 5-fluorouracil in human colorectal cancer cell lines. International journal of cancer. Journal international du cancer 104, 504-511.

Williams, K. P., Allensworth, J. L., Ingram, S. M., Smith, G. R., Aldrich, A. J., Sexton, J. Z., Devi, G. R., 2013. Quantitative high-throughput efficacy profiling of approved oncology drugs in inflammatory breast cancer models of acquired drug resistance and re-sensitization. Cancer letters 337, 77-89.

Yip, N. C., Fombon, I S., Liu, P., Brown, S., Kannappan, V., Armesilla, A. L., Xu, B., Cassidy, J., Darling, J. L., Wang, W., 2011. Disulfiram modulated ROS-MAPK and NFkappaB pathways and targeted breast cancer cells with cancer stem cell-like properties. British journal of cancer 104, 1564-1574.

Example 2. Targeting Inflammatory Breast Cancer Tumor Emboli: A Quantitative High Content Analysis This Example demonstrates the DSF-Cu inhibits 3D tumor spheroids from forming in SUM149 and isotype matched multidrug resistant rSUM149 cells.

Figure 12:
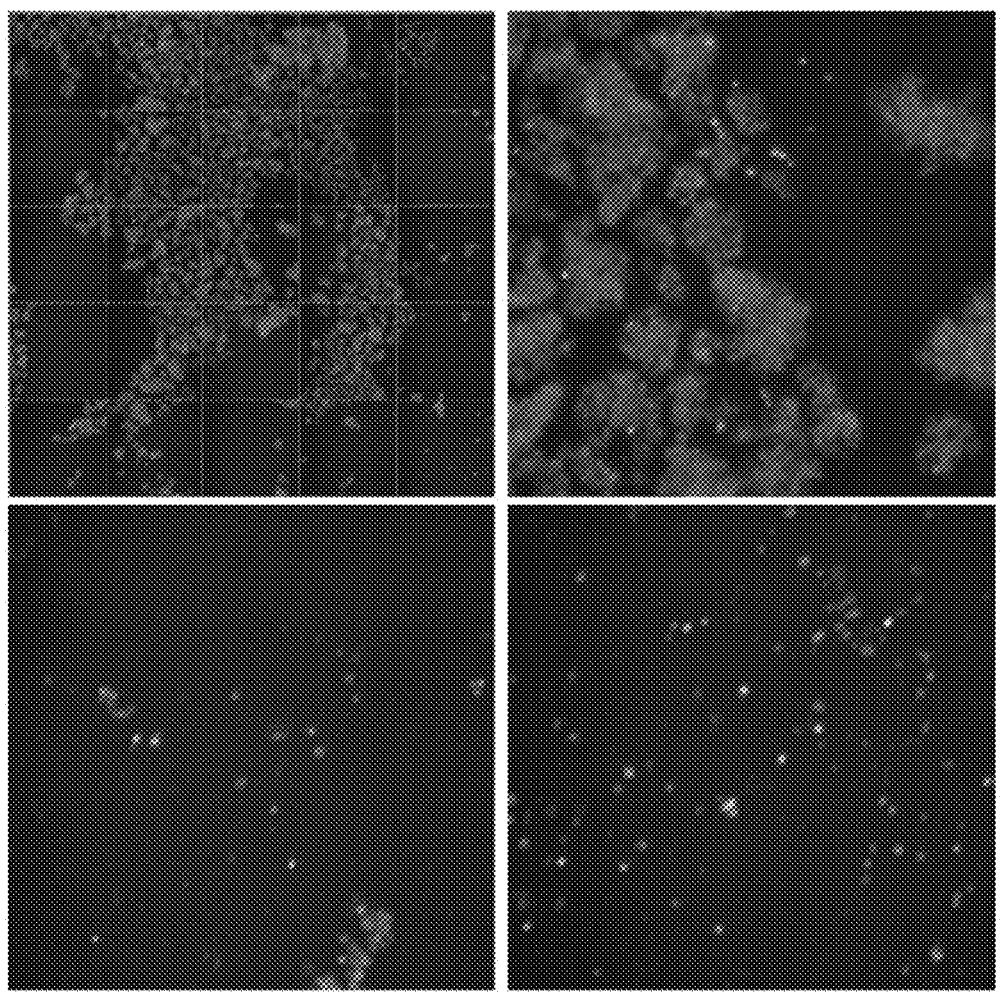
FIG. 12 shows DSF-Cu inhibits 3D tumor spheroids derived from SUM149 and an isotype matched multidrug resistant rSUM149 cells.

FIG. 12 shows that SUM149 cells were treated with DSF-CU at 100 nM or 300 nM in the in vitro Sum149 tumor spheroid model.

Using lymphatic simulating tumor emboli model (Lehman, 2013), SUM149 cells were treated with DSF, Cu and DSF-Cu at the time of seeding. Spheroids were manually counted using phase contrast microscopy on day 4. Results are shown in the bar graph and represented microscopy figures are shown.

Figure 14:
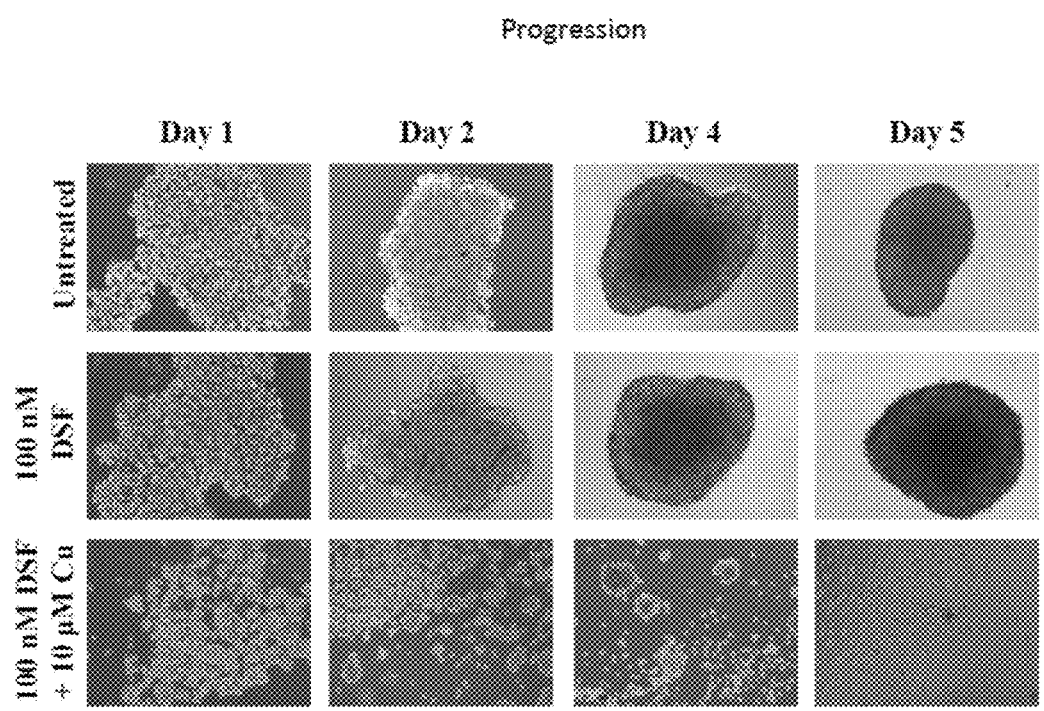
FIG. 14 shows the progression of in vitro tumor emboli formation for 5 days after treatment with DSF alone or with Cu.
Figure 15:
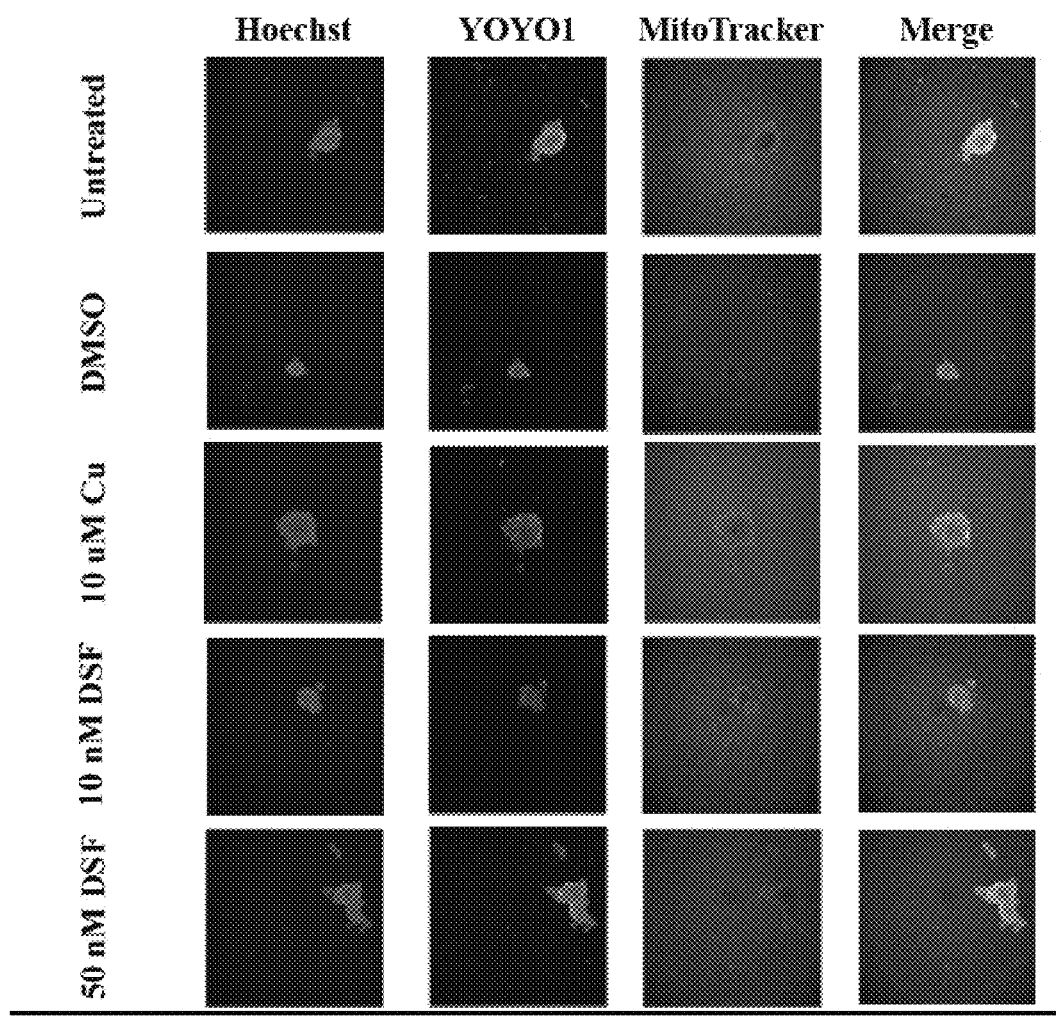
FIG. 15 shows in vitro staining of tumor emboli after treatments with DMSO, Cu, or two concentrations of DSF.
Figure 16:
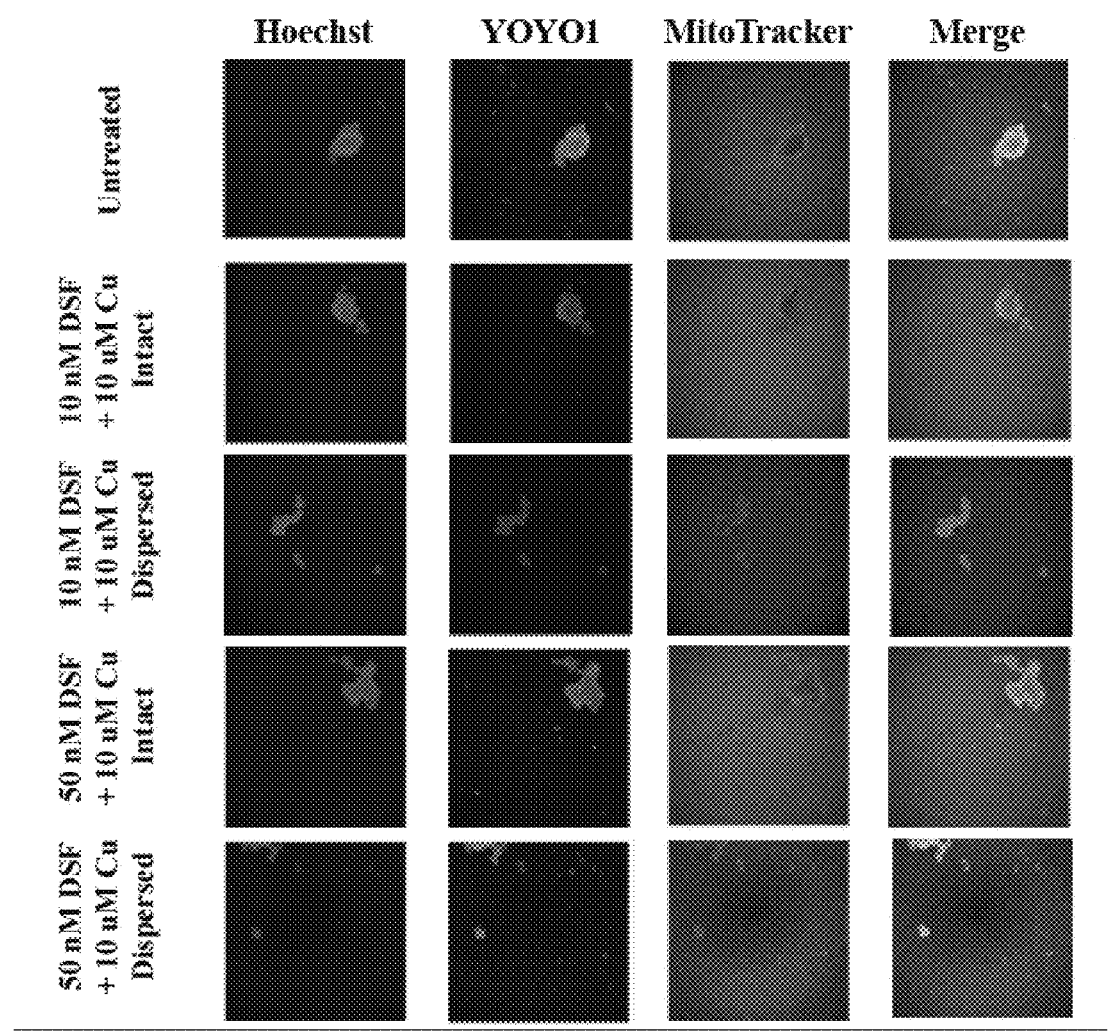
FIG. 16 shows in vitro staining of tumor emboli after treatments with DSF and Cu.

The progression of tumor emboli formation using SUM149 cells was followed and the effects of DSF-Cu studied over time. Representative microscopy images are depicted in FIG. 14 over time. FIGS. 15 and 16 show staining of the cells. This Example demonstrates that DSF-Cu leads to the reduction or inhibition of tumor emboli formation.

Figure 17:
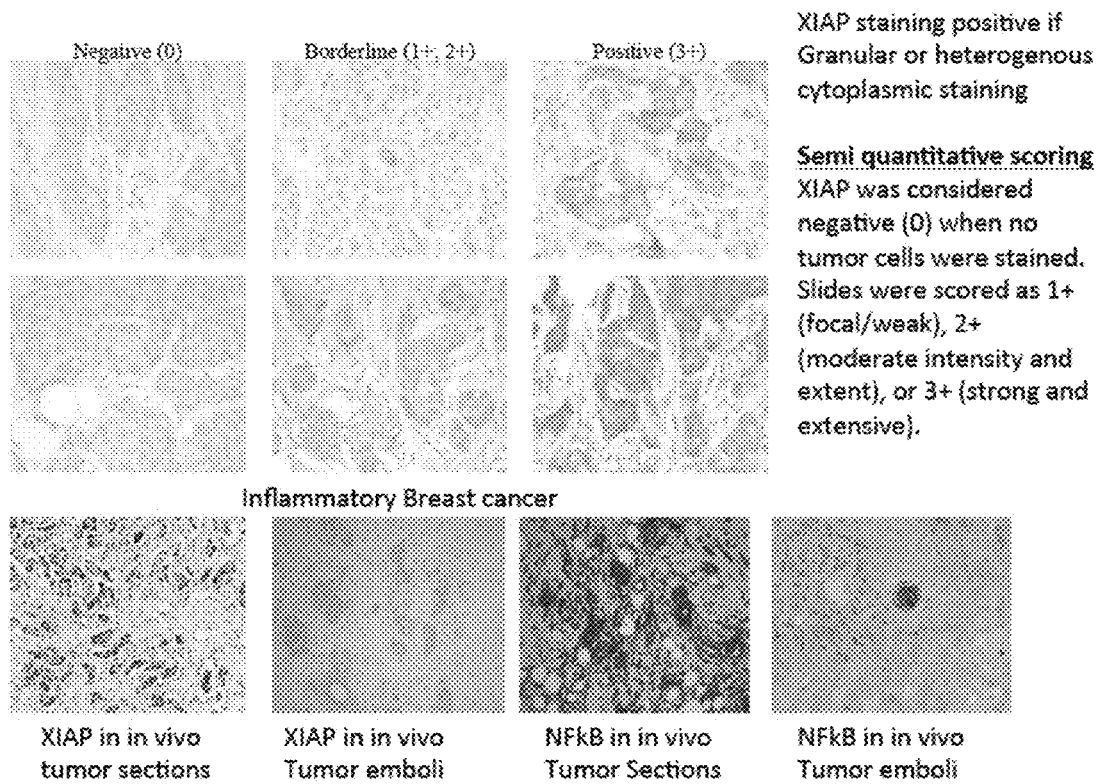
FIG. 17 shows XIAP staining in in vivo tumor sections or in vivo tumor emboli.

Further in vivo tumor sections were stained for XIAP, as depicted in FIG. 17. XIAP was considered negative (o) when no tumor cells were stained. Slides were scored as 1+ (focal/weak), 2+ (moderate intensity and extent) or 3+ (strong and extensive), based on cytoplasmic staining. Inflammatory breast cancer samples were also stained.

Example 3. Role of Oxidative Stress in Breast Cancer

This Example provides a review of the accepted concepts, recent findings and limitations in the understanding of the cross-talk between antioxidant capacity, redox-sensitive transcription factors and cell survival/death signaling in oxidative stress response and redox adaptation in breast cancer. Addressing these matters and identifying pathway dysregulation is required for a rational basis to improve the design of redox-related therapeutics and clinical trials in breast cancer.

Redox Homeostasis: ROS Production and Elimination

Reactive species, also termed oxidants, are byproducts of key aerobic cellular processes of respiration, metabolism and the mitochondrial electron transport chain (mETC)[1, 2] and are removed continuously by an array of antioxidant mechanisms. These species include reactive oxygen species (ROS) and reactive nitrogen species (RNS). ROS are mainly comprised of neutral molecules ($H_2O_2$), radicals (hydroxyl radicals), and ions (superoxide)[3]. On the other hand, nitric oxide, the main form of RNS in the cell, is produced by a family of enzymes (nitric oxide synthases, NOSs) that include iNOS (inducible), eNOS (endothelial) and nNOS (neuronal)[4]. ROS can also be produced at somewhat low levels in response to the activation of certain signaling pathways, such as the epidermal growth factor receptor (EGFR) pathway[5]. Activation of these pathways has been shown to be important for proliferation, as well as the oncogenic and metastatic potential of cancer cells. Extracellular sources of ROS include tobacco, smoke, drugs, xenobiotics, radiation and high levels of heat, most of which either activate a stress response or directly damage cellular components leading to ROS production[6].

Cells have natural defense systems against ROS that consists of antioxidant enzymes and scavengers. Some of these antioxidants are produced inside cells and the human body, mostly falling into the enzymatic category, as they are predominantly protein in nature. These proteins include the superoxide dismutase (SOD) enzymes (which have differential subcellular localization and dismute superoxide to $H_2O_2$), glutathione peroxidase (GPx) and catalase (both of which clear peroxide), thioredoxins (Trxs) (reduce oxidized proteins), and glutathione synthetase (GSS) (synthesizes glutathione [GSH], an important antioxidant), among others[1, 7]. Antioxidant scavengers are mostly obtained from nutritional sources and include ascorbic acid (vitamin A), tocopherol (vitamin E), polyphenols, carotenoids, and uric acid[8].

Therefore, a fine balance exists between the levels of ROS and antioxidants within the cell. Oxidative stress occurs when the level of ROS exceeds the cellular antioxidant capacity either due to increased ROS production and/or impairment of the antioxidant capacity of the cells[11]. This stress promotes damage to key cellular structures including DNA, proteins and lipids, which play a pivotal role in the development of multiple types of cancer[9]. Expression of oncogenes (e.g. Ras, myc, telomerase) and loss of tumor suppressor genes (p53, p21, PTEN) can also increase ROS, leading to senescence or escape from apoptosis[10-12]. Oxidative stress can cause arrest or induction of transcription, activation of signaling pathways and genomic instability, which are all hallmarks of cancer (including breast cancer) and are key factors that modulate cancer cell proliferation, evasion of apoptosis, angiogenesis and metastasis[9].

Oxidative Stress as a Driver of Breast Cancer Development and Progression

ROS as Second Messengers in Breast Cancer

Figure 18:
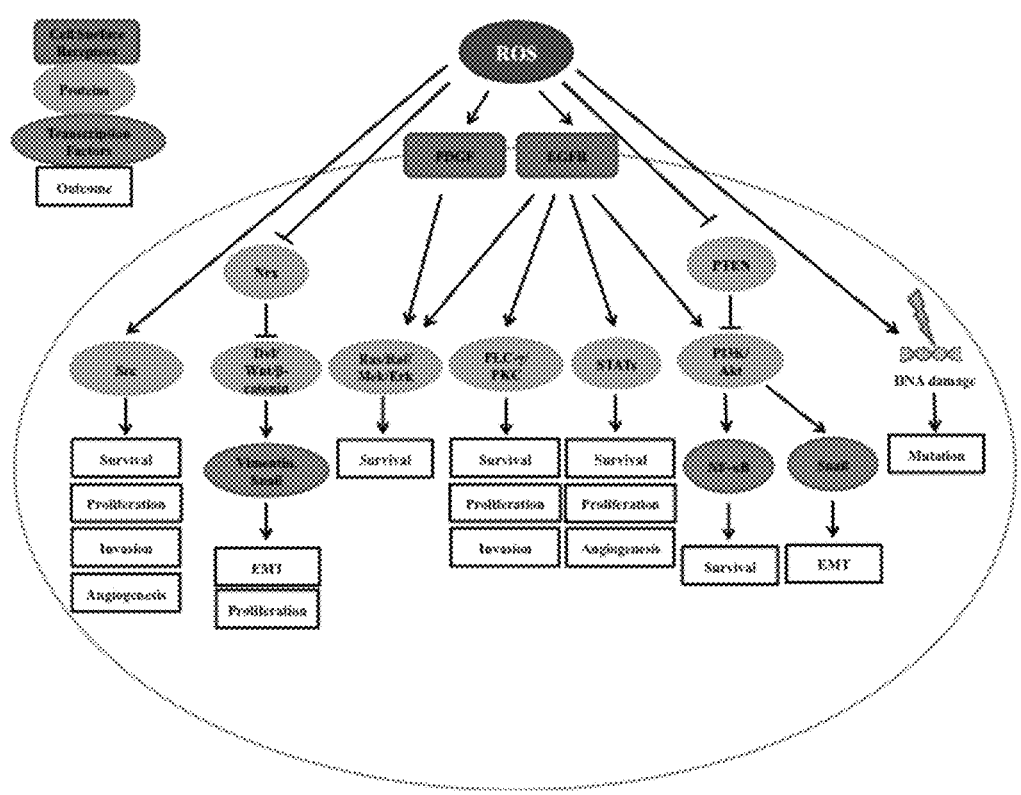
FIG. 18 is a schematic depiction of the signaling effects of ROS in breast cancer. ROS promotes the development of breast cancer through activation of cell signaling pathways that promote survival, proliferation, invasion, angiogenesis, and EMT including Src, Wnt/β-catenin, Ras/Raf/Mek/ERK, EGFR and PI3K/Akt; additionally, DNA damage promotes the acquisition of mutations [46].

The role of oxidative stress in the etiology of breast cancer is supported by multiple lines of evidence[13]. Although ROS are generally thought of as damaging to cells due to their ability to induce oxidative stress at high concentrations, low levels of ROS are actually essential to normal cell function. This is in part due to the fact that ROS can act as second messengers in signaling cascades that are vital for cellular responses to external stimuli. In order to be characterized as a second messenger, the molecule must: 1) exhibit concentration control at the level of synthesis and removal; 2) exhibit effector molecule specificity, and 3) take part in a reversible signaling interaction[14]. Due to very high reactivity that preclude substrate specificity, superoxides, hydroxyl radicals and singlet oxygen are not considered to be second messengers of signaling[15]. However, the enzymatic production and degradation of $H_2O_2$, along with its preferential reactivity with protein thiols, which are reversibly oxidized, allows for its characterization as a second messenger[15]. It is known that levels of ROS are often upregulated in cancer cells, and their role in promoting certain signaling cascades is likely one reason that this adaptation is advantageous[16]. FIG. 18 summarizes the well-characterized signaling effects of ROS in breast cancer and highlights the role of ROS in regulating growth factor receptor signaling, epithelial-mesenchymal transition and stem cell-like phenotype in breast cancer.

Mutation and Inactivation of Antioxidants

As mentioned earlier there exists a balance between ROS and cellular antioxidants and alterations in the genes that encode certain antioxidants are associated with increased proliferation and progression of cancer[16]. These alterations in antioxidant genes can be either gain of function or loss of function depending on the cell type, gene and function of that gene in the context of cancer. In human breast cancer patients, there is a multitude of contrasting data, however, it has been posited that during progression of cancer, low levels of SOD2 lead to increased ROS and a significant accumulation of mutations, while in late stages SOD2 is increased to combat ROS and promote carcinogenesis[17]. Robinson et al. reported an inverse correlation between GPx levels and cancer progression[18]. A loss of heterozygosity (LOH) on chromosome 3p, where the GPx gene is located, has been frequently found in breast cancer[19]. It was previously reported that GPx expression inversely correlates with estrogen receptor status in breast cancer cell lines; however, a follow-up study using additional cell lines weakened this proposed correlation, and ER status is therefore not considered a good surrogate marker for GPx expression[20].

Tumor Hypoxia, HIF-1 and Oxidative Stress in Breast Cancer

Due to immature vascularization, areas of solid breast tumors often have inadequate blood supply. The level of tumor oxygenation in breast tumors is typically half that of normal tissues, with 30-40% of breast cancer tissue having a quarter of the amount of oxygenation as normal tissue[21]. Further, hypoxia can induce a quiescent state in tumor cells, which makes them less sensitive to chemotherapy designed to target rapidly dividing cells[21]. One of the most important mediators of the cellular hypoxic response is the transcription factor hypoxia inducible factor 1 (HIF-1). HIF-1 expression has been correlated with aggressive breast cancer and poor response to treatment[22]. Through changes in HIF-1 levels, hypoxic gene activation can occur through HIF-1 binding to hypoxia response elements (HREs)[21]. This upregulation of HIF-1 has been shown to increase breast cancer cell proliferation and p53 accumulation[23] and correlate with an increase in oxidative stress and production of vascular endothelial growth factor (VEGF) through the HRE, inducing production of blood vessel growth within the tumor and heightening the risk for metastasis[24]. Like VEGF, increased expression of another angiogenesis protein, erythropoietin, in breast cancer is HIF-1 dependent[25]. Additionally, the breast cancer-related oncogene HER2 has been shown to promote metastasis during hypoxia by increasing resistance to anoikis through a HIF-1-mediated mechanism[26].

Further, regulation of tumor metabolism in hypoxic cancer cells is mediated predominantly by HIF-1, wherein glucose transporter 1 (GLUT1), a protein that facilitates cellular glucose uptake, is increased in a HIF-1-dependent manner in breast cancer, increasing the dependence of the cell on glycolysis for energy[27]. Expression of mRNA levels of lactate dehydrogenase-A (LDH-A), involved in the glycolytic pathway and under hypoxic control through HIF-1, was reported to be markedly increased in breast cancer, along with a modest increase in activity[28]. HIF-1 has also been shown to increase levels of mRNA for CA9 (carbonic anhydrase IX), which is involved in proliferation and the neutralization of hypoxia-induced pH increases through increased glycolysis, NDRG1 (N-myc downstream-regulated 1), a stress-related gene involved with differentiation and IGFBP5 (insulin-like growth factor-binding protein 5), in breast cancers Inflammation and Oxidative Stress in Breast Cancer The presence of persistent free radicals during oxidative stress leads to induction of a chronic inflammatory response and evidence of this inflammation in breast tissue has been found through the increase in levels of tumor necrosis factor α (TNFα) due to infiltrating macrophages, dysregulated interleukin-6 (IL-6) production and upregulation of inflammatory enzymes such as cyclo-oxygenase 2 (COX2)[30]. These features lead to poor prognosis and drug response, as well as increased metastasis.

Increased COX2 production in breast cancer leads to higher production of prostaglandin 2 (PGE2). This stimulation of PGE2 production can then also lead to downstream signaling through MAPK, Src and Akt pathways, as well as VEGF and HIF-1α[31]. Particularly interesting is the effect of PGE2 on HIF1α, as the hypoxic environment of the tumor can give rise to inflammation and inflammation can affect HIF1α, thereby providing a potential link for cross-talk between hypoxia and inflammation in the tumor. PGE2-induced activation of these pathways results in the progression of breast cancer[32]. Further evidence of COX2's role in breast cancer is the finding that non-steroidal anti-inflammatory drugs (NSAIDs), which inhibit COX2, can reduce the risk of breast cancer[33]. Despite the diverse mechanisms of action of these inflammatory molecules in breast cancer, one potential point of convergence is that all of these pathways can modulate the production of aromatase[34]. Aromatase is vital in the production of estrogens, a critical factor in etiology and progression of breast cancer.

Estrogens and Oxidative Stress in Breast Cancer

Figure 19:
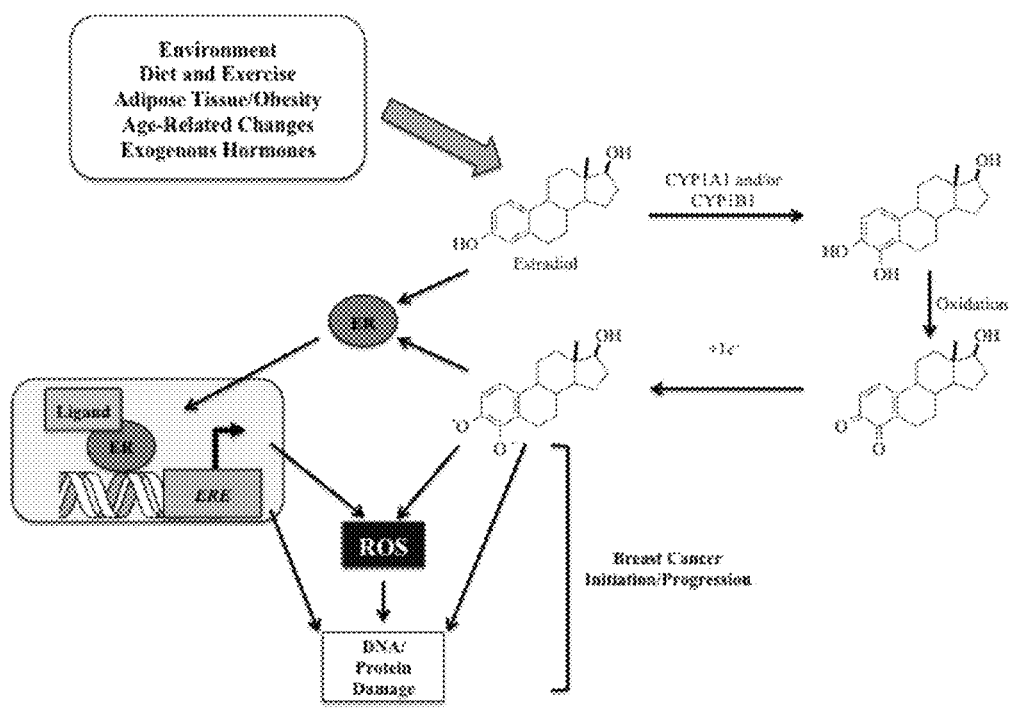
FIG. 19 depicts estrogens and estrogenic quinine-metabolites and a schematic of their effect on ROS. A variety of factors can impact the levels of estrogens in women. Estrogens can then go on to bind estrogen receptor to promote expression of genes with estrogen response elements, which can induce increased levels of ROS and subsequently DNA damage and carcinogenesis. Further, estrogens can form radical species through cytochrome p450 metabolism that can either bind estrogen receptor or induce DNA damage directly.

For over 100 years, a link between breast cancer and estrogen has been acknowledged, with current data strongly supporting this idea[35]. Estrogens and estrogenic quinone-metabolites as shown in FIG. 19, can act as ROS themselves and alkylate or damage DNA and proteins or bind to estrogen receptor (ER) and activate EREs, which in turn can increase levels of ROS. This is supported by the observation that estrogen-responsive cells like MCF-7 show increased mitochondrial membrane potential, increased ROS production and resultant compensatory changes in antioxidants[36]. Further, the higher the ERα/ERβ ratio in breast cancer cells, the higher the levels of ROS generated by estrogen[37].

Lifestyle, diet and environment influence oxidative stress levels and are linked to breast cancer initiation and disease progression. Of particular interest is the correlation between obesity and increased breast cancer risk in postmenopausal women. One potential cause of this risk factor is attributed to higher circulating estrogens caused by increased levels of adipose tissue, which can then drive the growth of ER-dependent tumors in postmenopausal women[38]. Further, aromatase expression was found to be higher in obese women with breast cancer and this correlated with markers of inflammation, such as COX-2 and PGE2[38]. Thus, a link between oxidative stress, obesity and breast cancer can be drawn, with estrogen as the point of convergence between these complex processes as shown in FIG. 19.

Age-Related Changes and Oxidative Stress in Breast Cancer

Telomeres are chromosomal end-caps that are shortened throughout the cellular aging process, and when telomeres shorten enough, cellular senescence occurs. Indeed, aging is associated with increased oxidative stress[39] and higher levels of oxidative stress have been observed to increase the rate of telomere shortening[40]. While telomerase may slow the effects of cellular aging, uncontrolled telomerase activity allows cells to replicate indefinitely, leading to the survival of cells with potentially carcinogenic mutations[41] and a mechanism by which cancer cells survive. This is also supported by a recent finding wherein increased ROS was identified to induce transport of the telomerase reverse transcriptase protein (TERT) from the nucleus to the mitochondria which then prevents nuclear DNA damage and cell death, a mechanism of cancer cell survival and resistance[42]. Together, these data reveal an interesting interplay between telomerase, natural aging-related oxidative stress in cells and implications in cancer therapy as a potential factor in age-related differences in therapeutic outcomes in breast cancer[43].

It has also been seen that increased age correlates with an increase in the number of mitochondrial DNA (mtDNA) mutations, which leads to age-related mitochondrial dysfunction due to increased oxidative stress in older individuals[44]. It has been observed that depletion of mtDNA-encoded genes can cause carcinogenesis in breast epithelial cells, mtDNA site mutations are associated with increase breast cancer risk and there is a higher frequency of mtDNA mutations observed in breast cancer tissue[44]. Interestingly, levels of oxidative stress have not been found to increase as a result of increased mtDNA mutations in vivo, indicating that oxidative stress may not mediate the carcinogenesis found with mtDNA mutations[45]. However, the higher frequency of mtDNA mutations as a result of aging may be one reason for a greater than eight-fold likelihood of being diagnosed with cancer at age 70 than age 30[38].

Epigenetics and Oxidative Stress in Breast Cancer

Figure 20:
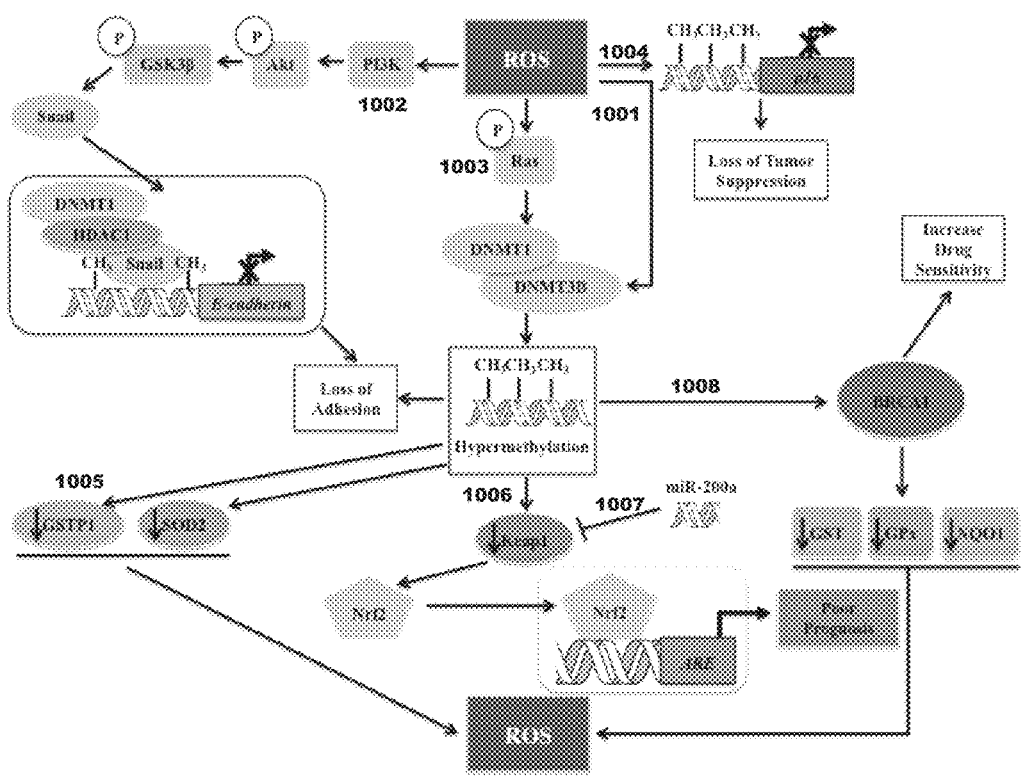
FIG. 20 is a schematic depiction of effects on ROS on DNA methylation within a cell. ROS can directly induce epigenetic changes through an increase in DNA methyltransferase 3b (dnmt3b) levels (see reference 1001). Activation of the PI3K/Akt pathway by ROS can lead to increased levels of Snail, inducing DNA methylation of the E-cadherin promoter, decreasing E-cadherin levels and leading to tumorigenic loss of cellular adhesion (see reference 1002). Activation of the Ras pathway by ROS leads to increased dnmt expression causing a global increase in DNA methylation (see reference 1003). ROS can lead to inactivation of the tumor suppressor gene p16, promoting tumorigenesis (see reference 1004). Hypermethylation of the promoters of antioxidants glutathione-S-transferase P1 (GSTP1) and superoxide dismutase 2 (SOD2) has been observed in a number of breast cancer patients which can lead to an increase in cellular reactive oxygen species (ROS) (see reference 1005). Dysregulated methylation of Keap1 leading to breast tumor formation and increased methylation of Keap1 associated with poor prognosis in triple-negative breast cancer. Keap1 is a negative regulator of Nrf2, which can bind to antioxidant response elements in the promoter region of antioxidant genes and promote their expression. With increased Keap1 methylation, Nrf2 can activate antioxidant response elements, promoting antioxidant expression and leading to poor outcomes in triple-negative breast cancer (see reference 1006). Lower levels of miR-200a, which can degrade Keap1, are found in breast cancer, leading to higher levels of Keap1, blockade of Nrf2 and a decreased expression of antioxidants (see reference 1007). BRCA1, a breast cancer susceptibility gene, is known to increase levels of antioxidants GST, GPx and NQO1. Hypermethylation of the BRCA1 promoter can lead to increased sensitivity to platinum-based chemotherapy, most likely through a decrease in antioxidants leading to higher levels of therapy-derived ROS (see reference 1008).

While oxidative stress is known to cause genetic changes through direct DNA damage, it can also cause epigenetic changes leading to cancer initiation. ROS can cause an increase in DNA methyltransferase (DNMT) levels directly, leading to increased DNA methylation, or ROS-dependent DNMT increases can be due to other redox-sensitive factors, such as Ras or PI3K/Akt activation (FIG. 20A-C). ROS can also directly cause DNA methylation on redox sensitive promoters, such as the one found on the gene encoding for p16, a tumor suppressor gene (FIG. 20D). Additionally, it has been found that DNA damage caused by ROS can lead to DNA lesions, such as 8-hydroxyguanine, O6-methylguanine and single stranded DNA breaks, which in turn induce global hypomethylation through a lower interaction with DNMTs[46]. Oxidative stress can cause genomic instability and tumor formation through hypomethylation of both satellites and interspersed repeat sequences[46]. Recruitment of DNMTs to promoter regions has also been associated with recruitment of HDACs, which cause epigenetic modifications through remodeling of the chromatin structure of DNA. This modulates the accessibility of chromosomal loci, affecting the level of translation of certain genes[46].

Breast Cancer Specific Epigenetic Modifications of Oxidative Stress Genes

Lower expression of antioxidant proteins known to be epigenetically regulated, such as glutathione-S-transferase P1 (GSTP1) and SOD2, is seen in breast cancer tissue and increased promoter methylation has been identified as an important mechanism of this lower expression (FIG. 20E). Decreased levels of these proteins can cause ROS upregulation, leading to further activation of the downstream epigenetic-ROS signaling cascade.

Another oxidative stress factor that is under epigenetic control in breast cancer is Keap1. Keap1 is a known sensor of oxidative stress and negative-regulator of Nrf2. In breast cancer, it was found that aberrant methylation of Keap1 can lead to breast carcinogenesis and that increased methylation in triple-negative breast cancer is correlated with a worse prognosis, potentially through promotion of survival signaling (FIG. 20F). Interestingly, Keap1 methylation in ER-positive tumors contributes to a better prognosis. It is posited that the induction of Nrf2 that occurs with the epigenetic silencing of Keap1 leads to an increase in NQO1, which can prevent estrogen-mediated generation of ROS. Additionally, miR-200a, a micro RNA that is found to be epigenetically repressed in breast cancer, can negatively regulate Keap1, leading to Nrf2 activation (FIG. 20G).

The well-known breast cancer-susceptibility gene BRCA1, a marker for cancer development as well as chemosensitivity is susceptible to both germline mutations and methylation. In fact, hypermethylation of this gene has been correlated with enhanced sensitivity to chemotherapy, better survival and longer time to relapse (FIG. 20H). Further, BRCA1 expression can upregulate multiple genes related to ROS homeostasis, which can have profound effects on therapeutic outcomes in breast cancer patients discussed in next section.

Oxidative Stress Response and Adaptation Mechanisms in Breast Cancer

In order to compensate for increased oxidative stress, cancer cells have been identified to garner redox adaptive mechanisms that enhance their ability to detoxify ROS; exposure to constant oxidative stress selects for cells that can adapt to these conditions through a number of mechanisms. The strongest and most clear evidence for redox adaptation in breast cancer is the concurrent elevation of tissue markers of oxidative stress and increased expression and activity of antioxidants in breast cancer tissue samples relative to their normal counterparts.

The glutathione system (GSH-reduced, GSSG-oxidized) is the most abundant redox buffer within the cell[47], and any changes in the GSH to GSSG ratio will directly or indirectly affect various redox-sensitive cellular components. In a recent study, high GSH expression was associated with metastasis in breast cancer patients receiving chemotherapy[48]. Perry et al. noted that not only were GSH levels increased by two fold in breast cancer tissue relative to normal breast specimens, but that tissue from lymph node metastases showed a four-fold increase in GSH over normal tissue. Similarly, breast cancer brain metastases, which rely heavily on oxidative phosphorylation for energy generation and thus produce high levels of ROS, showed significant upregulation of glutathione-associated enzymes including glutathione reductase (GSR) and GSTP1, which help them maintain a reduced cellular environment[49]. These observations indicate that redox adaptation is crucial for metastatic breast cancer, as metabolic pressures such as nutrient deprivation that are associated with a foreign environment can promote oxidative stress[50]. Interestingly, BRCA1 upregulates the expression of GSTs and promotes a reduced state within the cell by promoting an increase in the GSH: GSSG ratio[51]. Thus, while these functions protect non-transformed cells against oxidative stress as a mechanism of cancer prevention, BRCA1 can promote a redox adaptive state in cells that have undergone carcinogenic transformation.

Another mechanism of redox adaptation is increased levels of SODs in breast cancer. In vitro studies have shown that overexpression of either SOD1 or SOD2 can inhibit breast cancer cell growth[52]. In vivo, infection of animals with an adenovirus expressing SOD1 or SOD2 decreased xenograft growth compared to controls[52]. Kattan et al. showed that there are differences in SOD2 expression between estrogen-dependent and estrogen-independent cancer cell lines, and that this expression regulates not only tumor cell growth and colony formation, but also doubling time, providing a link between SOD and the cell cycle[53]. A 2004 survey of breast cancer patients in Taiwan showed that SOD2, but not SOD1, expression was higher in cancer tissue than in malignancy-free tissue[54]. In studies conducted in our laboratory in two cellular models of aggressive breast cancer, redox-adapted populations of cells exposed to constitutive oxidative stress mediated by a small molecule dual kinase (ErbB1/2) inhibitor, lapatinib, exhibited enhanced expression of SOD1/2, overexpression of anti-apoptotic XIAP and increased GSH content relative to parental, lapatinib-sensitive cells[55]. These lapatinib-resistant cell lines were also cross-resistant to classical ROS-inducing treatments such as hydrogen peroxide and paraquat[55], as well as other commonly used anti-cancer drugs including sunitinib, gefitinib, bleomycin, capecitabine[56] and TRAIL[57].

Indeed identification of redox sensitive markers have been used by several groups to investigate the relationship between antioxidants and oxidative stress in breast cancer patient tissue. One such widely used marker is malondialdehyde (MDA) which has been observed to positively correlate with increases in SOD1/2 and GPx expression and activity in comparison to healthy breast tissue controls[58-61]. A similar study also observed increased SOD and GPx activity in breast cancer tissue relative to normal tissue, but they determined that MDA levels were slightly lower in the cancerous tissue, though serum levels of MDA were found to be elevated in breast cancer patients[62]. These studies also observed different results when measuring catalase activity, with some reporting an increase[60, 61] while others found a reduction[58, 59, 62] in tumor tissue compared to healthy controls. Another study found that MDA, LOOH (lipid hydroperoxides) and CD (conjugated dienes) were elevated in breast cancer tissue, and that this correlated with increased expression of SOD, catalase, GSH and GPx relative to uninvolved adjacent tissue[63]. Interestingly, the degree of increase in oxidative stress and antioxidant expression correlated with advanced disease; greater increases in both were observed in Stage III patient samples than in Stage I and II samples. Small sample size and the inherent heterogeneity of the disease likely played a role in these incongruous findings, but the common theme of enhanced antioxidant capacity in the presence of elevated oxidative stress remains consistent. Additionally, tumor stage may play a role in the finding that low antioxidant expression promotes oncogenesis, but tumor progression and increased ROS ultimately results in the need for upregulation of antioxidants to cope with increased oxidative stress.

Since oxidative stress serves as a selective pressure that promotes the survival of cells with increased antioxidant capacity, activation of survival signaling, induction of anti-apoptotic proteins and alterations in drug metabolism, all of which contribute toward drug resistance mechanisms. Thus, redox adaption is not only involved in cancer progression and metastasis, but also in the development of drug resistance. Many common breast cancer therapies work through the generation of ROS and thus may be rendered ineffective in cell populations that have adapted to cope with oxidative stress. Chemotherapies widely used in breast cancer include anthracyclines (doxorubicin), taxanes (paclitaxel, docetaxel), alkylating agents and platinum compounds (cisplatin, carboplatin), as well as radiation therapy, and all of these agents rely heavily on the induction of oxidative stress-induced apoptosis for their antitumor activity[16, 24, 64]. We have summarized the studies in the past 10 years that highlight the importance of redox adaptive mechanisms in breast cancer progression and therapeutic resistance (Tables 1.1, 1.2, 1.3).

TABLE 1.1

Antioxidant Expression and Function as Redox-Adaptive Mechanisms in Breast Cancer

| Sample Type | Description |
| --- | --- |
| Biochemical | GSH binds/inactivates metabolic intermediates of alkylating agents and platinum compounds, preventing cell damage [a] |
| MCF-7 | GPx overexpression correlates with resistance to doxorubicin [b] |
| | SOD expression linked to doxorubicin-and radio-resistance [c] |
| SUM149, SUM190 | Resistant cells had higher levels of SOD1/2 and GSH, relative to parental cells [d,e,f] |
| BCM2 Xenograft | Increased intracellular GSH associated with resistance to ROS-based drugs; brain metastatic cells 60-fold less sensitive to bortezomib due to treatment-mediated upregulation of GSH [g] |
| Patient (n = 63) | Increased Trx associated with low docetaxel response [h] |
| Patient (n = 44) | Trx, GST, Prx gene expression pattern may predict taxane response [i] |
| Patient (n = 63) | Increased GSH and GPx in hormone-negative tumors and expression predicted risk of metastasis [j] |

[a] Manda G, Nechifor MT, Neagu T. Reactive Oxygen Species, Cancer and Anti-Cancer Therapies. Current Chemical Biology. 2009; 3: 342-66.
[b] Kalinina EV, Chernov NN, Saprin AN, Kotova YN, Andreev YA, Solomka VS, Scherbak NP. Changes in expression of genes encoding antioxidant enzymes, heme oxygenase-1, Bcl-2, and Bcl-xl and in level of reactive oxygen species in tumor cells resistant to doxorubicin. Biochemistry (Mosc). 2006; 71(11): 1200-6.
[c] Guo G, Yan-Sanders Y, Lyn-Cook BD, Wang T, Tamae D, Ogi J, Khaletskiy A, Li Z, Weydert C, Longmate JA, Huang TT, Spitz DR, Oberley LW, Li JJ. Manganese superoxide dismutase-mediated gene expression in radiation-induced adaptive responses. Molecular and cellular biology. 2003; 23(7): 2362-78.
[d] Aird KM, Allensworth JL, Batinic-Haberle I, Lyerly HK, Dewhirst MW, Devi GR. ErbB1/2 tyrosine kinase inhibitor mediates oxidative stress-induced apoptosis in inflammatory breast cancer cells. Breast cancer research and treatment. 2012; 132(1): 109-19.
[e] Allensworth JL, Aird KM, Aldrich AJ, Batinic-Haberle I, Devi GR. XIAP Inhibition and Generation of Reactive Oxygen Species Enhances TRAIL Sensitivity in Inflammatory Breast Cancer Cells. Molecular cancer therapeutics. 2012.
[f] Williams KP, Allensworth JL, Ingram SM, Smith GR, Aldrich AJ, Sexton JZ, Devi GR. Quantitative high-throughput efficacy profiling of approved oncology drugs in inflammatory breast cancer models of acquired drug resistance and re-sensitization. Cancer letters. 2013; 17(13): 00386-8.
[g] Chen EI, Hewel J, Krueger JS, Tiraby C, Weber MR, Kralli A, Becker K, Yates JR, 3rd, Felding-Habermann B. Adaptation of energy metabolism in breast cancer brain metastases. Cancer Res. 2007; 67(4): 1472-86.
[h] Kim SJ, Miyoshi Y, Taguchi T, Tamaki Y, Nakamura H, Yodoi J, Kato K, Noguchi S. High thioredoxin expression is associated with resistance to docetaxel in primary breast cancer. Clinical cancer research: an official journal of the American Association for Cancer Research. 2005; 11(23): 8425-30.
[i] Iwao-Koizumi K, Matoba R, Ueno N, Kim SJ, Ando A, Miyoshi Y, Maeda E, Noguchi S, Kato K. Prediction of docetaxel response in human breast cancer by gene expression profiling. J Clin Oncol. 2005; 23(3): 422-31.
[j] Jardim BV, Moschetta MG, Leonel C, Gelaleti GB, Regiani VR, Ferreira LC, Lopes JR, de Campos Zuccari DA. Glutathione and glutathione peroxidase expression in breast cancer: An immunohistochemical and molecular study. Oncology reports. 2013.

TABLE 1.2

Modulation of Nrf2 and NF-κB Transcription Factors as Redox-Adaptive Mechanisms in Breast Cancer

| Target | Sample Type | Description |
| --- | --- | --- |
| NrF2 | Panel of cell lines | Increased expression led to higher GSH levels increasing resistance to electrophilic drugs [a,b]; activation led to high GSH levels, increased NF-κB activity and decreased ROS-mediated apoptosis [c]; overexpression causes chemoresistance [d]; Nrf2 inhibitor buthionine sulfoximine sensitized cells to paclitaxel [e]; siRNA knockdown of Nrf2 increased doxorubicin sensitivity [b] |
| | MCF-7 | Silencing Nrf2 ubiquitin ligase, Cul3, resulted in resistance to oxidative stress by $H_2O_2$, paclitaxel and doxorubicin [f] Activation upregulated γ-GCL, HO-1, Trx and Prx and decreased ROS production [g] |

TABLE 1.2-continued

Modulation of Nrf2 and NF-κB Transcription Factors as Redox-Adaptive Mechanisms in Breast Cancer

| Target | Sample Type | Description |
|---|---|---|
| NF-κB | MCF-7 | Constitutive activation correlated with taxane-and radio-resistance; NF-κB inhibition reversed resistance [h,i] |
| | BT-474 | NF-κB pathway activated by doxorubicin; NF-κB siRNA or inhibitory peptide reversed resistance [j] |
| | Cell lines, Patient (n = 439) | Activation associated with resistance to tamoxifen/aromatase inhibitors and decreased time to metastatic relapse despite adjuvant tamoxifen therapy [k] |
| | BT-474, Patient (n = 35) | Lapatinib induced NF-κB subunit RelA cytoprotective stress response; tumor biopsies show inverse correlation of p-RelA levels to lapatinib response [l] |

[a] Syed Alwi SS, Cavell BE, Donlevy A, Packham G. Differential induction of apoptosis in human breast cancer cell lines by phenethyl isothiocyanate, a glutathione depleting agent. Cell Stress Chaperones. 2012; 17(5): 529-38. doi: 10.1007/s12192-012-0329-3. Epub 2012 Feb. 17.
[b] Zhong Y, Zhang F, Sun Z, Zhou W, Li ZY, You QD, Guo QL, Hu R. Drug resistance associates with activation of Nrf2 in MCF-7/DOX cells, and wogonin reverses it by down-regulating Nrf2-mediated cellular defense response. Molecular carcinogenesis. 2012; 16(10): 21921.
[c] Bellezza I, Mierla AL, Minelli A. Nrf2 and NF-κB and Their Concerted Modulation in Cancer Pathogenesis and Progression. Cancers. 2010; 2(2): 483-97.
[d] Wang XJ, Sun Z, Villeneuve NF, Zhang S, Zhao F, Li Y, Chen W, Yi X, Zheng W, Wondrak GT, Wong PK, Zhang DD. Nrf2 enhances resistance of cancer cells to chemotherapeutic drugs, the dark side of Nrf2. Carcinogenesis. 2008; 29(6): 1235-43.
[e] Ramanathan B, Jan KY, Chen CH, Hour TC, Yu HJ, Pu YS. Resistance to paclitaxel is proportional to cellular total antioxidant capacity. Cancer research. 2005; 65(18): 8455-60.
[f] Loignon M, Miao W, Hu L, Bier A, Bismar TA, Scrivens PJ, Mann K, Basik M, Bouchard A, Fiset PO, Batist Z, Batist G. Cul3 overexpression depletes Nrf2 in breast cancer and is associated with sensitivity to carcinogens, to oxidative stress, and to chemotherapy. Mol Cancer Ther. 2009; 8(8): 2432-40. doi: 10.1158/535-7163.MCT-08-1186. Epub 2009 Jul. 28.
[g] Kim SK, Yang JW, Kim MR, Roh SH, Kim HG, Lee KY, Jeong HG, Kang KW. Increased expression of Nrf2/ARE-dependent anti-oxidant proteins in tamoxifen-resistant breast cancer cells. Free Radic Biol Med. 2008; 45(4): 537-46. doi: 10.1016/j.freeradbiomed.2008.05.011. Epub May 24.
[h] Sprowl JA, Reed K, Armstrong SR, Lanner C, Guo B, Kalatskaya I, Stein L, Hembruff SL, Tam A, Parissenti AM. Alterations in tumor necrosis factor signaling pathways are associated with cytotoxicity and resistance to taxanes: a study in isogenic resistant tumor cells. Breast Cancer Res. 2012; 14(1): R2.
[i] Guo N, Yan-Sanders Y, Lyn-Cook BD, Wang T, Tamae D, Ogi J, Khaletskiy A, Li Z, Weydert C, Longmate JA, Huang TT, Spitz DR, Oberley LW, Li JJ. Manganese superoxide dismutase-mediated gene expression in radiation-induced adaptive responses. Molecular and cellular biology. 2003; 23(7): 2362-78.
[j] Tapia MA, Gonzalez-Navarrete I, Dalmases A, Bosch M, Rodriguez-Fanjul V, Rolfe M, Ross JS, Mezquita J, Mezquita C, Bachs O, Gascon P, Rojo F, Perona R, Rovira A, Albanell J. Inhibition of the canonical IKK/NF kappa B pathway sensitizes human cancer cells to doxorubicin. Cell Cycle. 2007; 6(18): 2284-92. Epub 007 July 10.
[k] Zhou Y, Yau C, Gray JW, Chew K, Dairkee SH, Moore DH, Eppenberger U, Eppenberger-Castori S, Benz CC. Enhanced NF kappa B and AP-1 transcriptional activity associated with antiestrogen resistant breast cancer. BMC Cancer. 2007; 7: 59.
[l] Xia W, Bacus S, Husain I, Liu L, Zhao S, Liu Z, Moseley MA, 3rd, Thompson JW, Chen FL, Koch KM, Spector NL. Resistance to ErbB2 tyrosine kinase inhibitors in breast cancer is mediated by calcium-dependent activation of RelA. Molecular cancer therapeutics. 2010; 9(2): 292-9.

TABLE 1.3

Modulation of PI3K/AKT and ERK Signaling as Redox-Adaptive Mechanisms in Breast Cancer

| Sample Type | Description |
|---|---|
| MCF-7 | Tamoxifen resistant cells had increased p-ERK [a] Bcl-2 overexpression increased resistance to GSH modulatory agent neocarzinostatin [b] Introduction of constitutively active Ras or Akt conferred radioresistance to cells; inhibition of PI3K reversed Ras-mediated but not Akt-mediated radioresistance [c] Ectopic constitutively active Akt renders cells resistant to tamoxifen through increased p-NF-κB [d] |
| BT-474 | Endogenous constitutive activation of PI3K/Akt pathway associated with radiation resistance [e] |

TABLE 1.3-continued

Modulation of PI3K/AKT and ERK Signaling as Redox-Adaptive Mechanisms in Breast Cancer

| Sample Type | Description |
|---|---|
| SKBR-3, BT-474 cells and xenograft, Patient samples (n = 84) | PTEN null cells resistant to trastuzumab in vitro and in vivo [f] |
| Patient samples (n = 252) | Increased p-Akt correlated with lower response to aromatase inhibitors or selective estrogen receptor modulators and was associated with worse disease-free survival in patients receiving hormonal therapy [g] |
| Patient samples (n = 109) | High ERK positivity correlated with anthracycline resistance and poor survival following relapse [h] |
| Patient samples (n = 886) | ER-positive breast cancer patients with >1% p-ERK1/2 did not respond to tamoxifen, but p-ERK negative patients did respond [i] |

[a] Li Z, Wang N, Fang J, Huang J, Tian F, Li C, Xie F. Role of PKC-ERK signaling in tamoxifen-induced apoptosis and tamoxifen resistance in human breast cancer cells. Oncology reports. 2012; 27(6): 1879-86.
[b] Schor NF, Kagan VE, Liang Y, Yan C, Tyurina Y, Tyurin V, Nylander KD. Exploiting oxidative stress and signaling in chemotherapy of resistant neoplasms. Biochemistry (Mosc). 2004; 69(1): 38-44.
[c] Liang K, Jin W, Knuefermann C, Schmidt M, Mills GB, Ang KK, Milas L, Fan Z. Targeting the phosphatidylinositol 3-kinase/Akt pathway for enhancing breast cancer cells to radiotherapy. Mol Cancer Ther. 2003; 2(4): 353-60.
[d] DeGraffenried LA, Chandrasekar B, Friedrichs WE, Donzis E, Silva J, Hidalgo M, Freeman JW, Weiss GR. NF-kappa B inhibition markedly enhances sensitivity of resistant breast cancer tumor cells to tamoxifen. Ann Oncol. 2004; 15(6): 885-90.
[e] Soderlund K, Perez-Tenorio G, Stal O. Activation of the phosphatidylinositol 3-kinase/Akt pathway prevents radiation-induced apoptosis in breast cancer cells. Int J Oncol. 2005; 26(1): 25-32.
[f] Nagata Y, Lan KH, Zhou X, Tan M, Esteva FJ, Sahin AA, Klos KS, Li P, Monia BP, Nguyen NT, Hortobagyi GN, Hung MC, Yu D. PTEN activation contributes to tumor inhibition by trastuzumab,and loss of PTEN predicts trastuzumab resistance in patients. Cancer Cell. 2004; 6(2): 117-27.
[g] Tokunaga E, Kimura Y, Oki E, Ueda N, Futatsugi M, Mashino K, Yamamoto M, Ikebe M, Kakeji Y, Baba H, Maehara Y. Akt is frequently activated in HER2/neu-positive breast cancers and associated with poor prognosis among hormone-treated patients. Int J Cancer. 2006; 118(2): 284-9.
[h] Eralp Y, Derin D, Ozluk Y, Yavuz E, Guney N, Saip P, Muslumanoglu M, Igci A, Kucucuk S, Dincer M, Aydiner A, Topuz E. MAPK overexpression is associated with anthracycline resistance and increased risk for recurrence in patients with triple-negative breast cancer. Annals of oncology: official journal of the European Society for Medical Oncology/ESMO. 2008; 19(4): 669-74.
[i] Svensson S, Jirstrom K, Ryden L, Roos G, Emdin S, Ostrowski MC, Landberg G. ERK phosphorylation is linked to VEGFR2 expression and Ets-2 phosphorylation in breast cancer and is associated with tamoxifen treatment resistance and small tumours with good prognosis. Oncogene. 2005; 24(27): 4370-9.

Interesting Findings, Limitations and Future Directions

The levels of antioxidants found in breast cancer patients vary, with low levels of antioxidants hypothesized during progression (as this increases reactive oxygen species and leads to mutations) and high levels in late stages (compensatory and promotes proliferation/carcinogenesis). Peroxiredoxin is found in higher levels in malignant tumors over normal tissue but no link between these increased levels and clinical features have been found[65]. It is unknown if activation of receptor tyrosine kinase/G-protein coupled receptor signaling by $H_2O_2$ is due to inhibition of protein tyrosine phosphatases, or if there is direct activation[14]. These studies are some examples to highlight the fact that oxidative stress pathways are complex and measurements are challenging. This is compounded by the instability of compounds, variability in assays and a need for further development of newer assays that can allow for strong and reproducible correlations between oxidative stress and breast cancer clinical studies[17].

Role of estrogen in oxidative stress: Conflicting results show an inverse correlation between glutathione peroxidase expression and estrogen receptor (ER) status but little to no correlation when a larger number of cell lines used[20]. Further, despite lower levels of circulating estrogen, aging women have a higher incidence of ER+/HER-2− negative tumors than younger women, and have a better prognosis if they have triple negative breast cancer Inflammatory signals: TNF-α has been shown to act as both antitumorigenic (inflammation can induce apoptosis and inhibit tumorigenesis) and pro-tumorigenic (damage of DNA, inhibition of DNA repair, autocrine production of growth/survival factors, matrix metalloproteinase-induced remodeling and stimulation of NF-κB in resistant cell lines to increase resistance)[66]. Further, although inflammatory molecules have varied mechanism of action in breast cancer, modulation of aromatase seems to be a common point of convergence [31].

Concluding Remarks

It is clear that there is an intricate cross-talk between signaling pathways that regulate antioxidant capacity, redox-sensitive transcription factors, cell survival/death signaling and anti-apoptotic proteins in oxidative stress response and redox adaptation in cancer. Further, breast cancer is a highly heterogeneous disease and genetics, lifestyle, epigenetics, age and hormonal status, as discussed in this chapter, are in a dynamic relationship with redox status in cancer cells and its microenvironment. These redox adaptive mechanisms work in concert to regulate one another and participate in feedback loops. If the ultimate outcome is a decrease in oxidative stress sensitivity, there is a potential for development of acquired resistance to many anticancer therapies whose mechanism of action involves the generation of oxidative stress and/or selection of cancer cells highly refractory to therapeutic intervention.

Summary Points

Activation of key survival signaling pathways (FIG. 19), such as PI3K/Akt and ERK1/2, is mediated via hydrogen peroxide in many subtypes of breast cancer.

Survival pathways have the ability to activate redox-sensitive transcription factors such as Nrf2 and NF-κB; alternatively, these transcription factors can be activated by oxidative modification of their inhibitors or active site cysteines.

NrF2 and NF-κB can themselves regulate antioxidants (GSTs, NQOs, GPxs, catalase, SOD1/2, Trxs, metallothionein, HO-1 and γ-GCS).

Transcription factors and downstream redox-sensitive anti-apoptotic proteins (Bcl-2, Bcl-xL, cIAP1/2, XIAP, survivin, c-FLIP and TRAF1/2)[67-69], regulate each other during oxidative stress response in breast cancer cells.

Reference from Example 3

1. Droge W. Free radicals in the physiological control of cell function. Physiological reviews. 2002; 82(1): 47-95.
2. Han D, Williams E, Cadenas E. Mitochondrial respiratory chain-dependent generation of superoxide anion and its release into the intermembrane space. The Biochemical journal. 2001; 353(Pt 2): 411-6.
3. Winterbourn C C. Reconciling the chemistry and biology of reactive oxygen species. Nature chemical biology. 2008; 4(5): 278-86.
4. Hirst D G, Robson T. Nitrosative stress in cancer therapy. Frontiers in bioscience: a journal and virtual library. 2007; 12: 3406-18.
5. Nitta M, Kozono D, Kennedy R, Stommel J, Ng K, Zinn P O, Kushwaha D, Kesari S, Inda M D, Wykosky J, Furnari F, Hoadley K A, Chin L, DePinho R A, Cavenee W K, D'Andrea A, Chen C C. Targeting EGFR induced oxidative stress by PARP1 inhibition in glioblastoma therapy. PloS one. 2010; 5(5): e10767.
6. Ziech D, Franco R, Georgakilas A G, Georgakila S, Malamou-Mitsi V, Schoneveld O, Pappa A, Panayiotidis M I. The role of reactive oxygen species and oxidative stress in environmental carcinogenesis and biomarker development. Chemico-biological interactions. 2010; 188 (2): 334-9.
7. McCord J M, Fridovich I. Superoxide dismutase. An enzymic function for erythrocuprein (hemocuprein). The Journal of biological chemistry. 1969; 244(22): 6049-55.
8. Samoylenko A, Hossain J A, Mennerich D, Kellokumpu S, Hiltunen J K, Kietzmann T. Nutritional Countermeasures Targeting Reactive Oxygen Species in Cancer: From Mechanisms to Biomarkers and Clinical Evidence. Antioxidants & redox signaling. 2013.
9. Wells P G, McCallum G P, Chen C S, Henderson J T, Lee C J, Perstin J, Preston T J, Wiley M J, Wong A W. Oxidative stress in developmental origins of disease: teratogenesis, neurodevelopmental deficits, and cancer. Toxicological sciences: an official journal of the Society of Toxicology. 2009; 108(1): 4-18.
10. Indran I R, Hande M P, Pervaiz S. hTERT overexpression alleviates intracellular ROS production, improves mitochondrial function, and inhibits ROS-mediated apoptosis in cancer cells. Cancer research. 2011; 71(1): 266-76.
11. Matoba S, Kang J G, Patino W D, Wragg A, Boehm M, Gavrilova O, Hurley P J, Bunz F, Hwang P M. p53 regulates mitochondrial respiration. Science (New York, N.Y.). 2006; 312(5780): 1650-3.
12. Yagoda N, von Rechenberg M, Zaganj or E, Bauer A J, Yang W S, Fridman D J, Wolpaw A J, Smukste I, Peltier J M, Boniface J J, Smith R, Lessnick S L, Sahasrabudhe S, Stockwell B R. RAS-RAF-MEK-dependent oxidative cell death involving voltage-dependent anion channels. Nature. 2007; 447(7146): 864-8.
13. Ambrosone CB. Oxidants and antioxidants in breast cancer. Antioxidants & redox signaling. 2000; 2(4): 903-17.
14. Bartosz G. Reactive oxygen species: destroyers or messengers? Biochem Pharmacol. 2009; 77(8): 1303-15. doi: 10.016/j.bcp.2008.11.009. Epub November 24.
15. Forman H J, Maiorino M, Ursini F. Signaling functions of reactive oxygen species. Biochemistry. 2010; 49(5): 835-42. doi: 10.1021/bi9020378.
16. Trachootham D, Alexandre J, Huang P. Targeting cancer cells by ROS-mediated mechanisms: a radical therapeutic approach? Nature reviews Drug discovery. 2009; 8(7): 579-91.
17. Zhao Y, Robbins D. Manganese superoxide dismutase in cancer prevention. Antioxidants & redox signaling. 2013.
18. Robinson M F, Godfrey P J, Thomson C D, Rea H M, van Rij A M. Blood selenium and glutathione peroxidase activity in normal subjects and in surgical patients with and without cancer in New Zealand. The American journal of clinical nutrition. 1979; 32(7): 1477-85.
19. Maitra A, Wistuba, I I, Washington C, Virmani A K, Ashfaq R, Milchgrub S, Gazdar A F, Minna J D. High-resolution chromosome 3p allelotyping of breast carcinomas and precursor lesions demonstrates frequent loss of heterozygosity and a discontinuous pattern of allele loss. The American journal of pathology. 2001; 159(1): 119-30.
20. Esworthy R S, Baker M A, Chu F F. Expression of selenium-dependent glutathione peroxidase in human breast tumor cell lines. Cancer research. 1995; 55(4): 957-62.

21. Williams K J, Cowen R L, Stratford I J. Hypoxia and oxidative stress. Tumour hypoxia—therapeutic considerations. Breast cancer research: BCR. 2001; 3(5): 328-31.
22. Generali D, Berruti A, Brizzi M P, Campo L, Bonardi S, Wigfield S, Bersiga A, Allevi G, Milani M, Aguggini S, Gandolfi V, Dogliotti L, Bottini A, Harris A L, Fox S B. Hypoxia-inducible factor-1 alpha expression predicts a poor response to primary chemoendocrine therapy and disease-free survival in primary human breast cancer. Clinical cancer research: an official journal of the American Association for Cancer Research. 2006; 12(15): 4562-8.
23. Zhong H, De Marzo A M, Laughner E, Lim M, Hilton D A, Zagzag D, Buechler P, Isaacs W B, Semenza G L, Simons J W. Overexpression of hypoxia-inducible factor 1 alpha in common human cancers and their metastases. Cancer research. 1999; 59(22): 5830-5.
24. Brown N S, Bicknell R. Hypoxia and oxidative stress in breast cancer. Oxidative stress: its effects on the growth, metastatic potential and response to therapy of breast cancer. Breast cancer research: BCR. 2001; 3(5): 323-7.
25. Wincewicz A, Koda M, Sulkowska M, Kanczuga-Koda L, Wincewicz D, Sulkowski S. STAT3 and hypoxia induced proteins—HIF-1 alpha, EPO and EPOR in relation with Bax and Bcl-xL in nodal metastases of ductal breast cancers. Folia histochemica et cytobiologica/Polish Academy of Sciences, Polish Histochemical and Cytochemical Society. 2009; 47(3): 425-30.
26. Whelan K A, Schwab L P, Karakashev S V, Franchetti L, Johannes G J, Seagroves T N, Reginato M J. The Oncogene HER2/neu (ERBB2) Requires the Hypoxia-inducible Factor HIF-1 for Mammary Tumor Growth and Anoikis Resistance. The Journal of biological chemistry. 2013; 288(22): 15865-77.
27. Chen C L, Chu J S, Su W C, Huang S C, Lee W Y. Hypoxia and metabolic phenotypes during breast carcinogenesis: expression of HIF-1 alpha, GLUT1, and CAIX. Virchows Archiv: an international journal of pathology. 2010; 457(1): 53-61.
28. Blancher C, Moore J W, Talks K L, Houlbrook S, Harris A L. Relationship of hypoxia-inducible factor (HIF)-1alpha and HIF-2alpha expression to vascular endothelial growth factor induction and hypoxia survival in human breast cancer cell lines. Cancer research. 2000; 60(24): 7106-13.
29. Lal A, Peters H, St Croix B, Haroon Z A, Dewhirst M W, Strausberg R L, Kaanders J H, van der Kogel A J, Riggins G J. Transcriptional response to hypoxia in human tumors. Journal of the National Cancer Institute. 2001; 93(17): 1337-43.
30. Lithgow D, Covington C. Chronic inflammation and breast pathology: a theoretical model. Biological research for nursing. 2005; 7(2): 118-29.
31. Simpson E R, Brown K A. Minireview: Obesity and breast cancer: a tale of inflammation and dysregulated metabolism. Mol Endocrinol. 2013; 27(5): 715-25.
32. Ristimaki A, Sivula A, Lundin J, Lundin M, Salminen T, Haglund C, Joensuu H, Isola J. Prognostic significance of elevated cyclooxygenase-2 expression in breast cancer. Cancer research. 2002; 62(3): 632-5.
33. Khuder S A, Mutgi A B. Breast cancer and NSAID use: a meta-analysis. British journal of cancer. 2001; 84(9): 1188-92.
34. Simpson E R, Clyne C, Rubin G, Boon W C, Robertson K, Britt K, Speed C, Jones M. Aromatase—a brief overview. Annual review of physiology. 2002; 64: 93-127.
35. Clemons M, Goss P. Estrogen and the risk of breast cancer. The New England journal of medicine. 2001; 344(4): 276-85.
36. Sastre-Serra J, Valle A, Company M M, Garau I, Oliver J, Roca P. Estrogen down-regulates uncoupling proteins and increases oxidative stress in breast cancer. Free radical biology & medicine. 2010; 48(4): 506-12.
37. Nadal-Serrano M, Sastre-Serra J, Pons D G, Miro A M, Oliver J, Roca P. The ERalpha/ERbeta ratio determines oxidative stress in breast cancer cell lines in response to 17beta-estradiol. Journal of cellular biochemistry. 2012; 113(10): 3178-85.
38. Howlander N, Noone A M, Krapcho M, Garshell J, Neyman N, Altedruse S F, Kosary C L, Yu M, Ruhl J, Tatalovich Z, Cho H, Mariotto A, D. R. L, Chen H S, Feuer E J, Cronin K A, (eds). SEER Cancer Statistics Review, 1975-2010. National Cancer Institute Bethesda, Md., http://seercancergov/csr/1975_2010/, based on November 2012 SEER data submission. (based on November 2012 SEER data submission, posted to the SEER web site, April 2013).
39. Mates J M, Segura J A, Alonso F J, Marquez J. Intracellular redox status and oxidative stress: implications for cell proliferation, apoptosis, and carcinogenesis. Archives of toxicology. 2008; 82(5): 273-99.
40. Hou Z, Falcone D J, Subbaramaiah K, Dannenberg A J. Macrophages induce COX-2 expression in breast cancer cells: role of IL-1beta autoamplification. Carcinogenesis. 2011; 32(5): 695-702.
41. Donate L E, Blasco M A. Telomeres in cancer and ageing. Philosophical transactions of the Royal Society of London Series B, Biological sciences. 2011; 366(1561): 76-84.
42. Singhapol C, Pal D, Czapiewski R, Porika M, Nelson G, Saretzki G C. Mitochondrial telomerase protects cancer cells from nuclear DNA damage and apoptosis. PloS one. 2013; 8(1): e52989.
43. Aapro M, Wildiers H. Triple-negative breast cancer in the older population. Annals of oncology: official journal of the European Society for Medical Oncology/ESMO. 2012; 23 Suppl 6: vi52-5.
44. Cui H, Kong Y, Zhang H. Oxidative stress, mitochondrial dysfunction, and aging. Journal of signal transduction. 2012; 2012: 646354.
45. Rohan T E, Wong L J, Wang T, Haines J, Kabat G C. Do alterations in mitochondrial DNA play a role in breast carcinogenesis? Journal of oncology. 2010; 2010: 604304.
46. Ziech D, Franco R, Pappa A, Panayiotidis M I. Reactive oxygen species (ROS)—induced genetic and epigenetic alterations in human carcinogenesis. Mutation research. 2011; 711(1-2): 167-73.
47. Schafer F Q, Buettner G R. Redox environment of the cell as viewed through the redox state of the glutathione disulfide/glutathione couple. Free radical biology & medicine. 2001; 30(11): 1191-212.
48. Jardim B V, Moschetta M G, Leonel C, Gelaleti G B, Regiani V R, Ferreira L C, Lopes J R, de Campos Zuccari D A. Glutathione and glutathione peroxidase expression in breast cancer: An immunohistochemical and molecular study. Oncology reports. 2013.
49. Chen E I, Hewel J, Krueger J S, Tiraby C, Weber M R, Kralli A, Becker K, Yates J R, 3rd, Felding-Habermann B. Adaptation of energy metabolism in breast cancer brain metastases. Cancer Res. 2007; 67(4): 1472-86.
50. Singh B, Tai K, Madan S, Raythatha M R, Cady A M, Braunlin M, Irving L R, Bajaj A, Lucci A. Selection of metastatic breast cancer cells based on adaptability of their metabolic state. PLoS One. 2012; 7(5): e36510. doi: 10.1371/journal.pone.0036510. Epub 2012 May 3.
51. Bae I, Fan S, Meng Q, Rih J K, Kim H J, Kang H J, Xu J, Goldberg I D, Jaiswal A K, Rosen E M. BRCA1 induces antioxidant gene expression and resistance to oxidative stress. Cancer Res. 2004; 64(21): 7893-909.
52. Weydert C J, Waugh T A, Ritchie J M, Iyer K S, Smith J L, Li L, Spitz D R, Oberley L W. Overexpression of manganese or copper-zinc superoxide dismutase inhibits breast cancer growth. Free radical biology & medicine. 2006; 41(2): 226-37.
53. Kattan Z, Minig V, Leroy P, Dauca M, Becuwe P. Role of manganese superoxide dismutase on growth and invasive properties of human estrogen-independent breast cancer cells. Breast cancer research and treatment. 2008; 108(2): 203-15.
54. Er T K, Hou M F, Tsa E M, Lee J N, Tsai L Y. Differential expression of manganese containing superoxide dismutase in patients with breast cancer in Taiwan. Annals of clinical and laboratory science. 2004; 34(2): 159-64.
55. Aird K M, Allensworth J L, Batinic-Haberle I, Lyerly H K, Dewhirst M W, Devi G R. ErbB1/2 tyrosine kinase inhibitor mediates oxidative stress-induced apoptosis in inflammatory breast cancer cells. Breast cancer research and treatment. 2012; 132(1): 109-19.
56. Williams K P, Allensworth J L, Ingram S M, Smith G R, Aldrich A J, Sexton J Z, Devi G R. Quantitative high-throughput efficacy profiling of approved oncology drugs in inflammatory breast cancer models of acquired drug resistance and re-sensitization. Cancer letters. 2013; 17(13): 00386-8.
57. Allensworth J L, Aird K M, Aldrich A J, Batinic-Haberle I, Devi GR. XIAP inhibition and generation of reactive oxygen species enhances TRAIL sensitivity in inflammatory breast cancer cells. Molecular cancer therapeutics. 2012; 11(7): 1518-27.
58. Tas F, Hansel H, Belce A, Ilvan S, Argon A, Camlica H, Topuz E. Oxidative stress in breast cancer. Med Oncol. 2005; 22(1): 11-5.
59. Ray G, Batra S, Shukla N K, Deo S, Raina V, Ashok S, Husain S A. Lipid peroxidation, free radical production and antioxidant status in breast cancer. Breast Cancer Res Treat. 2000; 59(2): 163-70.
60. Portakal O, Ozkaya O, Erden Inal M, Bozan B, Kosan M, Sayek I. Coenzyme Q10 concentrations and antioxidant status in tissues of breast cancer patients. Clin Biochem. 2000; 33(4): 279-84.
61. Kumaraguruparan R, Subapriya R, Viswanathan P, Nagini S. Tissue lipid peroxidation and antioxidant status in patients with adenocarcinoma of the breast. Clin Chim Acta. 2002; 325(1-2): 165-70.
62. Punnonen K, Ahotupa M, Asaishi K, Hyoty M, Kudo R, Punnonen R. Antioxidant enzyme activities and oxidative stress in human breast cancer. J Cancer Res Clin Oncol. 1994; 120(6): 374-7.
63. Kumaraguruparan R, Kabalimoorthy J, Nagini S. Correlation of tissue lipid peroxidation and antioxidants with clinical stage and menopausal status in patients with adenocarcinoma of the breast. Clin Biochem. 2005; 38(2): 154-8.
64. Manda G, Nechifor M T, Neagu T. Reactive Oxygen Species, Cancer and Anti-Cancer Therapies. Current Chemical Biology. 2009; 3: 342-66.
65. Noh D Y, Ahn S J, Lee R A, Kim S W, Park I A, Chae H Z. Overexpression of peroxiredoxin in human breast cancer. Anticancer research. 2001; 21(3B): 2085-90.
66. Balkwill F. Tumor necrosis factor or tumor promoting factor? Cytokine & growth factor reviews. 2002; 13(2): 135-41.
67. Tian H, Zhang B, Di J, Jiang G, Chen F, Li H, Li L, Pei D, Zheng J. Keap1: one stone kills three birds Nrf2, IKKbeta and Bcl-2/Bcl-xL. Cancer Lett. 2012; 325(1): 26-34. doi: 10.1016/j.canlet.2012.06.007. Epub June 26.
68. Bharti A C, Aggarwal B B. Nuclear factor-kappa B and cancer: its role in prevention and therapy. Biochem Pharmacol. 2002; 64(5-6): 883-8.
69. Morgan M J, Liu Z G. Crosstalk of reactive oxygen species and NF-kappaB signaling. Cell Res. 2011; 21(1): 103-15.
70. Yook J I, Li X Y, Ota I, Hu C, Kim H S, Kim N H, Cha S Y, Ryu J K, Choi Y J, Kim J, Fearon E R, Weiss S J. A Wnt-Axin2-GSK3beta cascade regulates Snail1 activity in breast cancer cells. Nature cell biology. 2006; 8(12): 1398-406.
71. Lu Z, Xu S. ERK1/2 MAP kinases in cell survival and apoptosis. IUBMB Life. 2006; 58(11): 621-31.
72. Truong T H, Carroll K S. Redox regulation of epidermal growth factor receptor signaling through cysteine oxidation. Biochemistry. 2012; 51(50): 9954-65.
73. Badawi A F, Cavalieri E L, Rogan E G. Role of human cytochrome P450 1A1, 1A2, 1B1, and 3A4 in the 2-, 4-, and 16alpha-hydroxylation of 17beta-estradiol. Metabolism: clinical and experimental. 2001; 50(9): 1001-3.
74. Bolton J L, Thatcher G R. Potential mechanisms of estrogen quinone carcinogenesis. Chemical research in toxicology. 2008; 21(1): 93-101.
75. Tanaka T, Iwasa Y, Kondo S, Hiai H, Toyokuni S. High incidence of allelic loss on chromosome 5 and inactivation of p15INK4B and p16INK4A tumor suppressor genes in oxystress-induced renal cell carcinoma of rats. Oncogene. 1999; 18(25): 3793-7.
76. Browne E P, Punska E C, Lenington S, Otis C N, Anderton D L, Arcaro K F. Increased promoter methylation in exfoliated breast epithelial cells in women with a previous breast biopsy. Epigenetics: official journal of the DNA Methylation Society. 2011; 6(12): 1425-35.
77. Hitchler M J, Wikainapakul K, Yu L, Powers K, Attatippaholkun W, Domann F E. Epigenetic regulation of manganese superoxide dismutase expression in human breast cancer cells. Epigenetics: official journal of the DNA Methylation Society. 2006; 1(4): 163-71.
78. Barbano R, Muscarella L A, Pasculli B, Valori V M, Fontana A, Coco M, la Torre A, Balsamo T, Poeta M L, Marangi G F, Maiello E, Castelvetere M, Pellegrini F, Murgo R, Fazio V M, Parrella P. Aberrant Keap1 methylation in breast cancer and association with clinicopathological features. Epigenetics: official journal of the DNA Methylation Society. 2013; 8(1): 105-12.
79. Eades G, Yang M, Yao Y, Zhang Y, Zhou Q. miR-200a regulates Nrf2 activation by targeting Keap1 mRNA in breast cancer cells. The Journal of biological chemistry. 2011; 286(47): 40725-33.
80. Acharya A, Das I, Chandhok D, Saha T. Redox regulation in cancer: a double-edged sword with therapeutic potential. Oxidative medicine and cellular longevity. 2010; 3(1): 23-34.
81. Stefansson O A, Villanueva A, Vidal A, Marti L, Esteller M. BRCA1 epigenetic inactivation predicts sensitivity to platinum-based chemotherapy in breast and ovarian cancer. Epigenetics: official journal of the DNA Methylation Society. 2012; 7(11): 1225-9.

Example 4. Targeting Metastatic Dissemination in Inflammatory Breast Cancer

Background:

Inflammatory Breast Cancer (IBC):

IBC is the deadliest distinct subtype of locally advanced breast cancer (LABC). IBC typically presents with rapid onset of painful primary skin changes and breast swelling, often without an obvious breast mass. At time of diagnosis, almost all patients have lymph node involvement and 30% have distant metastases (Robertson, 2010). IBC disproportionately affects younger women from minority populations, and is therefore considered a health disparity. NCI Surveillance, Epidemiology, and End Results Program (SEER) data report IBC accounts for about 6% of all newly diagnosed BC in the U.S. annually, with higher global rates; however, incidence is increasing and previous estimates may be low due to difficulty in diagnosing IBC (Dawood, 2011a; Dawood, 2011b).

Dermal Lymphatic Invasion in IBC:

The presence of dermal lymphatic invasion in IBC is reported to be an independent predictor of clinical outcome after post-mastectomy RT (Abramowitz, 2009; Chu, 2013). Reports indicate there is a greater risk of residual disease, locoregional recurrence due to dermal invasion, and a 50% lower 5-year survival rate in IBC relative to non-IBC (Hance, 2005; Saigal, 2013). IBC often recurs on the chest wall after definitive treatment for the primary tumor. Morbidities associated with local recurrence include: pain, ulceration, odor, bleeding, lymphedema and the psychological distress of having visible local disease (Clemons, 2001; Robertson, 2010). To date, therapeutic options for patients with chest wall recurrence are limited.

Figure 21:
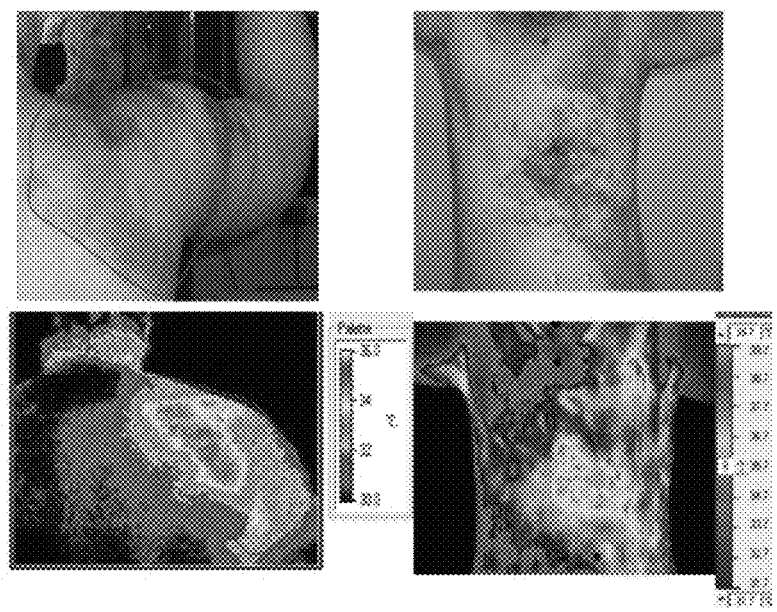
FIG. 21 contains photographic images and thermograms of patients with chest wall reoccurrence of breast cancer showing partial response after treatment. The elevated temperature of these lesions is most likely the result of increased metabolic rate, which is associated with the oxidative stress response, along with increased blood flow.

IBC Tumor Recurrence:

BC mortality is primarily attributed to relapse after initial treatment of the primary tumor, or tumor recurrence (Alvarez, 2013). Post-mastectomy RT and CT decrease risk of local failure and increase survival for patients with BC (Zagar, 2010). However, local failure risk is much higher (10-20% risk) in IBC patients, despite treatment with modern combinations of RT/CT (Abrous-Anane, 2011; Bates, 2012; Bourgier, 2012). Local treatment failure in IBC is associated with survival of populations of aggressive and therapeutically resistant residual tumor cells (RTC). RTC grow by forming unique tumor cell clusters with epithelial and stem-like characteristics, termed tumor emboli (TE). The presence of TE in lymphatic vessels, especially after local treatment failure, is the hallmark of IBC compared to other stage-matched LABC (Vermeulen, 2010). TE obstruct draining lymph vessels, which may explain some IBC clinical features (e.g. breast swelling, pain). It can also be envisioned that TE formation is part of the metastatic cascade in IBC patients (Nguyen, 2006; Vermeulen, 2010). Further, it has been proposed that TE drive the rapid local spread of cancer cells throughout the breast gland and skin in patients with local recurrence (FIG. 21). The most intriguing property of collectively invading cancer cells is their apparent preference for lymphatic dissemination (Chu, 2013; Giampieri, 2009).

Altered Oxidative Stress Response in IBC Pathobiology (FIG. 22):

The induction of reactive oxygen species (ROS) is a well-known consequence of RT and CT. Previous studies from the Devi (Initiating PI) and Dewhirst (Partnering PI) labs (independent and collaborative) in multiple breast cancer models have shown that CTs including the anthracyclines (doxorubicin), taxanes, alkylating agents, and platinum compounds, as well as RT, rely heavily on the induction of ROS/oxidative stress-induced apoptosis for their anti-tumor activities (Aird, 2012; Brown, 2001; Cao, 2013; Evans, 2014a; Manda, 2009; Trachootham, 2009; Viola, 2008). Normal cells tightly regulate redox homeostasis and eliminate excess ROS by upregulating intracellular antioxidants: 1) enzymes including superoxide dismutase (SOD), catalase and glutathione peroxidase (GPx); and 2) non-enzymatic radical scavengers such as vitamin E, ferritins, and thiols. Any imbalance between ROS accumulation and the ability of cells to neutralize these species can lead to oxidative stress. Cancer cells exhibit higher baseline levels of ROS due to inherent metabolic and signaling aberrations (Gorrini, 2013). To compensate for high levels of ROS and evade ROS-mediated apoptosis, cancer cells survive by activating redox adaptive mechanisms (FIG. 22), which include increased expression and activity of ROS-scavenging systems, antioxidants, pro-survival transcription factors and anti-apoptotic proteins (Devi, 2014c; Trachootham, 2009). Increased ROS in tumors contribute to high proliferation rates and accelerated metabolism despite upregulated antioxidant mechanisms. In particular, the ROS species peroxide ($H_2O_2$) exhibits preferential reactivity with protein thiols; this feature facilitates its action as a second messenger in signaling cascades (Forman, 2010). A persistent state of ROS stimuli (Toyokuni, 1995) perturbs signal transduction networks involved in cell growth, programmed cell death, transcription, and genomic instability (Aseervatham, 2013; Crawford, 1994; Kakehashi, 2013); all of these features are considered to be cancer hallmarks (Hanahan, 2011).

Figure 22:
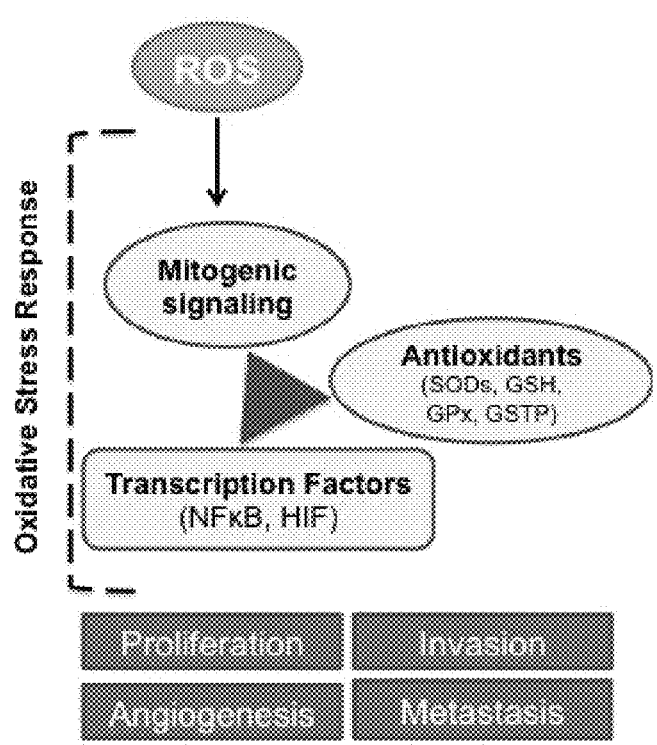
FIG. 22 is a schematic depiction of ROS signaling where enzymatic production and degradation of $H_2O_2$ can act as second messengers in signaling cascades.
Figure 23:
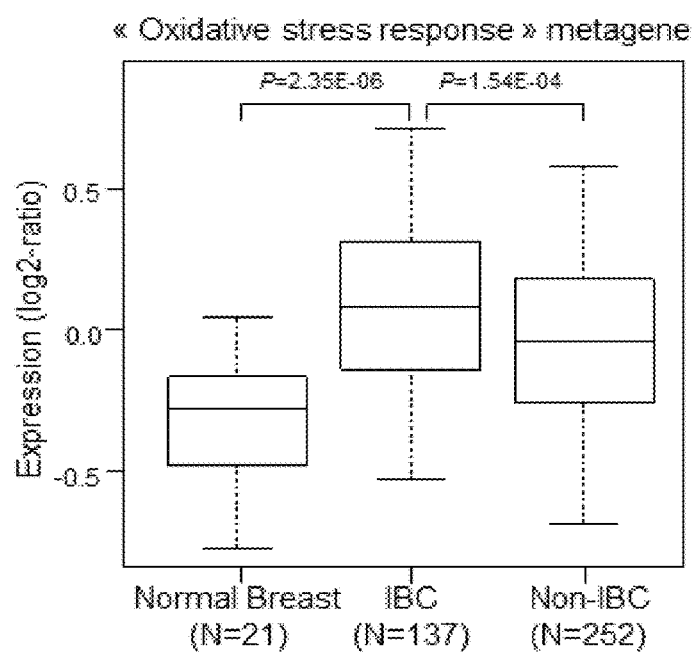
FIG. 23 shows the oxidative stress response signature in IBC clinical samples. Expression values of the "oxidative stress response" metagene set applied and reported as a box plot according to sample type from three cohorts. All BC samples were from diagnostic biopsies taken before systemic therapeutic intervention. p-values are indicated (t-test).

Supporting Studies:

The paucity of preclinical models and patient samples that recapitulate the pathobiology of tumor recurrence and therapy resistance in understudied cancers like IBC represent a significant challenge. Our lab has addressed this critical gap by generating unique isotype-matched breast cellular models that mimic tumor recurrence and acquired drug resistance with gene expression profiles similar to that observed in patient tumor datasets (Aird, 2010; Allensworth, 2015; Williams, 2013). As demonstrated in the above Examples, our laboratory has generated an oxidative stress response metagene by analyzing the genes activated and repressed in cultured IBC cells that mount a successful protective response to peroxide ($H_2O_2$) used as an ROS inducer. This metagene set ("oxidative stress response") was generated from a list (521 out of 532 genes retained after filtering) of upregulated genes, including predominantly NFκB and its target genes, antioxidants, heat shock proteins, DNA damage repair systems, and others previously validated as participants in the oxidative stress response (Human Oxidative Stress RT2 Profiler PCR Array, Qiagen). This metagene was then applied to analyze gene expression data from a cohort of IBC and non-IBC pre-treatment biopsies (Bertucci, 2014). Consistent with our hypothesis, oxidative stress response metagene values were higher in BC patient tissues (both IBC and non-IBC) than in normal breast samples (FIG. 23, p=2.35E-06 for IBC vs. normal). Further, IBC patient samples exhibited significantly higher values than non-IBC samples (p=1.54E-04), indicating an enhancement of protective mechanisms that enable this advanced breast cancer subtype to survive increased ROS levels. Using these models to study IBC tumor progression and drug resistance, we observed that elevated, but sublethal levels of ROS induce an oxidative stress response consisting of increases in nuclear transcription factor NFκB activity, anti-apoptotic protein XIAP, antioxidants SOD1/2, and hypoxia-inducible factor HIF-1. This oxidative stress response of increased pro-survival signaling, presumed protective, is postulated to lead to a paradoxical increase in proliferation, tumor growth, invasion, metastasis and promotion of advanced cancer subtypes like IBC (FIG. 22). The data are further supported by studies in the Devi lab that derived a clonal population of IBC cells that were selected under chronic drug-induced ROS stimuli and mimic recurrent tumor cells (rSUM149). These cells show increased in vivo tumorigenicity (FIG. 24A) and appearance of metastatic tumor cell clusters (FIG. 24B) compared to isotype-matched SUM149 parental tumor cells. Analysis of the tumor tissue reveals increased expression of pro-survival proteins and NFκB activation (FIG. 24C). This is significant, as previous studies using gene expression, immunohistochemistry and functional analysis have revealed the presence of a high number of nuclear factor-kappaB (NFκB) target genes with elevated expression in IBC versus nonIBC, suggesting that NFκB contributes to the phenotype of IBC (Lerebours, 2008; Van Laere, 2006; Van Laere, 2007). In addition, the Dewhirst (Partnering PI) lab was the first to report that HIF-1α (hypoxia inducing factor-1α), known to be regulated by NFκB activity (Gorlach, 2008), is upregulated by oxidative stress in proliferating, normoxic tumor cells (Cao, 2005; Moeller, 2004). This upregulation of HIF-1α can then drive lymphangiogenesis by increasing VEGF-C, D and PDGFR levels (Schito, 2012; Semenza, 2011). The NFκB-HIF1 interaction has also been shown to regulate EMT markers (Cheng, 2011). Together, these results support a general enhancement of the oxidative stress response in advanced breast cancer cells like IBC compared to their normal counterparts. Persistent oxidative stress can activate mitogenic signaling and the production of molecules with antioxidant activities which, if occurring in an environment rich in inflammatory cells, growth factors and activated stroma (like in IBC), can potentiate cancer progression and an aggressive, metastatic phenotype (Gorrini, 2013).

Strategies to overcome redox adaptation and enhance tumor cell death: Three compounds are used (FIG. 25) that have shown potential in preliminary studies to increase tumor cell death and enhance therapeutic efficacy. One compound is an FDA-approved drug used for alcohol abuse (disulfiram/DSF) with a strong safety profile spanning almost 50 years (Cook, 2014; Johansson, 1992). We have recently identified that DSF in combination with copper (Cu) can inhibit NFκB, induce ROS, decrease TE formation and in vivo tumor growth with minimal toxicity to normal cells as described in Example 1. Not to be bound by any theory, we believe this combination will be effective in preventing tumor emboli formation and metastasis. Further, The second class of drugs, called manganese (MnP) porphyrin-based superoxide dismutase (SOD) mimics, can promote oxidative stress-induced cell death and act as a radiosensitizer (Evans, 2014c; Gridley, 2007; Miriyala, 2012; Moeller, 2005). The third drug is a potent ribonucleotide reductase inhibitor called Didox (MTA in place with Molecules for Health, Inc.) that targets rapidly dividing tumor cells. Didox has shown in vitro efficacy against a variety of cancer cell lines (prostate, brain, bone marrow, liver and breast) both as a single agent and in combination with RT and CT (Al-Abd, 2013; Figul, 2003; Inayat, 2002; Raje, 2006; Shah, 2014). It has also been tested for safety and pharmacokinetics in a pilot clinical trial of advanced BC (Rubens, 1991).

Not to be bound by any theory, but our belief that therapy-induced oxidative stress response promotes tumor recurrence and lymphatic invasion in IBC. These experiments are to demonstrate: 1) in pre-clinical models, IBC tumor recurrence, dermal invasion, lymphangiogenesis and metastasis are increased after RT/CT; 2) NFκB activation drives oxidative stress response; 3) inhibiting treatment-related oxidative stress response will block tumor recurrence and enhance tumor cell death.

This study will provide mechanistic insights into IBC tumor recurrence and metastasis.

Experiment 1: Defining the Effects of Oxidative Stress on Recurrent Tumor Cells Leading to TE Formation and Progression Treatment-induced oxidative stress response activates survival signaling and selects for recurrent tumor cells (RTC) that form tumor clusters (TE) in IBC leading to increased local including dermal lymphatic invasion.

Using novel, high content 3D TE in vitro models, we will (a) image and conduct quantitative assessment of the effect of oxidative stress stimuli on TE formation and individual cell health parameters in the TE; (b) characterize invasion, migration of individual tumor cells within the in vitro TE; (c) evaluate NFκB activation pathway expression in oxidative stress-induced survival signaling in recurrent tumor cells.

RTC/TE 3D Culture Model:

Therapy-resistant residual tumor cells evade programmed cell death/apoptosis and by clonal expansion give rise to RTC. In IBC, RTC form specialized tumor cell clusters, called tumor emboli (TE). These TE then migrate through the lymphatic system and spread to distant organs. Our laboratory has applied a high-content assay (HCA) that utilizes combinations of nuclear and mitochondrial dyes, which to the best of our knowledge, is the first quantitative assay developed for simultaneous analysis of multiple cell health indicators of whole 3D TE and the cells within (FIG. 27; (Arora, 2014)). Importantly, TE formation in IBC allows for invasion of the local dermal lymphatic vessels, promoting rapid systemic metastasis (Lehman, 2013). To recapitulate this in vitro, we have combined the HCA TE assay with a model that uses cells growing in a polyethylene glycol (PEG) or hyaluronic acid (HA)-containing medium (this mimics the viscosity of lymphatic fluid) in a specialized shaker that simulates the oscillatory fluid shear forces present in in vitro lymphatics (Lehman, 2013). This HCA-TE-Lymphatic simulation model has distinct advantages of provides the closest approximation of the in vitro lymphatic milieu, where emboli invasion occurs; simultaneously images and quantitative measures of TE and tumor cells comprising the TE, which can also be analyzed for single cell gene expression studies; and incorporates high-throughput liquid handling allowing for large-scale dose- & time-response screening.

The first experiments define the effects of oxidative stress on recurrent tumor cells leading to TE formation and progression. Using novel, high content 3D TE in vitro culture models, (a) image and quantitatively measure effects of oxidative stress stimuli on TE formation and individual cell health parameters in TE are preformed, (b) TE invasion and in vitro lymphangiogenesis are assessed; (c) the oxidative stress response mechanism in recurrent tumor cells and TE as a whole by systematically targeting the NFκB activation pathway are evaluated.

This experiment will use western immunoblot analysis, immunofluorescence and/or NFκB-GFP reporter cell lines to assay for NFκB and target gene activation. HIF1 activation will serve as an NFκB activation marker when using the HIF-GFP reporter line or in assays testing protein expression (Gorlach, 2008). We will perform in vitro oxidative stress response measurements by directly monitoring ROS accumulation pre- and post-treatment by $H_2DCFDA$ flow cytometry (Aird, 2012). MitoTracker Red staining in HCA-TE assay will also allow us to quantitate mitochondrial membrane potential, an important feature during oxidative stress.

Live cell imaging and quantitative assessment of the effect of oxidative stress stimuli on TE formation and individual cell health parameters in TE.

Experiment 1A

While SUM149, SUM190, MDAIBC3 cells form true TE-like clusters (FIG. 27C), most other BC cells can form mammospheres in culture using ultra-low attachment plates and specialized media, which we will test using the HCA system (FIG. 27) to study multiple cell lines in a high-throughput manner. IBC and nonIBC tumor cells (Table 2) will be either irradiated (2-15 Gy) or treated with doxorubicin, cyclophosphamide, docetaxel or lapatinib (0-10 μM) to generate dose- and time-response (0-10 day) data.

TABLE 2

Figure 24:
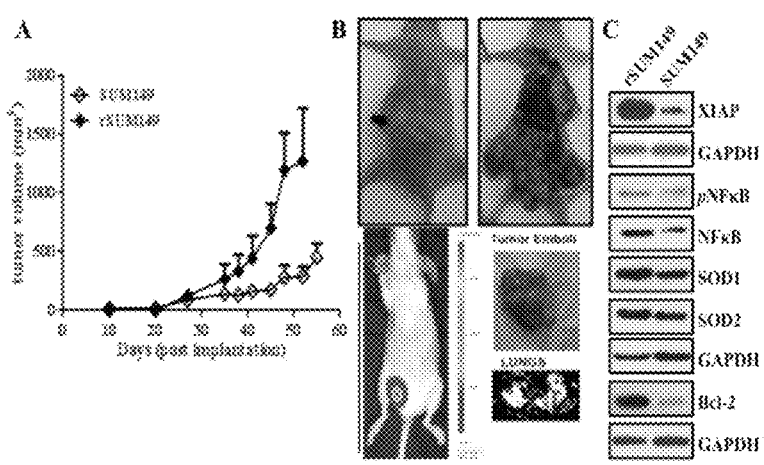
FIG. 24A shows in vivo tumorigenicity and molecular profiling of SUM149 (parental primary tumor cells) and rSUM149 (recurrent tumor model selected after chronic drug-induced ROS stimuli). rSUM149 cells show enhanced tumor growth in an orthotopic mammary fad pad model.
FIG. 24B depicts increased secondary metastases; Luciferase reporter activity showing primary tumor site; Metastatic IBC tumor resembles IBC patient emboli and localizes to the lungs.
FIG. 24C shows increased XIAP, NFκB and NFκB target protein (SOD2, Bcl2); and SOD1 expression in the rSUM149 model.

Characteristics of proposed cell models. (IBC-Inflammatory breast cancer; BC: Breast Cancer); ER: estrogen receptor; PR: progesterone receptor, EGFR/HER2: epidermal growth factor receptors). Currently, we have in hand mCherry-fluorescently labeled and luciferase tagged SUM149, SUM190 and 4T1 cells and HIF-1-GFP reporter lines (Cao, 2013). MCF-7 and HME1 mCherry lines and a stable NFκB reporter SUM149 cell lines are in development. We have also generated unique isotype-matched SUM149 and SUM190 derivatives that are clonal populations of cells selected under chronic oxidative stress stimuli-rSUM149, rSUM190 (Aird, 2012; Aird, 2010; Williams, 2013) that exhibit a tumor recurrent and multi-drug resistance phenotype (as shown in FIG. 24).

| Subtype | Receptor profile | Cell line |
|---|---|---|
| IBC (Basal) | ER-ve; PR-ve; EGFR-activated | SUM149 |
| IBC | ER-ve, PR-ve, HER2 + ve | MDA-IBC3 |
| IBC | ER-ve; PR-ve; HER2 +++ve | SUM190 |
| BC (Basal) | ER/PR/HER-2 negative | MDA-MB-231 |
| BC (Luminal) | ER + ve; PR + ve, HER2-ve | MCF-7 |
| BC (HER2) | ER-ve; HER-2+++ve; EGFR-activated | SKBR3 |
| Murine BC | ER-ve, PR-ve, HER-2-ve | 4T1 |
| Functional/ Imageable BC | Varied | 4T1 and SUM149-GFP, Luciferase and HIF1 and NFκB reporter lines |
| Resistant IBC isotmes | Isotype derivatives of rSUM149, rSUM190 SUM149, SUM190 | |

Experiment 1B

IBC cell lines will also be used in the lymphatic simulation model (3D TE) to assess formation in this particular matrix (nonIBC cells do not form TE in this system). We will also determine the ability of preselected RTC cell populations (Table 2, 3) to form TE at basal and post RT/CT. For both Expt. 1A and 1B, two treatment models are proposed: 1) pretreated 2D cells will be assessed for viability by trypan blue and equal numbers of viable cells from each treatment will be seeded in the 3D TE model to allow TE formation; 2) pre-formed emboli are treated to evaluate the effect of therapy in 3D culture. In addition to TE formation experiments, all treatments are conducted in parallel 2D adherent experiments for comparison of endpoints.

The number of mammospheres (FIG. 27A) and TE (FIG. 5C) formed in the treated cell lines will be compared to the control groups. Quantitative data will be generated from the HCA analysis for nuclear count, mammosphere/TE size, shape, texture, area, individual cell viability, and proliferation (FIG. 27F) and isolated for oxidative stress markers, gene and protein expression analysis.

Characterize Migration and Invasion of the Tumors Cells In Vitro.

The second experiments determine the effects of RT/CT-mediated oxidative stress on tumor cell invasion, tumor-vessel interactions and lymphangiogenesis in in vivo breast cancer models. Tumor cells expressing NFκB or HIF-1 reporter constructs are implanted in the mammary fat pad of transgenic mice with fluorescent lymph vasculature under a window chamber. In vitro high-resolution structural illumination or confocal intravital microscopy are preformed to simultaneous longitudinal imaging and quantification of (a) regional metastasis, (b) lymphangiogenesis, (c) NFκB/HIF-1 expression, (d) oxidative stress response in residual tumor cells post-RT/CT.

Experiment 1C

Figures 28A, 28B:
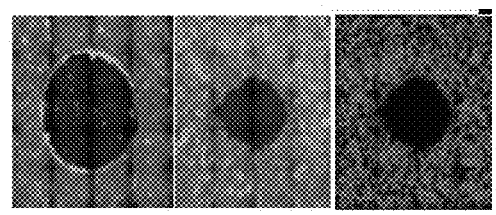
FIG. 28A shows high content endpoint migration assay and the invasion zone quantified after staining SUM149 treated cells with Hoechst (green) and YOYO-1 (red) dyes. Live (blue) vs. dead (red) cells shown for a single well of a 96 well plate. Well image with stopper in place for 48 h as a no-motility control (left) or removed at 0h to permit cell migration (right).
FIG. 28B shows the calculation of % area occupied for FIG. 28A.

BC cells will be irradiated or treated with doxorubicin, cyclophosphamide, docetaxel or lapatinib (based on $IC_{10}$, $IC_{50}$, $IC_{90}$ doses identified in Expt. 1A). The treated cells will be used in a high content migration assay we have optimized (FIG. 28), which allows us to analyze tumor cell migration along with viability and proliferation. This assay is superior to standard scratch wound assays as it is able to distinguish agents affecting cell migration from those also affecting viability.

Experiment 1D

For 3D invasion experiments, IBC tumor cells will first be grown in lymphatic simulating media and treated as listed in Experiment 1C. After treatment, TE will be harvested by low speed centrifugation (~400 rpm), and resuspended in undiluted Matrigel. This mixture will be coated on the underside of transwell inserts in a modified amoeboid movement assay (Lehman, 2013). Serum-free media will be added to the companion plate and growth media added to the top of the insert. After 24 h incubation, inserts will be gently aspirated and dried, followed by crystal violet staining and manual counting of TE clusters comprising >50 cells at 10×.

Results from these experiments will identify the effect of radiation and chemotherapeutic agents on the ability of cells surviving therapy to form TE, and will allow us to compare IBC and nonIBC RTC TE formation. These experiments will generate quantitative measures of cell health indicators in individual cells in the TE, invasion and migration potential of the recurrent tumor cells/TE and effect of the RTC/TE on in vitro lymphangiogenesis. These experiments will allow for rapid, economical screening and provide clarity on treatment dose, time, and efficacy parameters that can be used for the in vivo studies. Expression analysis of NFκB pathway, HIF1 activity and oxidative stress response measurements obtained will reveal functional correlations with TE growth, invasion, and migration.

Experiment 2: Determine the Effects of RT/CT-Mediated Oxidative Stress on Tumor Cell Invasion, Tumor-Vessel Interactions and Lymphangiogenesis on In Vivo BC Models Residual tumor cells often survive treatment through compensatory oxidative stress-mediated survival signaling and serve as reservoirs for tumor recurrence, invasion, and metastasis.

Approach:

Breast tumor cells expressing NFκB or HIF1 reporter constructs will be implanted under murine window chambers in transgenic mice with fluorescent (different wavelength) lymph vasculature. This will allow simultaneous longitudinal imaging and quantification by in vivo high-resolution structural illumination or confocal—intravital microscopy of a) tumor initiation, b) regional metastasis, c) dermal lymphatic invasion, d) lymphangiogenesis, e) NFκB/HIF-1 expression, and f) oxidative stress response in RTC post-RT/CT.

Figure 29:
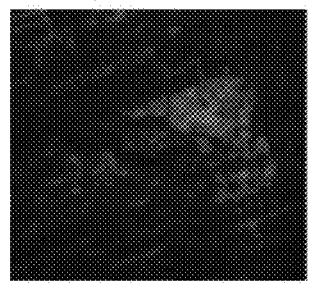
FIG. 29 shows an image obtained from a transgenic mouse with mammary fat pad window chamber that expresses m-Cherry red fluorescent reporter gene in vascular endothelium, under control of the Tie2 promoter. Tumor cells (blue fluorescence) in this window were labeled with a lipid dye, DiD, prior to transplant.
Figure 30:
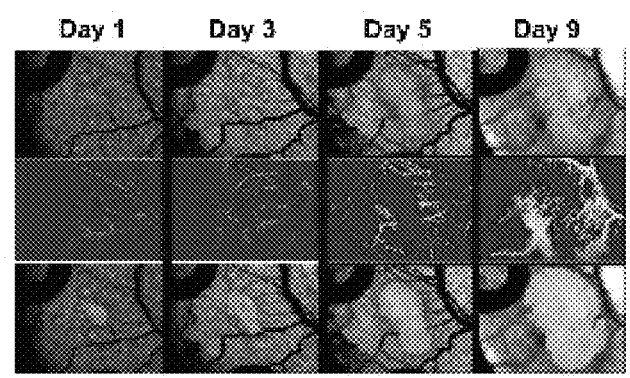
FIG. 30 shows serial observation of hemoglobin saturation and HIF1 activity during early tumor growth. An increase in arterial $pO_2$ is the first reaction to the presence of tumor cells (top), followed by increases in venular $pO_2$ (middle). During the continued process of angiogenesis, HIF-1 expression level increases, suggesting that improvements in $pO_2$ within the growing tumor mass are not alleviating HIF-1 activity (bottom) (Dewhirst, 2007).
Figure 31:
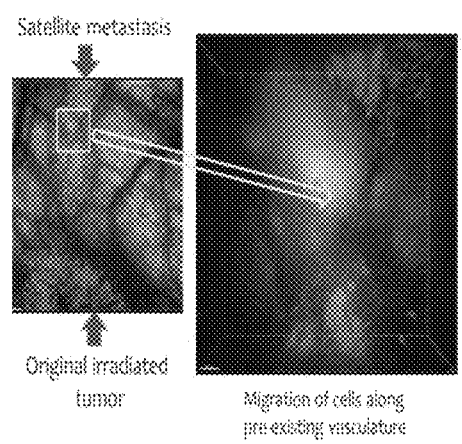
FIG. 31 shows post-RT Recurrent tumor cells show increased tumor invasion and regional migration. Tumor cells migrate along vascular network to unirradiated site. And lead to formation of satellite metastases. The original tumor, with RFP reporter, is at the bottom. Two satellite tumors, in unirradiated tissue, are seen following a track toward the 12 o'clock position. This was not observed in control tumors. Size: 4 mm square. Confocal microscopy image; yellow box outlines area bridging tumor sites; red arrow indicates location of original and satellite tumors. Yellow arrow shows path of tumor cell migration.
Figure 32:
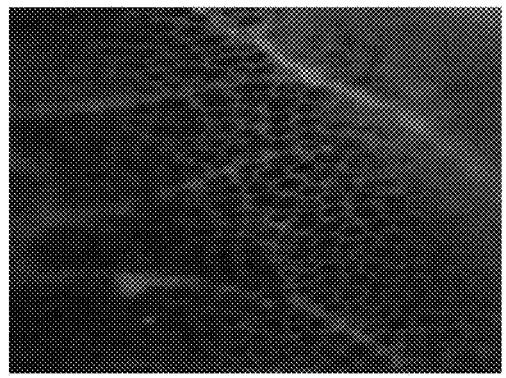
FIG. 32 shows lymphatic vasculature visualization in the mammary fat pad within 5-10 min using fluorescently-labeled dextran.

Murine Window Chamber Model:

This approach (Palmer, 2011) involves surgical implantation of a titanium frame to support a glass window over the mouse's skin (FIG. 29) either in the dorsal or inguinal mammary fat pad sites. Fluorescently labeled tumor cells are then injected into the skin beneath windows implanted in BALB/c or nude mice (Moeller, 2004). High-resolution intravital microscopy is used to serially image the movement of cells (Betof, 2015; Cao, 2005; Li, 2000; Shan, 2004), thereby obtaining valuable multiparametric functional, molecular and quantitative information in vivo. RFP-tagged cells will enable us to visualize and quantify IBC cell infiltration into the lymphatics. This technique is beneficial in that we can image the same tumor and lymphatics for 7-10 days. Preliminary data show measurement of HIF1 levels, an NFκB target and biomarker for oxidative stress response using dual-tagged reporter cells (FIG. 30). Further, in a recent pilot study using a dorsal skin fold window chamber model, serial microscopic measurements were taken in live tumor-bearing mice before and after radiation exposure to show that tumor cells migrated along the external surface of tumor-associated vasculature adjacent to the irradiated tumor to the secondary site (FIG. 31). The Partnering PI has used these models for more than 30 years in fluorescence microscopy imaging of the tumor microenvironment (Fontanella, 2013; Hanna, 2013; Palmer, 2012; Palmer, 2011). These models enable high resolution, longitudinal monitoring of dynamic functional processes, which is not possible using other modalities. Of particular relevance, as shown in our supporting data below, we have applied such models to study oxidative stress as it is altered dynamically by therapy, while simultaneously assessing other parameters (e.g. angiogenesis, lymphangiogenesis, hypoxia, and tumor growth and migration). These capabilities are critical to definitively test our hypothesis. Other available imaging modalities do not offer the special resolution or the specificity to distinguish the required endpoints, and histological methods only allow for a single time point to be studied so are not well suited for understanding dynamic processes as we propose here.

Determine Effect of Oxidative Stress on Regional Invasion

Experiment 2A

We will use the inguinal mammary fat pad window chamber model, which allows for tumor growth in the natural microenvironment closer to the draining lymph nodes. 4T1 and SUM149 RFP/GFP reporter cell models will be implanted in the mammary window chamber model. When the tumors in the window reach a diameter of 2-4 mm post-implantation, we will acquire baseline-imaging data. Sentinel animals (5 mice/treatment/dose) will be treated with RT (5, 10 and 15 Gy) or doxorubicin (5, 10 mg/kg) systemically through tail vein injections to determine the optimal dose for induction of oxidative stress response. The single optimal doses of RT/CT will then be used for the remainder of the experiments, with 10 mice/group of the identified dose of RT and doxorubicin administered once. Longitudinal imaging of tumor cells and their movement will be performed using high-resolution intravital microscopy (Palmer, 2012; Palmer, 2011). Vascular length density (VLD) will be calculated to determine if there is a correlation between angiogenesis and metastasis, as we have previously reported that tumor-associated vasculature can provide a network for tumor cells to attach and move (Li, 2000). Hemoglobin saturation will be measured to provide a non-invasive assessment of oxygenation. This will aid in understanding if HIF-1 upregulation is influenced by hypoxia.

Experiment 2B

To permit serial in vivo monitoring of tumor free-radicals, window chamber tumors will be suffused with media containing $H_2DCFDA$, which indicates the presence of free-radicals/oxidative stress. DCFDA, whose fluorescence is not free radical-responsive, will be used in a control group of tumors to rule out nonspecific radiation effects on dye accumulation.

Experiment 2C

Resected tumors will be rendered transparent to visible light via optical-clearing and imaged using optical-CT/emission-CT (oCT/eCT) for HIF-1 or NFκB activation, vessel density, and regional migration/metastasis. Because the tumor cells constitutively express RFP or mCherry, which is not destroyed with optical-clearing, it is possible to follow these cells with fluorescence imaging and quantify the metastatic satellite tumor burden in these tissues with oCT/eCT (Oldham, 2008; Thomas, 2010).

Experiment 2D

Approximately seven days after treatment and the completion of the longitudinal imaging series, tumors and surrounding normal tissue will be removed and assessed for signaling and oxidative stress response by measuring SOD activity, protein expression and total glutathione content. Immunohistochemistry, protein and RNA analysis will also be performed on a portion of the resected tumor. To further confirm the identity of recurrent tumor cells (RTC) post-RT/CT, SUM149 reporter cells that have migrated to the vasculature will be isolated and ALDH levels, a marker of stem-like cells, will be quantified using the ALDEFLUOR kit and remaining cells will subsequently used in follow-up assays as elaborated in Experiment 1.

Assessment of In Vivo Lymphangiogenesis.

For these experiments, we will utilize a ProxTom lymphatic vessel reporter B6 mouse (Truman, 2012), which has a TdTomato reporter present in the lymphatic system, backcrossed to nude mice. Through the use of the Duke breeding core facility that has expertise generating cross-strains of different mice, we will select for nude mice exhibiting the reporter at each generation (up until the $8^{th}$ generation), which by then will have allowed for complete backcrossing. SUM149-GFP cells will be implanted during insertion of the mammary window chamber and treated once with the dose of RT or doxorubicin that gave the highest oxidative stress response used in Expt. 2A (10 mice/group), which will allow us to track the invasion of tumor cells into the lymphatic vasculature.

For this experiment, similar quantitative measurements as elaborated in the window chamber model in Expt. 1A will be carried out in vivo using high-resolution intravital microscopy (Palmer, 2012; Palmer, 2011). Lymph vessel length density (LVLD) will be calculated to assess correlation between lymphangiogenesis and metastasis.

Table 3 summary of in vivo studies allows us to visualize and quantify in in vivo pre-clinical models the local migration induced by RT/CT-mediated oxidative stress. Through use of reporters, ROS-specific dyes, and endpoint analyses, we can correlate migration endpoints with oxidative stress response. This will improve our knowledge of important signaling parameters that are modulated during migration and initiation of tumor metastasis. Further, using unique lymphatic reporter systems, we can elucidate tumor cell interaction with lymphatic vessels to address the key feature of IBC cells: ability to undergo dermal, intralymphatic invasion and lymphangiogenesis. We expect our data will show enhanced migration, invasion and regional metastases after RT/CT through an increase in oxidative stress response, particularly activation of NFκB and downstream HIF1. We also expect to identify additional downstream proteins that are upregulated during RT/CT-mediated oxidative stress response, which will allow us to find new targets to prevent tumor recurrence.

stress response strategy showing the most potent efficacy in the in vitro TE assays and window chamber models will be extended to test in SUM149-, and 4T1-Luc tumors to suppress tumor growth and secondary local and distant metastasis as a single agent and in combination with RT and selected CT.

Figure 33A:
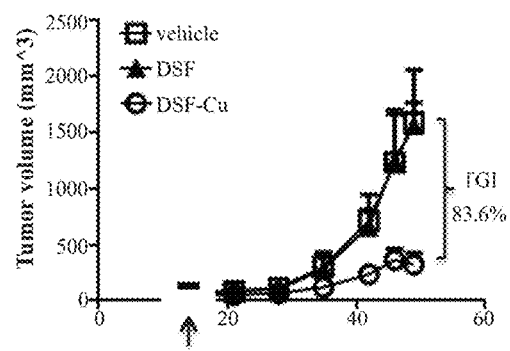
FIG. 33A shows DSF+Cu effectively inhibits IBC tumor growth through inhibition of NFκB activation, demonstrated by in vivo subcutaneous tumor growth studies of IBC PTC with vehicle, DSF alone or DSF+Cu. Arrow shows start of treatment in palpable tumor-bearing mice.
Figure 33B:
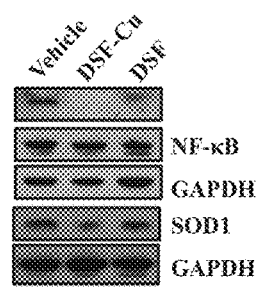
FIG. 33B depicts a western immunoblot analysis of IBC tumors show decreased p NFκB and SOD1 antioxidant expression in DSF-Cu treated samples.

FIG. 24 shows comparison of orthotopic mammary fat pad tumors arising from a PTC line (SUM149 tested) to matched RTC derivative (rSUM149), revealing rSUM149 had enhanced tumor growth and secondary local and distant organ (lung) metastasis that mimics the morphology of TE (Lehman, 2013). Further, rSUM149 tumors similar to in vitro and gene expression analysis of post-treatment patient tumors had high oxidative stress response markers [XIAP, NFκB and NFκB targets (antiapoptotic protein Bcl-2 and antioxidant SOD2)]. Recently, the Initiating PI lab has reported preclinical studies with DSF in IBC models (multiple PTC and RTC tested) and identified that DSF acts as a copper ionophore by bypassing the need for membrane transporters to induce copper-dependent oxidative stress selectively in tumor cells, suppressing NFκB activation and mediating anti-tumor efficacy (representative data in FIG. 33 (Allensworth, 2015). Further, data from the partnering PI lab

TABLE 3

Summary of 4T1 and SUM149 Murine Window Chamber Tumor Models

| Experiment | Treatment | Endpoints (Primary, Secondary) | Mice |
|---|---|---|---|
| Exp. 1a—Determination of RT/CT dosing for oxidative stress [Sentinel Animals] | Vehicle<br>RT (5, 10, 15 Gy)<br>Doxorubicin (5, 10 mg/kg) | Tumor ROS (H$_2$DCFDA) | N = 5/gp |
| Exp. 1b, c, d—Effect of oxidative stress on regional invasion [HIF1 and NFκB reporter cell lines] | Vehicle<br>RT (Optimum dose from sentinel animals)<br>Doxorubicin (Optimum dose from sentinel animals) | Regional invasion, migration & metastasis<br>NFκB/HIF-1 levels<br>VLD<br>ROS and stress response | N = 10/gp |
| Exp. 2—Assess in vivo lymphangiogenesis [GFP cell lines] | Vehicle<br>RT (selected dose from above)<br>Doxorubicin (selected dose from above) | See Exp. 1<br>Endpoint (mRNA, protein activity) | N = 10/gp |

Figure 26:
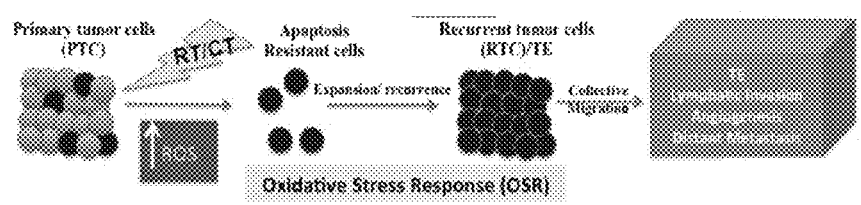
FIG. 26 depicts a model of how tumor recurrence can develop in IBC when therapy (RT/CT/Targeted) fails to kill all primary tumor cells. In IBC, this involves expansion of residual, apoptosis resistant tumor cells, induction of oxidative stress response, leading to increased TE formation, collective migration, propensity for dermal lymphatic invasion, and metastatic progression.

Experiment 3: Identify Oxidative Stress Response Modulating Strategies to Inhibit Recurrent Tumor Cells, Prevent Metastatic Progression, and Enhance IBC Tumor Cell Kill The third experiments identify oxidative stress response modulating strategies to inhibit recurrent tumor cells, prevent metastatic progression, and enhance IBC tumor cell kill. DSF+Cu; MnP-Ascorbate; Didox (a) alone and, (b) in combination with RT and select CT are used to target the redox adaptive mechanisms of breast cancer cells using mammary fat pad window chamber and orthotopic murine tumor models. FIG. 26 shows the models of action described below. Strategies that enhance cell death in recurrent tumor cells during definitive therapy of primary IBC tumors or inhibit chest wall recurrence will reduce the risk of failure to control local disease and lead to much better patient survival/outcomes.

Figure 25:
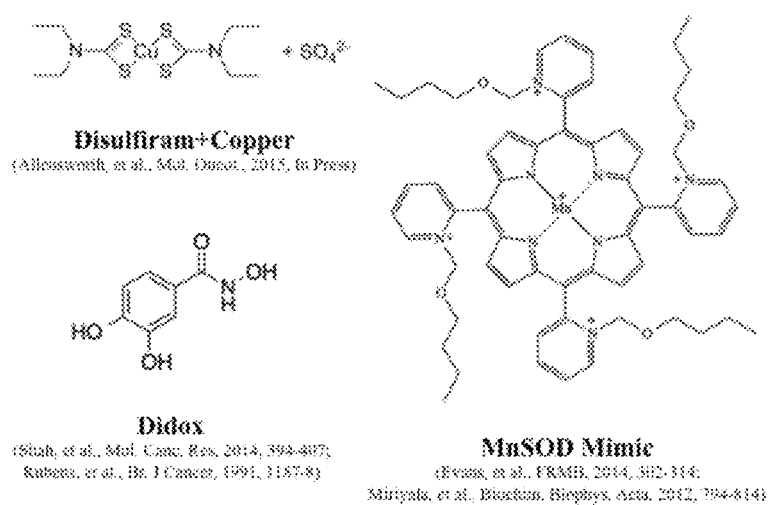
FIG. 25 depicts the compounds to target the oxidative stress response to inhibit tumor growth and prevent metastasis.
Figure 34:
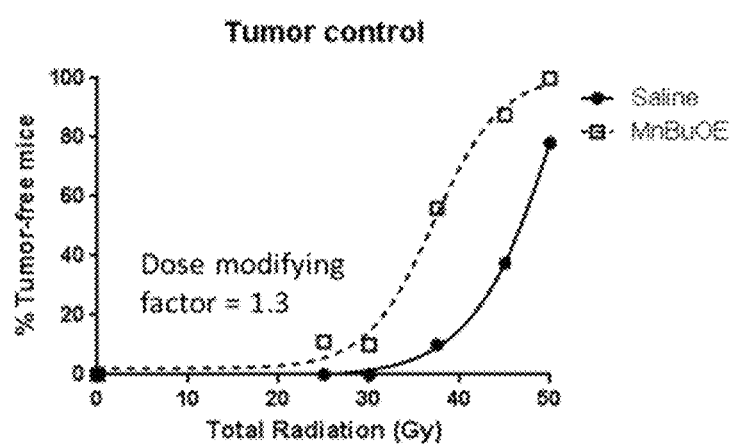
FIG. 34 shows MnSOD mimic improves tumor control following RT, while protecting normal tissue. Treatment with MnBuOE pre- and post-RT made tumor xenografts more radiosensitive as indicated by a left shift of the tumor radiation control curve. The TCD50 doses (total RT applied in 5 fractions) were 47Gy (saline controls) and 36.5Gy (MnBuOE), giving a 1.3 dose modifying factor.
Figure 35:
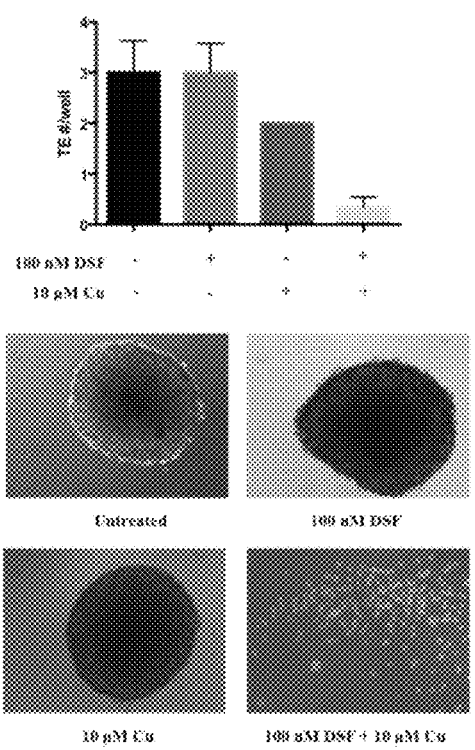
FIG. 35 shows DSF-Cu inhibits in vitro tumor emboli formation shown by SUM149 cells in lymphatic simulating tumor emboli model (Lehman, 2013) treated with DSF, Cu and DSF-Cu at the time of seeding. Spheroids manually counted using phase contrast microscopy on day 4 (N=2, replicates=6).

We will test the efficacy of three redox modulatory strategies (FIG. 25; Background)—DSF+Cu, MnSOD mimic and Didox in 1) SUM149, rSUM149, and 4T1-HIF-1 and NFκB reporter cells for their ability to suppress in vitro TE formation; 2) prevent dermal invasion, lymphangiogenesis in the in vivo window chamber models; 3) oxidative has shown that a MnSOD mimic abrogates RT-induced oxidative stress in a murine window chamber model, yet the addition of a MnSOD mimic sensitizes xenograft tumors to RT by a dose modifying factor of 1.3 (FIG. 34)

Experiment 3A: Effect of Treatment Strategies on In Vitro Tumor Emboli Formation We will test the in vitro efficacy of redox modulating agents, DSF-Cu, MnSOD mimic, Didox (alone and in combination with RT/CT) to suppress in vitro TE formation and elucidate oxidative stress response and signaling. We will initially employ SUM149, rSUM149, and 4T1-HIF-1 and NFκB reporter cells (study design similar to protocols explained in Experiment 1—FIG. 13).

Experiment 3B: Short-Term Murine Window Chamber Model for Assessment of Treatment on Invasion and Satellite Metastasis This experiment will determine in vivo efficacy of the redox modulating agents (alone and in combination with RT or doxorubicin) for their ability to suppress dermal invasion and lymphangiogenesis in mammary fat pad window chamber models (study design similar to protocols explained in Experiment 2).

Experiment 3C: Determination of Treatment Strategies on Long-Term Tumor Growth Delay and Metastatic Model The in vivo efficacy of the most potent oxidative stress response-targeting agent alone and in combination with RT and select CT will be quantified in a murine orthotopic mammary tumor growth model. In this experiment, the strategy that shows the most potent efficacy in the in vitro TE assays and the window chamber models will be extended to test in SUM149-luc and 4T1-Luc in vivo tumors to suppress tumor growth and secondary local and distant metastasis as a single agent and in combination with RT and selected CT. SUM149-luc and 4T1-luc will be implanted orthotopically ($5 \times 10^6$ cells in 50 µL) in the fourth mammary fat pad of nude or BALB/c mice, respectively. When the tumors reach 100 mm$^3$, treatment groups (15 mice/group) will include: 15 Gy RT (once), 10 mg/kg doxorubicin (once/week, iv, tail vein), 6 mg/kg docetaxel (once/wk, ip), 100 mg/kg lapatinib (twice daily, po) (Kurokawa, 2013), 50 mg/kg of DSF+0.5 mg/kg Cu (daily, ip), MnP (loading dose of 0.2 mg/kg, followed by maintenance dose of 0.1 mg/kg 3 days/week), 425 mg/kg didox (daily, ip) and appropriate vehicle treated mice groups. Results from experiment and single agent studies in this aim will also inform us about optimal dose and combinations for further testing in the tumor models. Longitudinal luciferase imaging of both primary tumors and distant metastases will be conducted every 3 days using a Xenogen IVIS Lumina XR system. Seven days post-treatment, a set of mice will have their primary tumors surgically removed and be followed for secondary tumors (local dermal and distant organ) to mimic a clinical regimen of RT/CT and then surgery. Tumor volume [(length×width$^2$)/2] in the remaining mice will be monitored until tumors reach 1500 mm$^3$ or mice show signs of morbidity. The fold-change in tumor volume will be normalized to baseline size and plotted over the indicated points to generate tumor growth graphs using GraphPad Prism. Enhancement ratios will be determined by dividing the average tumor volumes of tumors receiving RT/CT alone by those receiving RT/CT in combination. Distant metastases will be monitored using the IVIS Lumina XR system. In addition, optical-clearing and imaging via oCT/eCT of lung tissues will be performed to quantify the extent of lung metastasis (Oldham, 2008; Thomas, 2010). Vascular length density will also be quantified. Resected tumors will be used to assay for oxidative stress along with other parameters derived in previous RNA/protein analyses. Excised tumors will be processed for H&E staining (to assess tumor differentiation); immunohistochemical analysis of NFκB, XIAP, SOD1 and HIF1 and proliferation index (Ki67). Epithelial, mesenchymal and stem-like markers (ALDH+ and CD24−, CD44+ tumor cells) will be evaluated in the primary tumor and secondary metastasis/TE samples as previously described for IBC samples (Robertson, 2012).

Experiment 3D: Elucidate Biomarkers for Monitoring Oxidative Stress Response In Vivo Measurement of ROS in vivo carries a significant analytical challenge, as most ROS are highly reactive and short lived, making it difficult to detect directly. Furthermore, it is important to assess oxidative damage at both systemic and tissue-specific levels. The systemic levels of the biomarkers reflect individual oxidative status that may be involved in creating important environmental factors for tumor development and response to treatment (Il'yasova, 2011). The oxidative status of tumor tissue reflects interaction between cellular redox balance and response to treatment. Frequently used biomarkers of oxidative stress, such as protein carbonyl groups and malondialdehyde, are not specific to any particular oxidative processes and have been shown to be unresponsive markers in animal and clinical models of oxidative stress (Halliwell, 2004; Il'yasova, 2009; Il'yasova, 2010; Kadiiska, 2005). Major principles in selecting biomarkers for this study are: (a) chemically stable oxidative modification, (b) measurable in non-cancer patients and normal tissues, (c) reflect ROS-specific chemical modifications. We will use the following markers in tissue, or in peripheral blood samples collected from all the in vivo studies as applicable. 1) SOD1/2 activity in tumor tissue: We will use a superoxide generating system (xanthine and xanthine oxidase) to measure SOD1 and SOD2 enzyme activities. We will quantify the ability of increasing amounts of tumor tissue lysate to inhibit the reduction of NBT to blue formazan (Spitz, 1989). 2) GSH in blood: We will measure depletion of total glutathione and a decreased GSH/GSSG ratio in peripheral blood samples from the tumor studies by HPLC (Rossi, 2006). 3) *Immunohistochemistry*: We will collaborate with Dr. Hwang and the Duke Cancer Center Histology Core to conduct expression of XIAP, Smac, SOD2, and thioredoxin-1 in tumor tissue.

TABLE 4

Summary of 4T1, and SUM149 Murine Window Chamber and Orthotopic Tumor Models in Experiment 3

| Exp't 3 (in vivo) | Treatment | Combination (+/−) | Endpoints (Primary, Secondary) | Mice |
|---|---|---|---|---|
| Exp. 3B—Short-term murine window chamber model for assessment of treatment on invasion and satellite metastasis [HIF1 and NFκB reporter cells] | Vehicle DSF + Cu$ MnP$$ Didox$$$ | RT* Doxorubicin* | Metastasis NFκB/HIF-1 VLD ROS levels Lymphangiogenesis Endpoint (mRNA, protein, activity) Locoregional failure (tumors resected from 5 mice/group post RT/CT) | N = 10/gp |

TABLE 4-continued

Summary of 4T1, and SUM149 Murine Window Chamber and Orthotopic Tumor Models in Experiment 3

| Exp't 3 (in vivo) | Treatment | Combination (+/−) | Endpoints (Primary, Secondary) | Mice |
|---|---|---|---|---|
| Exp. 3C—Determination of treatment strategies on long-term orthotopic mammary tumor growth delay and metastatic model [Luciferase cells] | Vehicle, RT* Doxorubicin* Docetaxel** Lapatinib*** DSF + Cu$ MnP$$ Didox$$$ | Most efficacious treatments from Exp 3B and single agents from Expt. 3C will inform combination strategies | Tumor growth at site of implantation Local and distant secondary metastasis | N = 15/gp |

*Optimum doses determined by sentinel animals
**6 mg/kg,
***100 mg/kg twice daily,
$60 mg/kg DSF + 0.5 mg/kg Cu,
$$0.2 mg/kg loading, 0.1 mg/kg 3 times/wk,
$$$425 mg/kg daily (IP)

Figure 13:
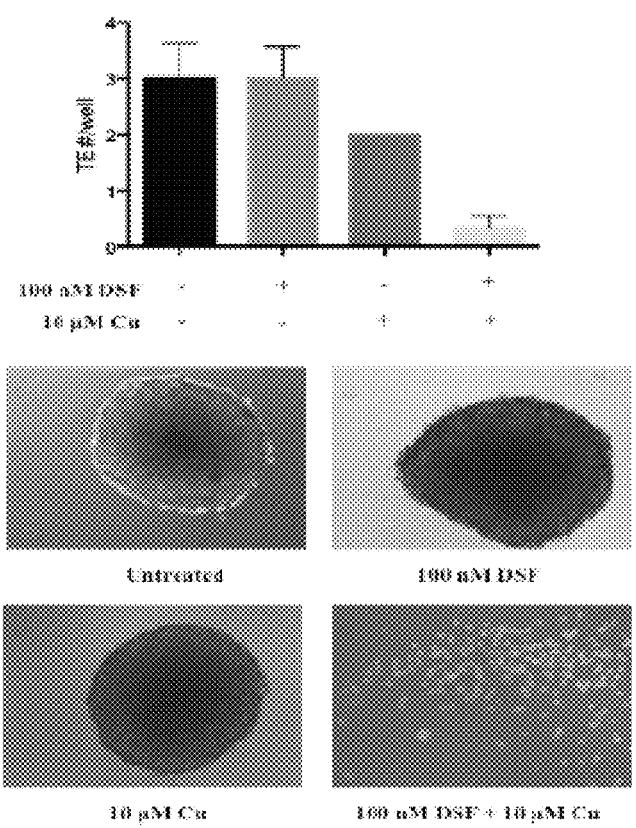
FIG. 13 shows DSF-Cu inhibits in vitro tumor emboli formation.

We anticipate identification of potent combinations that will be superior to single agents in inhibition of tumor growth and/or metastasis. Table 4 also summarizes the in vivo animal studies related to this experiment. Further, DSF is an inhibitor of ALDH, also a marker of tumor stem-like cells and because TE are rich in ALDH1+ve cells, we anticipate DSF-Cu to be effective in inhibition of TE formation as observed in pilot studies (FIG. 13). We expect to identify important oxidative stress response-related biomarkers that can be measured in biopsies and peripheral blood samples and correlate with therapeutic response.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred aspects, are exemplary, and are not intended as limitations on the scope of the invention. Changes therein and other uses will occur to those skilled in the art which are encompassed within the spirit of the invention as defined by the scope of the claims.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method of reducing or inhibiting tumor emboli formation in a patient having inflammatory breast cancer (IBC), the method comprising:
administering to the patient an effective amount of a pharmaceutical composition comprising disulfiram (DSF) and copper (Cu), thereby reducing or inhibiting tumor emboli formation in the patient having IBC.

2. The method of claim 1, wherein the IBC in the patient is a primary cancer or a secondary lesion thereof.

3. The method of claim 1, wherein the patient suffers from chest wall reoccurrence of IBC.

4. The method of claim 1, wherein the administering further thereby ameliorates at least one symptom of IBC that is different than the tumor emboli formation of the IBC.

5. The method of claim 4, wherein the at least one symptom of IBC is selected from the group consisting of pain, ulceration, odor, bleeding, tumor growth, lymphedema and the psychological distress of having visible local disease.

6. The method of claim 1, wherein the method further comprises treatment of the patient with surgery, radiation therapy (RT), or chemotherapy (CT) prior to or concurrently with the administering of the pharmaceutical composition.

7. The method of claim 1, wherein the patient is a mammal.

8. The method of claim 1, wherein the patient is human.

9. The method of claim 1, wherein the tumor emboli of IBC is characterized by an enhancement of the oxidative stress response (OSR) as compared with non-IBC breast cancer.

10. The method of claim 9, wherein the oxidative stress response is characterized by an increase in nuclear transcription factor NFκ-B-dependent activity.

11. The method of claim 9, wherein enhancement of the oxidative stress response (OSR) is characterized by increase in the group consisting of NFκ-B-dependent gene expression, anti-apoptotic protein XIAP, antioxidants SOD1/2, hypoxia-inducible factor HIF-1 and combinations thereof.

12. The method of claim 1, wherein the tumor emboli are characterized by XIAP overexpression within the cells within the tumor emboli compared to non-IBC cells.

13. The method of claim 1, wherein the tumor emboli are resistant to ROS-inducing therapies prior to administration of the pharmaceutical composition.

* * * * *

UNITED STATES PATENT AND TRADEMARK OFFICE
CERTIFICATE OF CORRECTION

PATENT NO. : 10,195,164 B2
APPLICATION NO. : 15/154473
DATED : February 5, 2019
INVENTOR(S) : Gayathri Davi Page 1 of 1

It is certified that error appears in the above-identified patent and that said Letters Patent is hereby corrected as shown below:

In the Specification

Column 13, Line 50, "SU1V1149" should be --SUM149--.

Column 15, Line 17, "DRE" should be --DHE--.

Column 29, Line 62, "cancers" should be --cancers[29].--.

Column 34, Table 1.1, Line 43, "BY" should be --BV--.

Column 35, Table 1.2, Line 21, "Sved" should be --Syed--.

Column 36, Line 67, "cancer" should be --cancer[43].--.

Signed and Sealed this
Nineteenth Day of March, 2019

Andrei Iancu
*Director of the United States Patent and Trademark Office*